United States Patent [19]
Ryan

[11] Patent Number: 5,965,429
[45] Date of Patent: Oct. 12, 1999

[54] STRAIN FOR THE PRODUCTION OF 6-DEMETHYLTETRACYCLINE, METHOD FOR PRODUCING THE STRAIN AND VECTOR FOR USE IN THE METHOD

[75] Inventor: Michael J. Ryan, West Milford, N.J.

[73] Assignee: American Cyanamid Company, Wayne, N.J.

[21] Appl. No.: 09/031,855

[22] Filed: Feb. 27, 1998

Related U.S. Application Data

[63] Continuation of application No. 08/475,889, Jun. 7, 1995, abandoned.

[51] Int. Cl.$^6$ .............................. C12N 1/21; C12N 15/76; C12P 29/00; C07H 21/04
[52] U.S. Cl. .................. 435/252.35; 435/64; 435/253.5; 435/320.1; 435/889; 536/23.1
[58] Field of Search .......................... 435/252.35, 320.1, 435/253.5, 64, 889, 170; 514/152; 552/203, 204, 205, 206; 536/23.1

[56] References Cited

U.S. PATENT DOCUMENTS

| | | | |
|---|---|---|---|
| 3,616,241 | 10/1971 | Growich, Jr. ............................. | 435/64 |
| 3,639,214 | 2/1972 | Mercer et al. ............................ | 435/64 |
| 5,589,385 | 12/1996 | Ryan et al. ......................... | 435/285.35 |
| 5,639,949 | 6/1997 | Ligon et al. ........................... | 800/20.5 |
| 5,643,753 | 7/1997 | Loosmore et al. .................... | 435/69.3 |

OTHER PUBLICATIONS

Pelletier et al., Cloning of a Second Non–Haem Bromoperoxidase Gene from *Streptomyces aureofaciens* ATCC 10762:Sequence Analysis, Expression in *Streptomyces lividans* and Enzyme Purification, Microbiology, 140:509–516, 1994.

Kormanec et al., Optimization of *Streptomyces aureofaciens* Transformation and Disruption of the hrdA Gene encoding a Homologue of the Principal δ Factor, Journal of General Microbiology, 139:2525–2529, 1993.

Godany et al., The *Streptomyces aureofaciens* Plasmid pIMB R8 and its Use For Shuttle Vector Construction, J. Basic Microbiol., 30:10.729–735, 1990.

van Pee, Karl–Heinz, Molecular cloning and High–Level Expression of a Bromoperoxidase Gene from *Streptomyces aureofaciens* Tü24, Journal of Bacteriology, 170:5890–5894, 1988.

Mahmood et al., Chlortetracycline Production with Immobilized *Streptomyces aureofaciens*, Appl. Microbiol. Biotechnol., 26:333–337, 1987.

Mahmood et al., Chlortetracycline Production with Immobilized *Streptomyces aureofaciens*, Appl. Microbiol. Biotechnol., 26:338–341, 1987.

*Primary Examiner*—Nancy Degen
*Attorney, Agent, or Firm*—Darby & Darby

[57] ABSTRACT

Recombinant *S. aureofaciens* cells are provided. These cells comprise: (a) at least one CTC 11 gene; and (b) optionally
 (i) a CTC 09 gene;
 (ii) a CTC 03 gene; or
 (iii) a combination thereof;
wherein:
 the CTC 11 gene is chromosomal, extra-chromosomal, or chromosomal and extra-chromosomal;
 the CTC 09 gene, CTC 03 gene, or a combination thereof is chromosomal, extra-chromosomal, or a combination thereof; expression of the CTC 11 gene is enhanced over that of a wild-type *S. aureofaciens* cell; and
 optionally, the CTC 09 gene, the CTC 03 gene, or both of the CTC 09 gene and the CTC 03 gene are inactivated.

The present invention also contemplates vector pLP21329 and vectors for allelic replacement in a *S. aureofaciens* host cell. The vectors comprise:

(a) a functional *E. coli* origin of replication;
(b) a functional Streptomyces origin of replication;
(c) a functional gene that imparts a positively selectable phenotype on the host cell; and
((d) a ribosomal S12 gene which is expressed in Streptomyces such that it imparts sensitivity to streptomycin to the host cell. In another embodiment, a method of mutating a target gene of a biosynthetic pathway of Streptomyces is disclosed. The method comprises
 (a) replacing the genomic copy of the target gene with a selectable marker gene through homologous recombination to form a first recombinant strain; and
 (b) replacing the selectable marker gene in the first recombinant strain with an altered copy of the target gene through homologous recombination to form a second recombinant strain.

27 Claims, 47 Drawing Sheets

FIG. IA
Biosynthesis of Chlortetracycline
Acetate
Malonyl CoA   Malonamoyl CoA
Matrix-bound Polyketide Amide
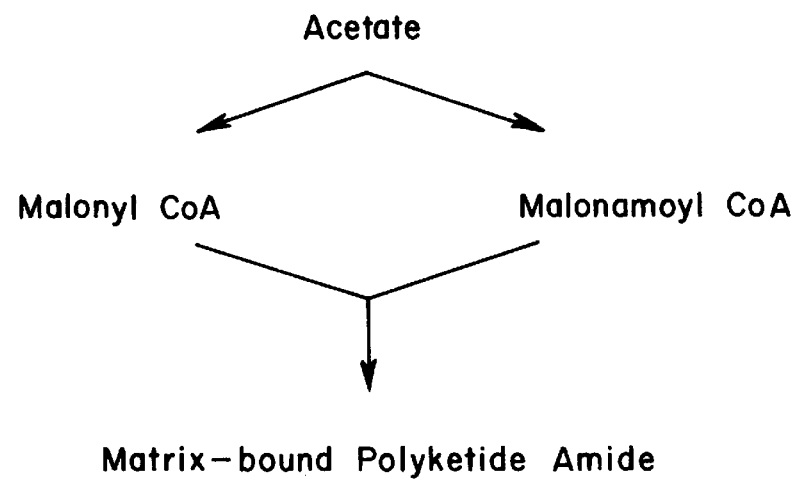
↓ I
Methylated Polyketide Amide
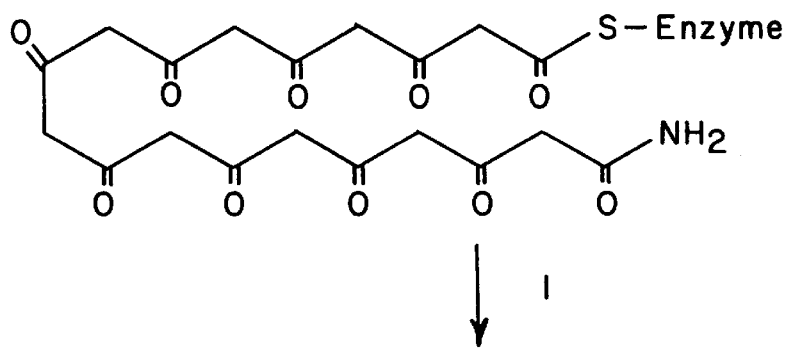
A —————————————|————————————— A

FIG. 1B
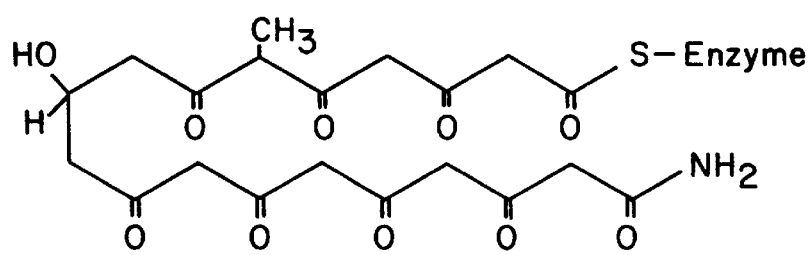
6 — Methylpretetramid
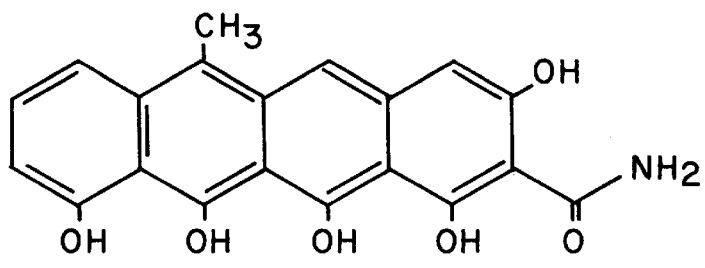
4 — Hydroxy — 6 — Methylpretetramid
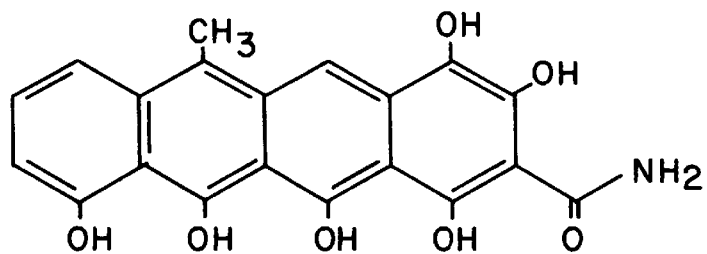

FIG. IC
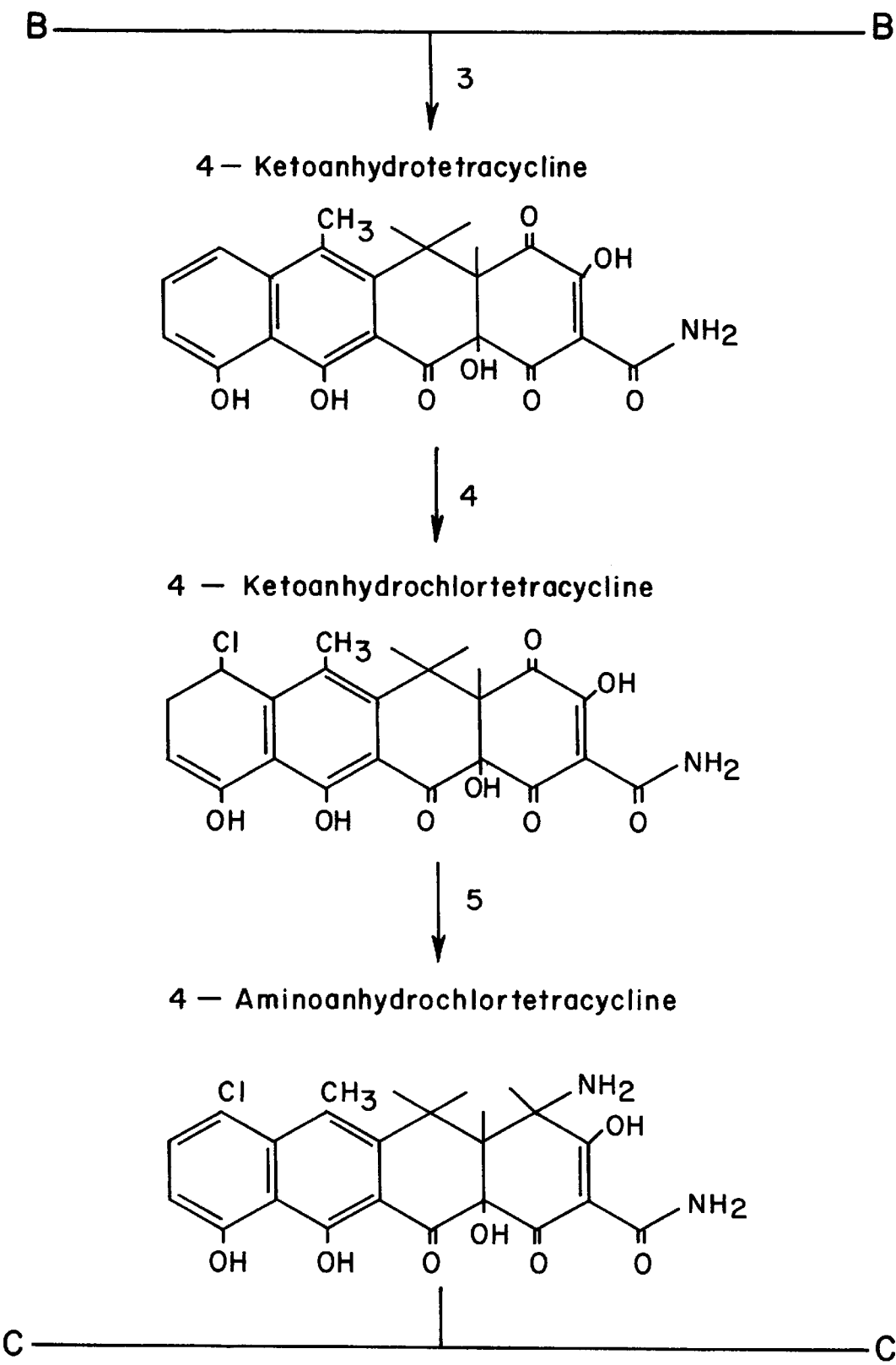

FIG. 1D
C ——————————————↓6—————————————— C
Anhydrochlortetracycline
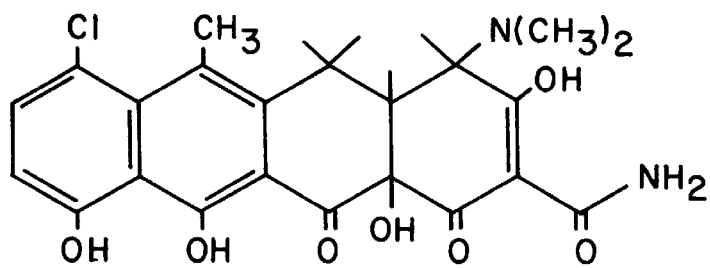
↓7
Dehydrochlortetracycline
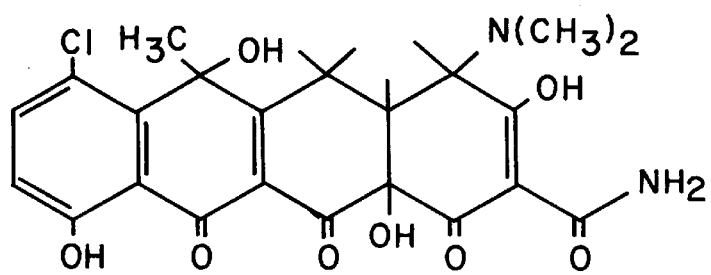
↓
Chlortetracycline
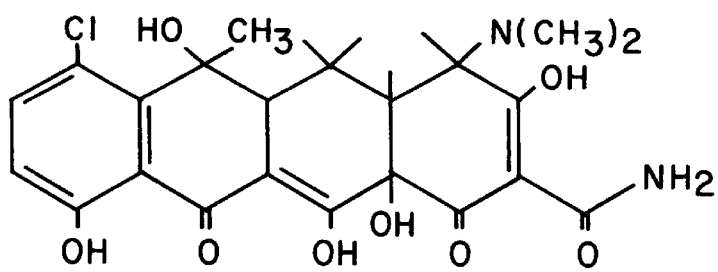

FIG. 4B

```
CGTCGTTGCGAGCACGGCTTGATCCGCTCCCACACCTGCGAGAAGT
CCTTGGCGTCCAGGGCTTGTAGATCGTTGACGTGGCACCCTTGTG
GGGAAGGCAGCGCCGGGACAAGGTGTTGCACGATAGGTGAGCAACG
GACCCTCAGCGCCCGCCCCGAGACGGTGGCTCCCCCAGCCGCCGAT

NheI       EcoRI
        CGAGGGCTAGCCCCTCGAATTC
```

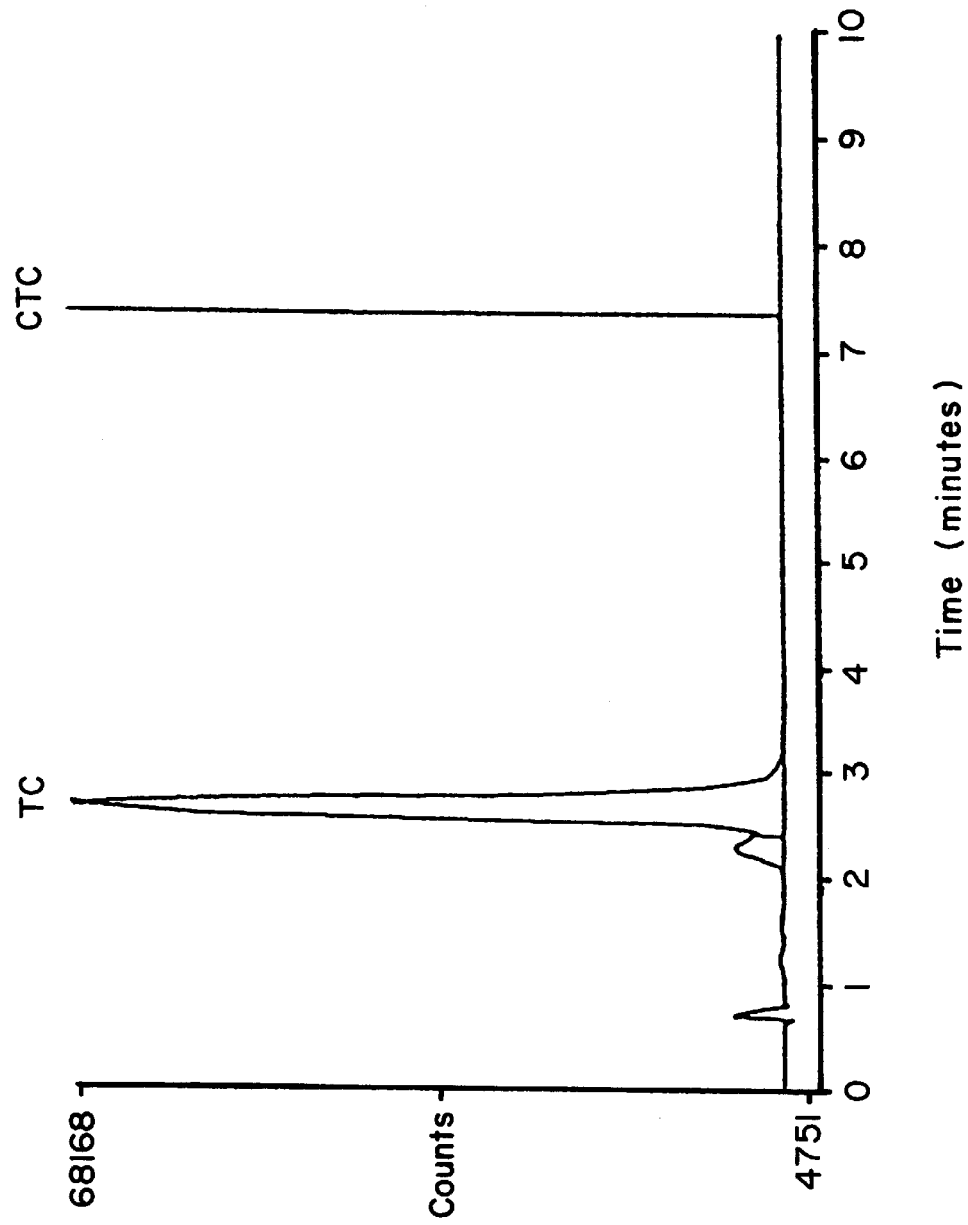

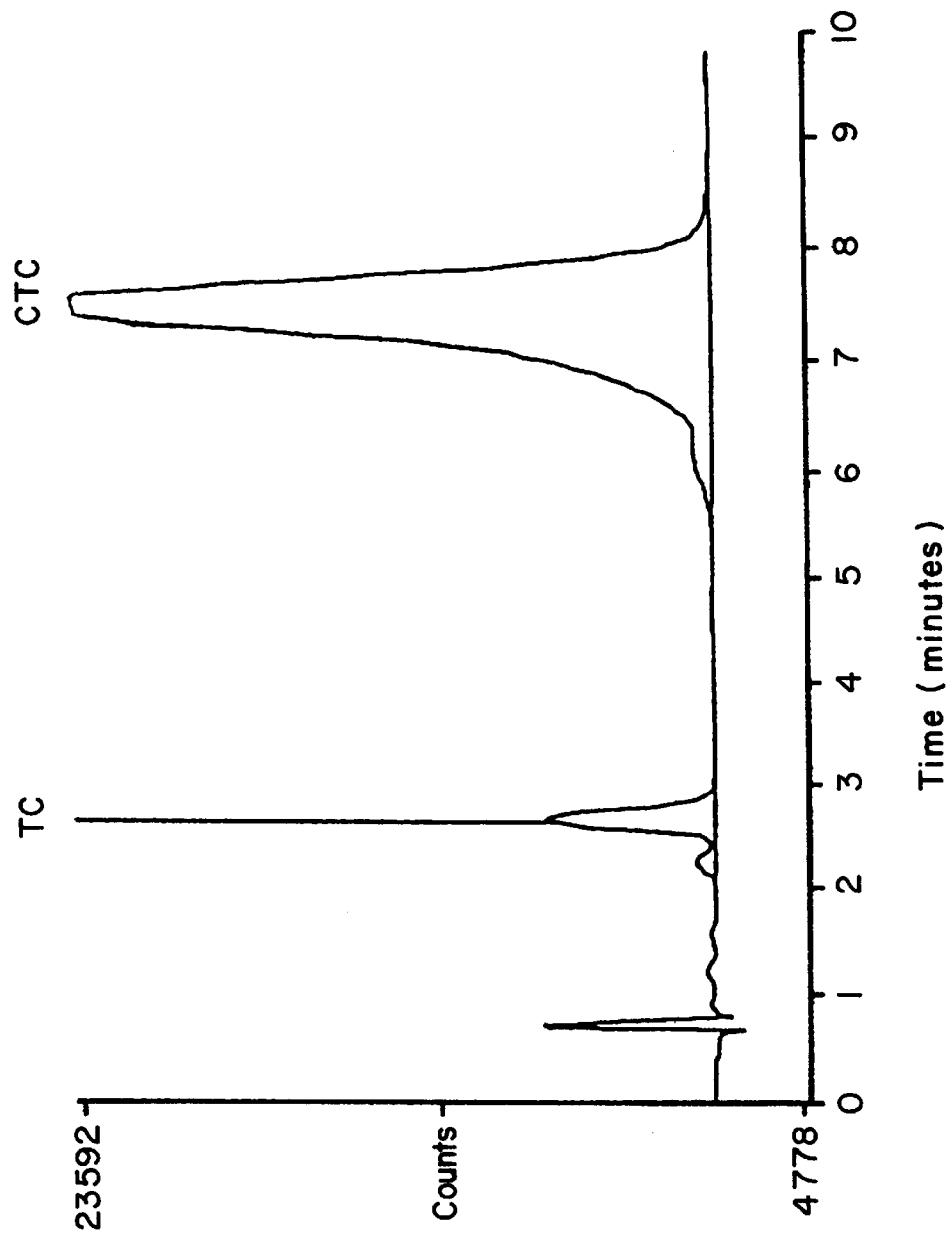

FIG. 12B
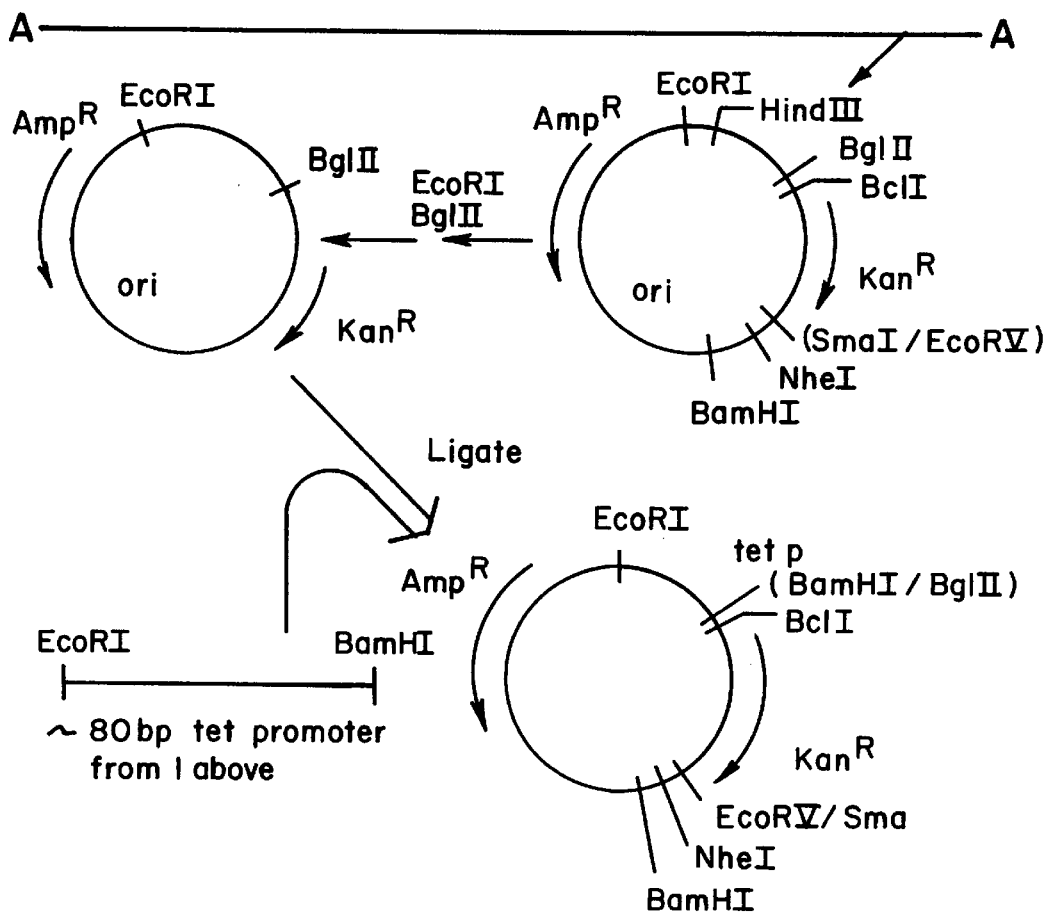
3. Transfer tet p — Kan^R fragment from #2 → pIBI25 polylinker as an EcoRI—BamHI fragment to the same sites in pIBI25
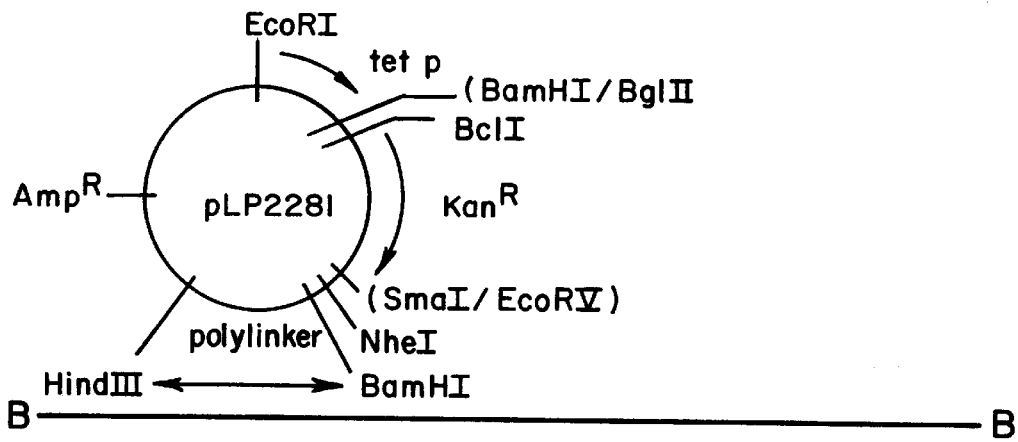

FIG. 14B
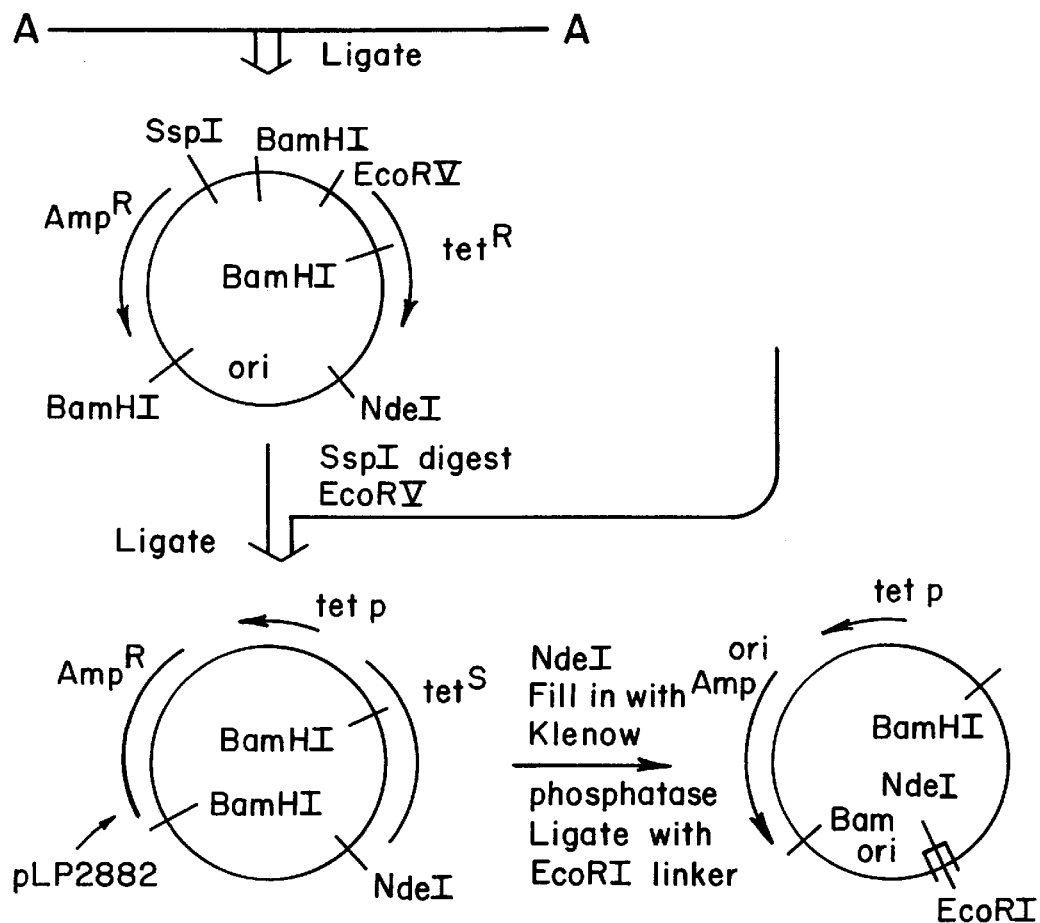
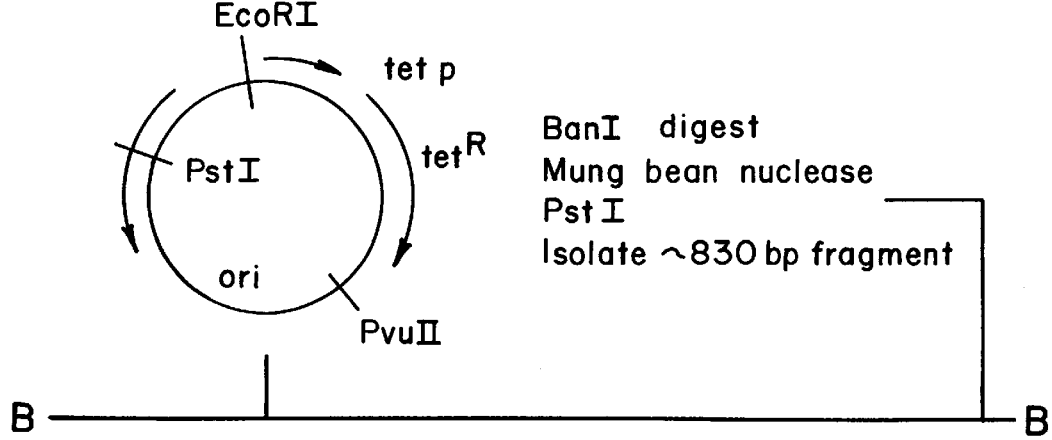
III-A "Below" construction / isolation of an ~80 bp, flush ended, tet promoter

FIG. 14C
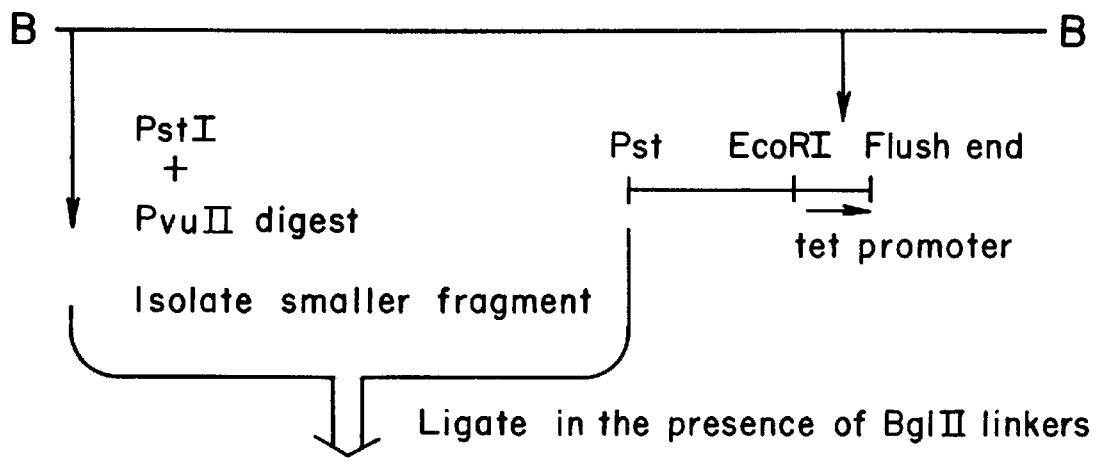
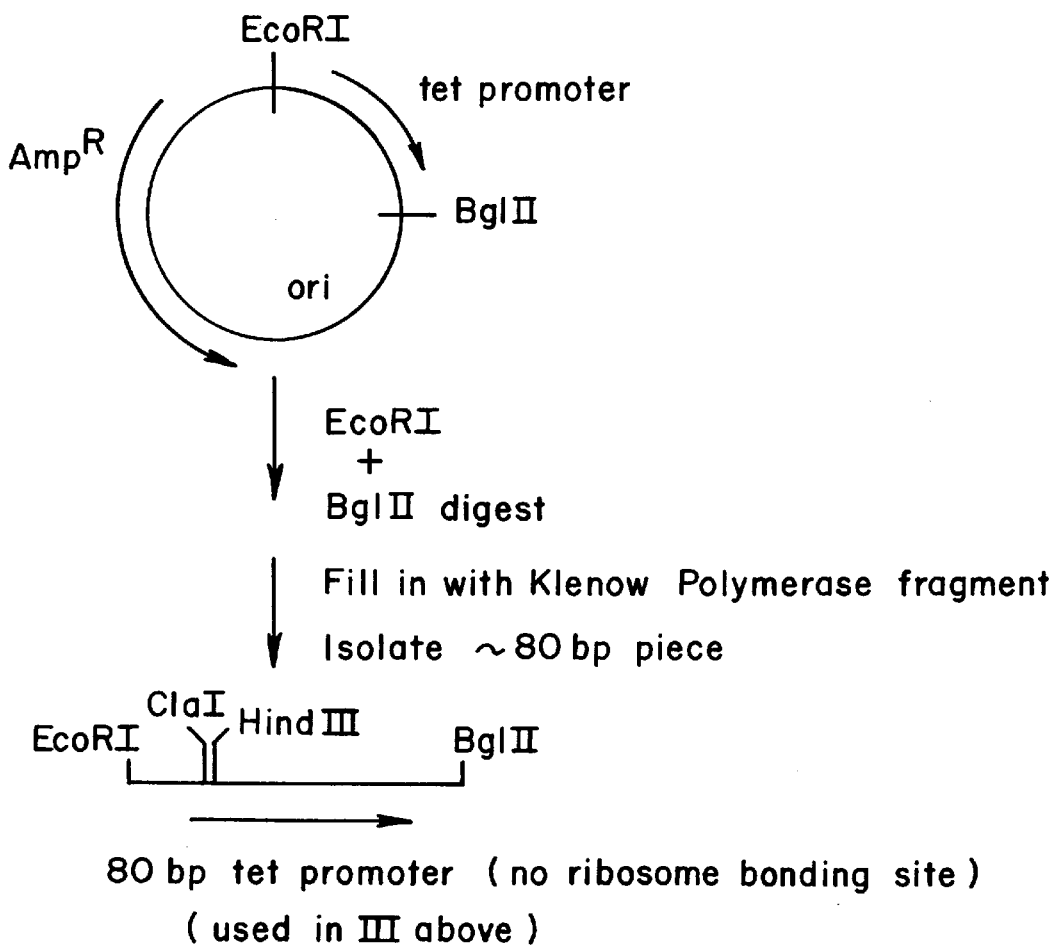
80 bp tet promoter (no ribosome bonding site)
(used in III above)

FIG. 15
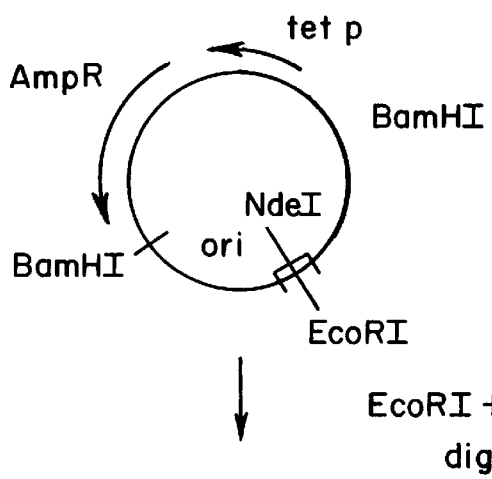
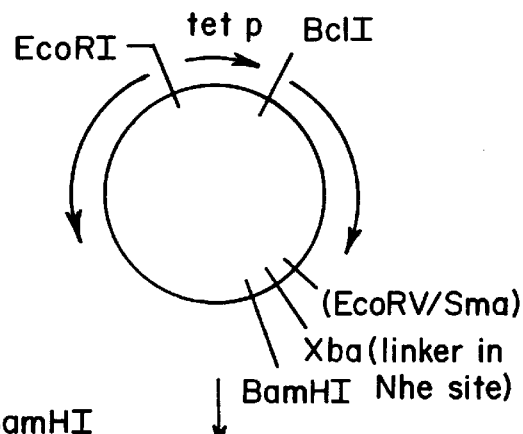
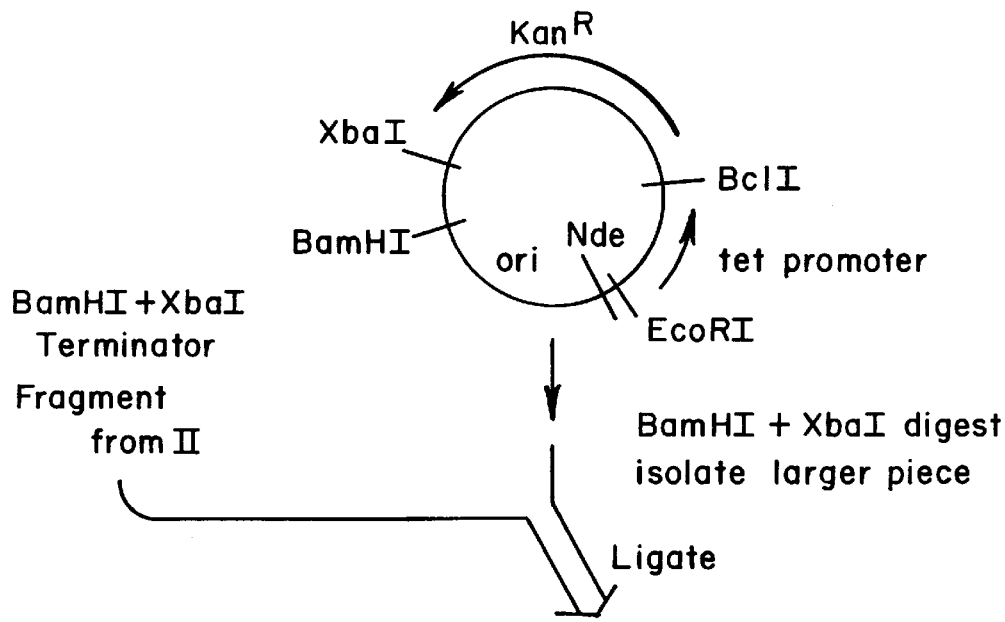
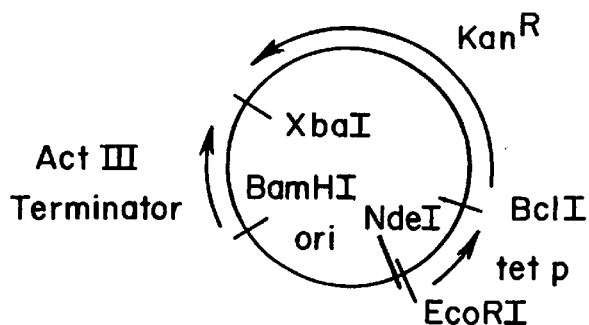

1. pEC14 (Figure 17) Micromonospora promoter fragment of pPPI4 (Figure 3) moved to puc19 as Hind III — Bam fragment.

— pEC14 pstI digest → Fill in → phosphatase → ligate to a Bgl II linker

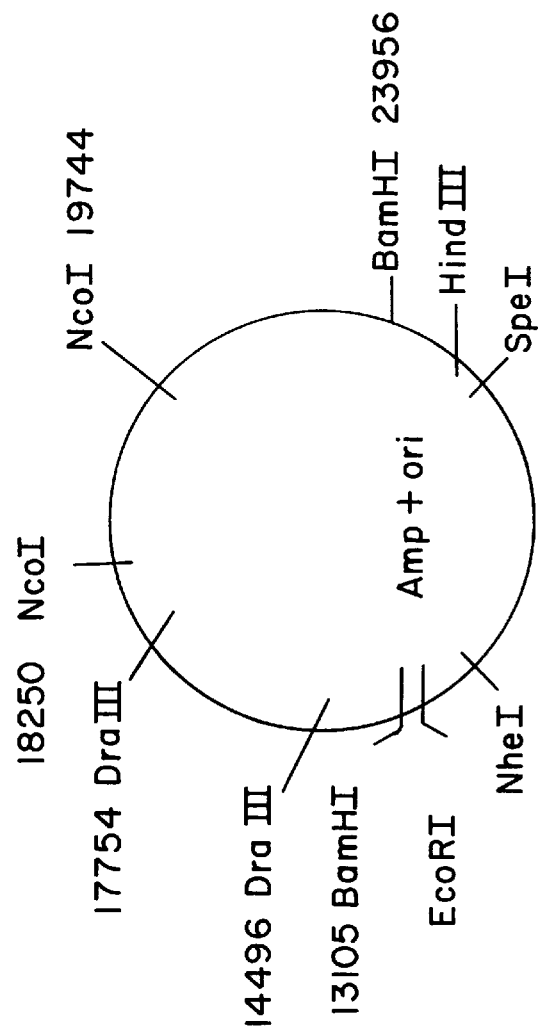
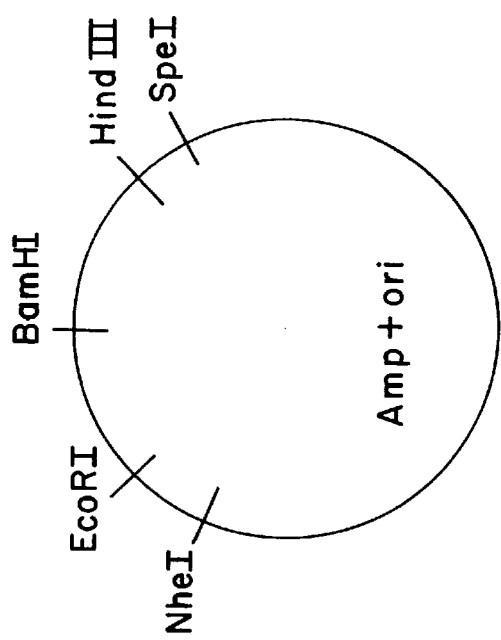
FIG. 28

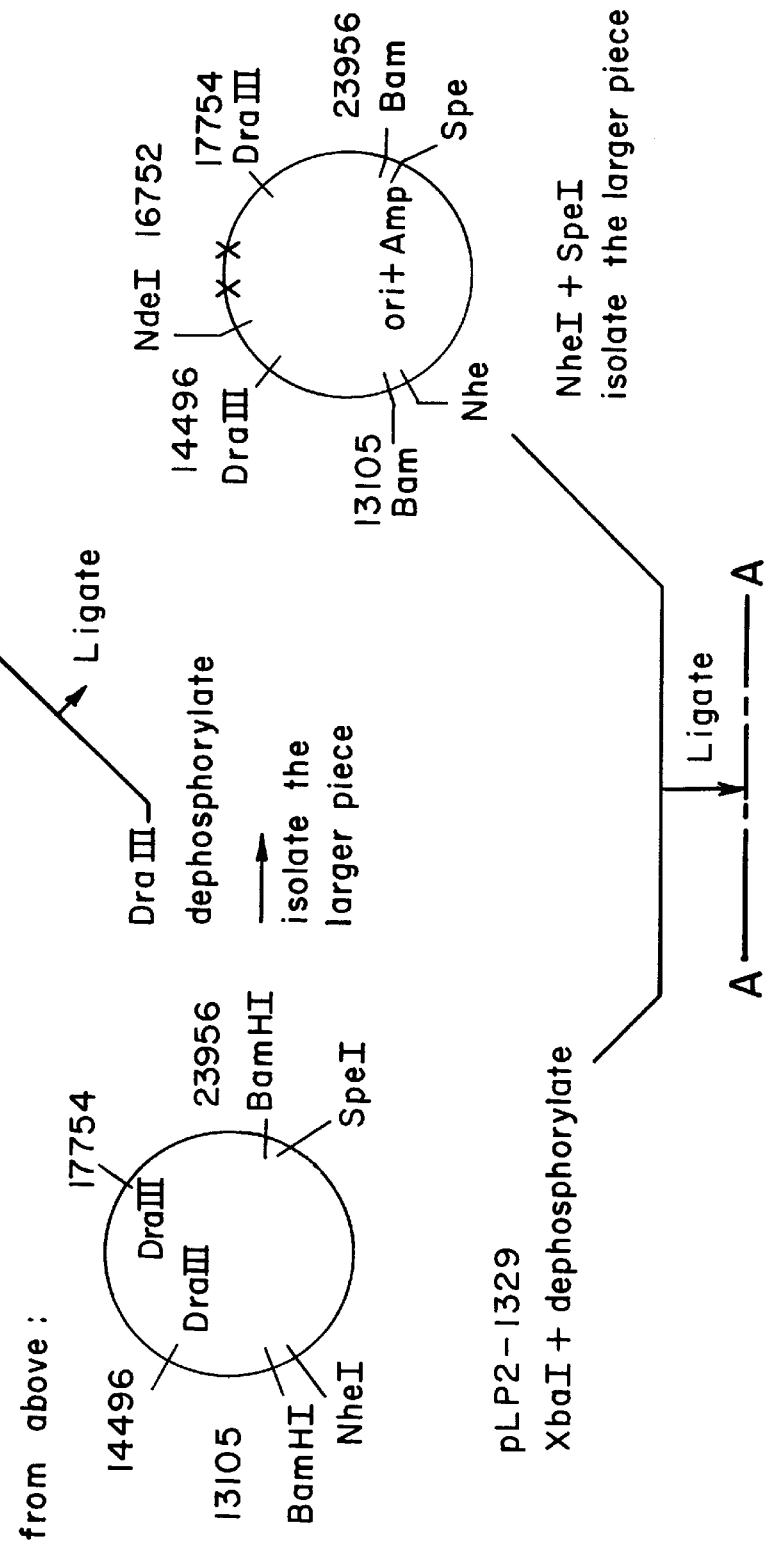

STRAIN FOR THE PRODUCTION OF 6-DEMETHYLTETRACYCLINE, METHOD FOR PRODUCING THE STRAIN AND VECTOR FOR USE IN THE METHOD

This application is a continuation of U.S. Ser. No. 08/475,889, filed Jun. 7, 1995, now abandoned.

FIELD OF THE INVENTION

This invention relates to the production of high levels of tetracycline derivatives such as, for example, 6-demethyl tetracycline and 6-demthyl chlortetracycline, by genetically altered Streptomyces strains, such as *Streptomyces aureofaciens*.

BACKGROUND OF THE INVENTION

Chlortetracycline and related compounds (e.g., tetracycline, 6-demethyl chlortetracycline, 6-demethyl tetracycline) are widely used as antibiotics, additives to animal feed, and intermediates in the synthetic production of other antibiotic drugs. These compounds are typically produced commercially in submerged fermentation by *Streptomyces aureofaciens*. See, e.g., U.S. Pat. Nos. 3,005,023 and 3,019,173; Merck Index, Eleventh Edition (1989). Sophisticated fermentation techniques, media formulations, and high-producing mutants of *S. aureofaciens* have resulted in increased yields of chlortetracycline and its derivatives. See Goodman, *Handbook of Experimental Pharmacology*, 78:5–57 eds. Hlavka and Boothe (1985); Veselova, *Antiobiotiki*, 14:698–702, 1969. However, some derivatives can only be produced efficiently semi-synthetically.

Recently, recombinant DNA techniques iwere used to the isolate the gene cluster encoding the proteins responsible for the biosynthetic pathway for producing tetracycline, chlortetracycline, and other derivatives from *S. aureofaciens* (see, U.S. application Ser. No. 08/125,468 filed Sep. 22, 1993 now U.S. Pat. No. 5,589,385). This genetic information is used in the present invention to produce genetically altered strains which produce high levels of a desired biosynthetic product.

Because tetracycline and its derivatives are such useful compounds, new selective, increased yield methods and vehicles for the preparation of one or more of these tetracycline compounds are desired.

BRIEF DESCRIPTION OF THE DRAWINGS

FIGS. 1A–1D are illustrations of the biosynthetic pathway for the production of chlortetracycline. The step numbers of this Figure are referenced in Table 2 below.

FIGS. 4A-4B are illustrations of the nucleotide sequence of the heterologous promoters derived from *Micromonopora echinospora* (MP).

FIGS. 9A-9B are illustrations of HPLC graphs of the products of a control culture (left panel) and the products produced when CTC 03 is expressed from pLP21206 in a chlortetracyline (CTC) producing host (right panel).

TABLE 1

Figure 10:
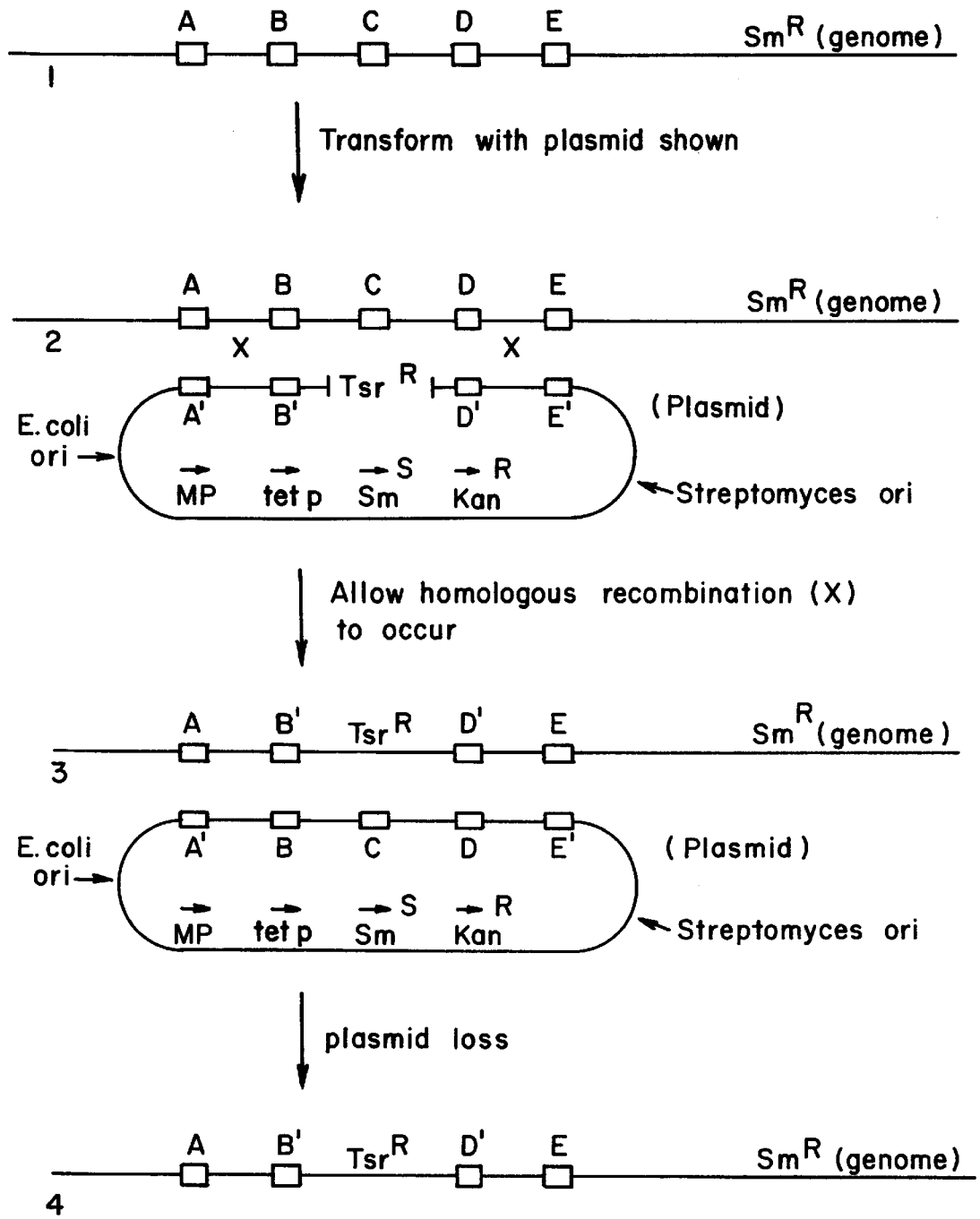
FIG. 10 is a diagram of the first homologous recombination event (HR-1) in the methods of the present invention. As indicated, the desired recombinants include a selectable marker at the genomic locus of the target gene. Table 1 is a key to the symbols used in FIG. 10.
Figure 11:
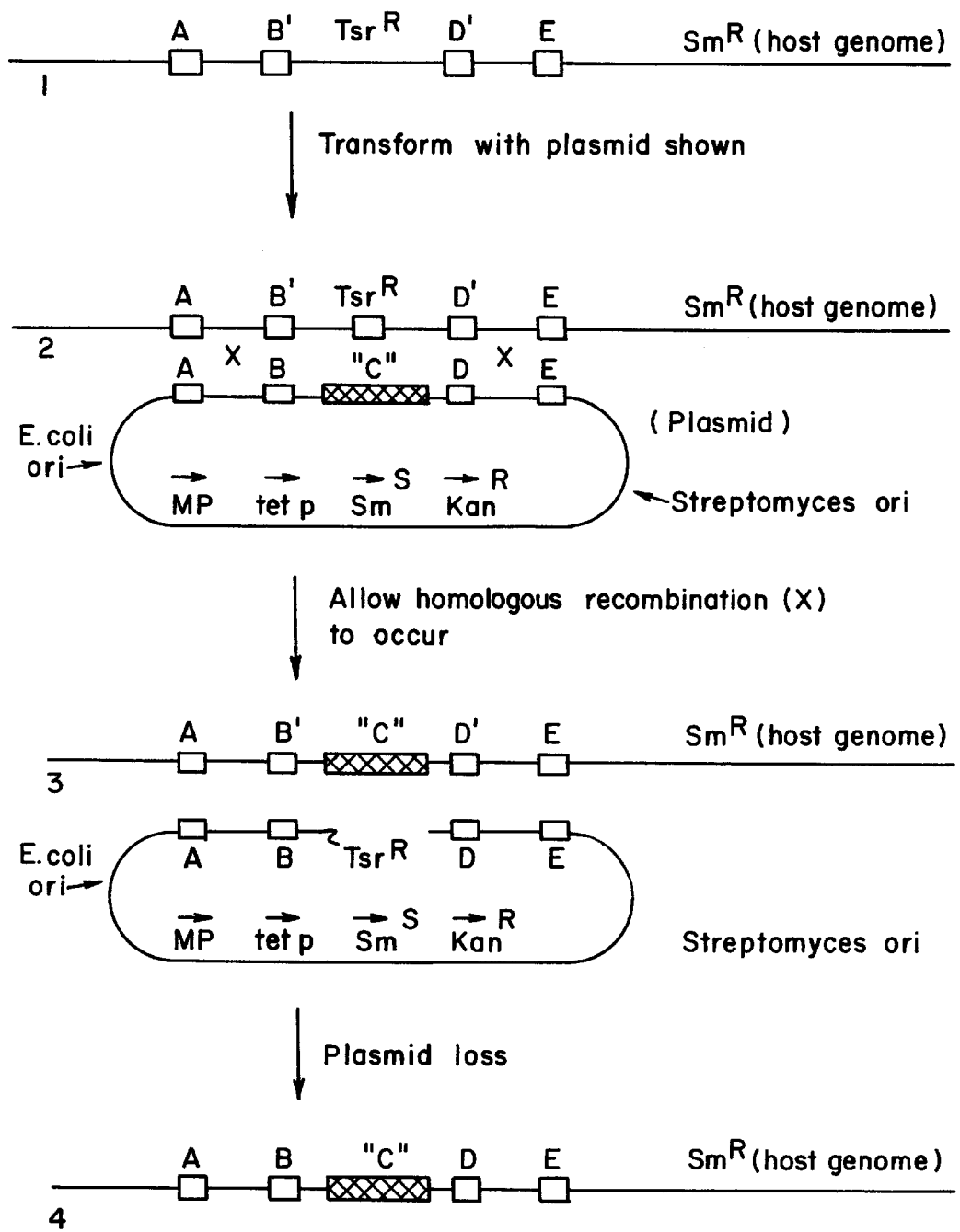
FIG. 11 is a diagram of the second homologous recombination event (HR-2) in the methods of the present invention. As indicated, the desired recombinants include the altered allele of the target gene at its genomic locus and have the function of the flanking genes in the cluster restored. Table 1 is a key to the symbols used in FIG. 11.

Symbols Used in FIGS. 10 and 11

| | |
|---|---|
| $Sm^R$ | resistance to 100 µg/ml of streptomycin |
| $Sm^S$ | sensitivity to streptomycin; dominant phenotype: S12 ribosomal protein from *Micrococcus luteus* |
| $TSr^R$ | resistance to 25–50 µg/ml of thiostrepton |
| $Kan^R$ | resistance to 50 µg/ml of kanamycin |
| MP | Micromonospora promoters (see text for further discussion) |
| $Tet_p$ | *E. coli* promoter from pBR322 tetracycline resistance |
| $MP_{v\ Tetp\ Sm}^R$ | expression cassette for selectable markers which |
| $Kan^R$ | functions in both Streptomyces and *E. coli* |
| ori *E. coli* | DNA fragment for replication in *E. coli* |
| ori Streptomyces | pNA fragment for replication in Streptomyces |
| C | genomic copy of target gene (e.g. CTC 11, CTC 09, or CTC 03) |
| A, B, D, E | genomic copy of flanking biosynthetic genes (HR1) vector copy of flanking biosynthetic genes (HR2) |
| "C" | altered copy of target gene on vector (HR2) |
| A', B', D', E' | vector copy of flanking biosynthetic genes (HR1) |
| A, B', D', E | genomic copy of flanking biosynthetic genes (HR2) |

Figure 12A:
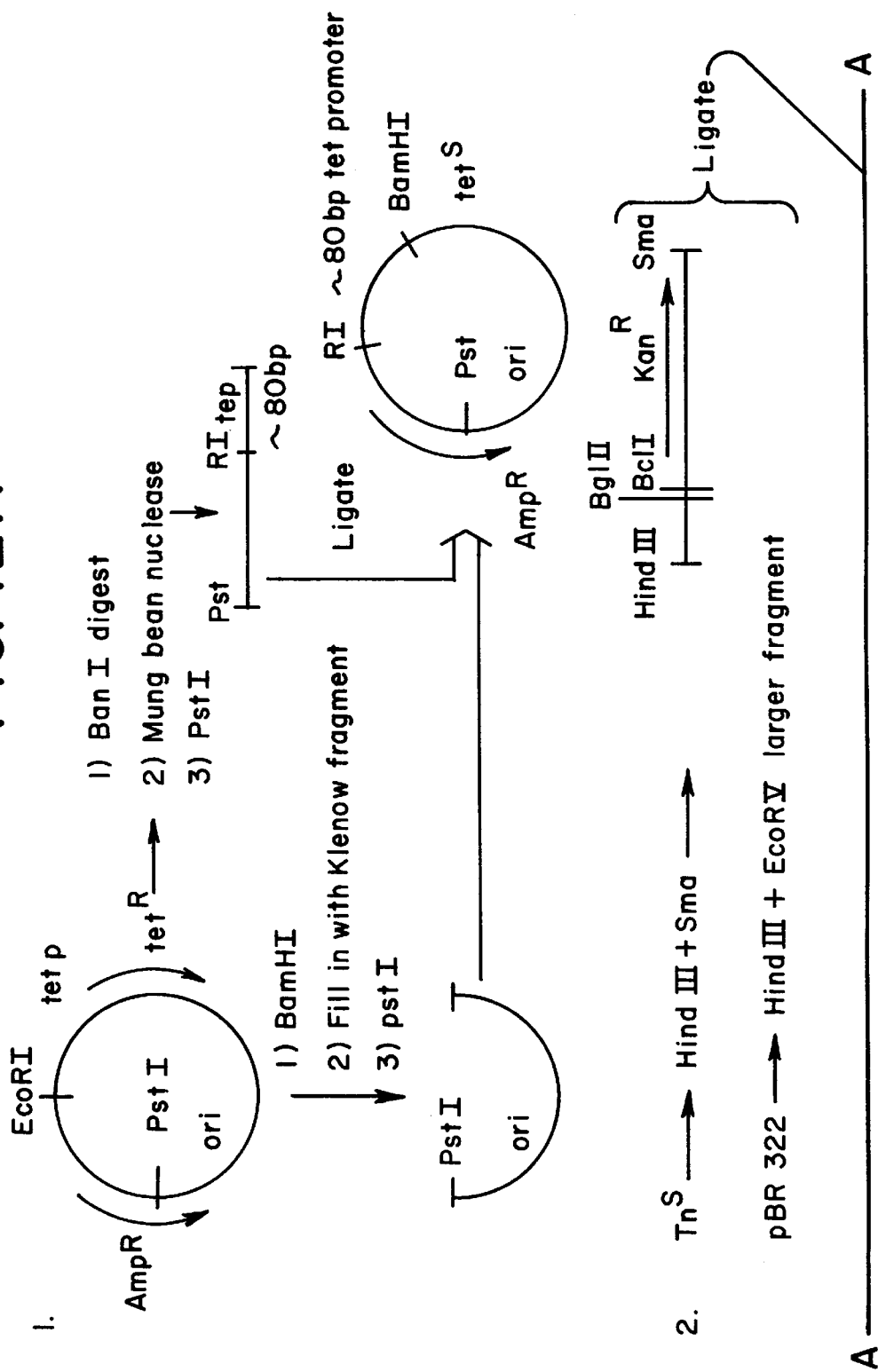
Figure 12C:
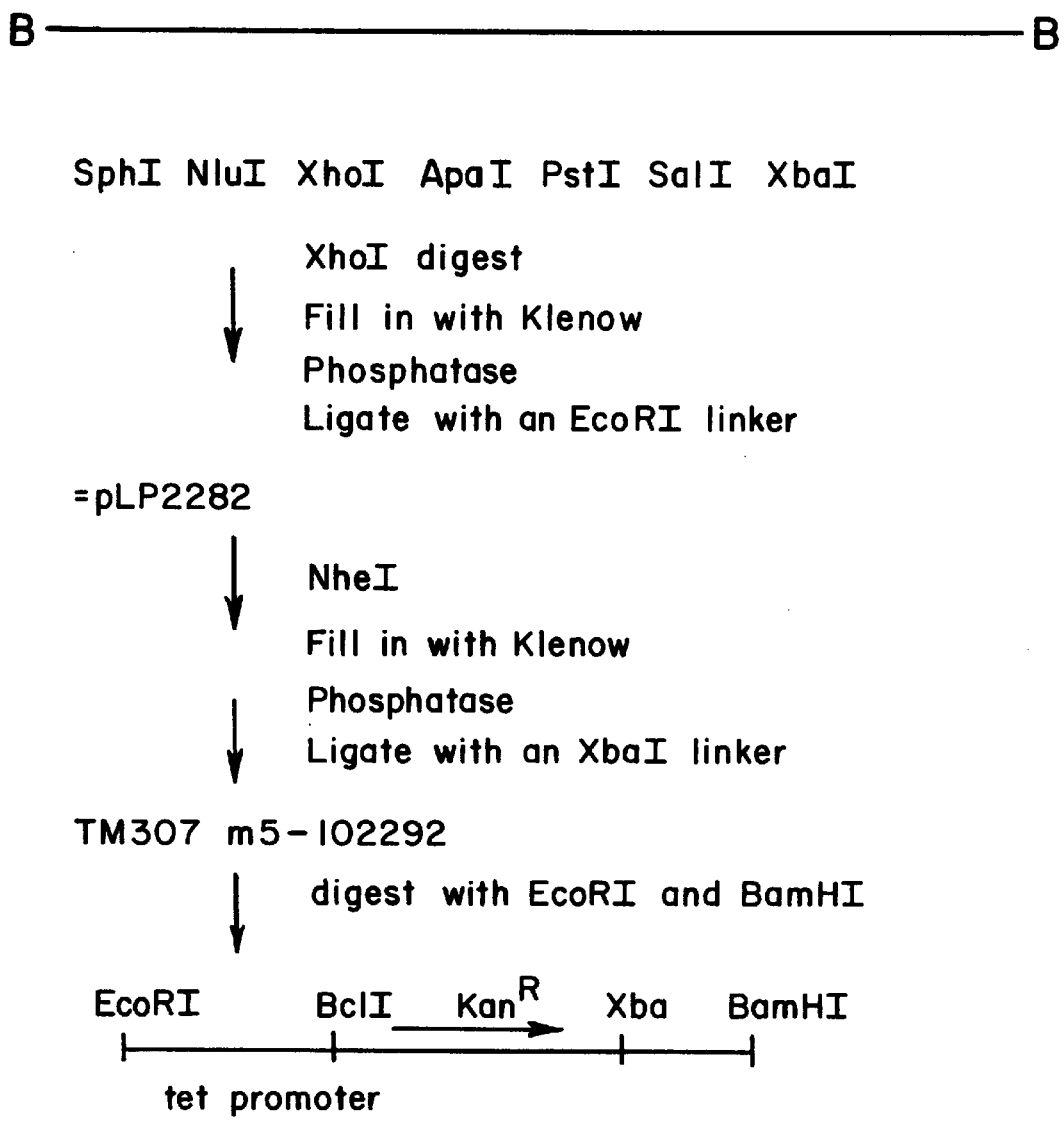

FIGS. 12A–12C are illustrations of the isolation of the *E. coli* promoter for vector pLP21329.

Figure 13A:
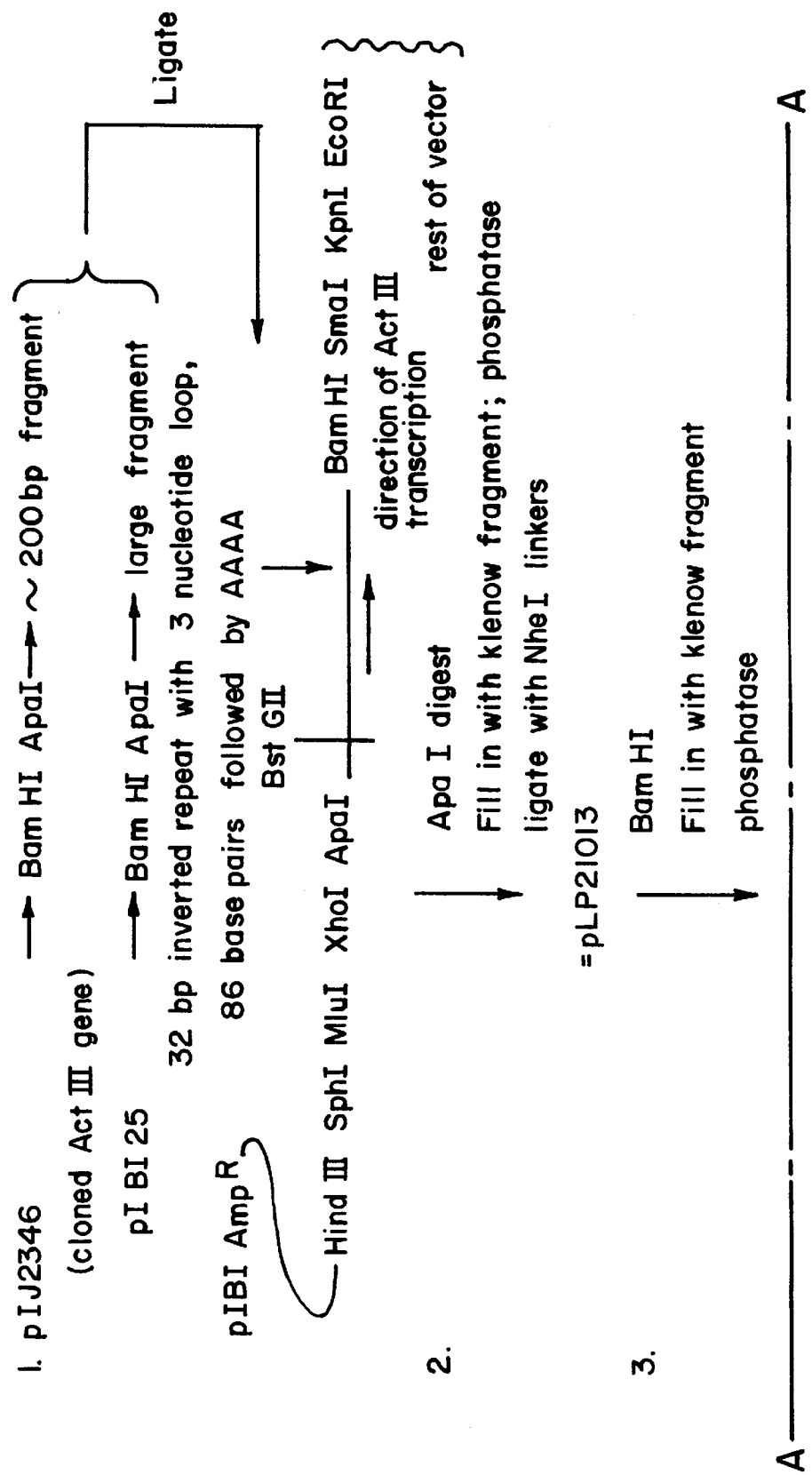
Figure 13B:
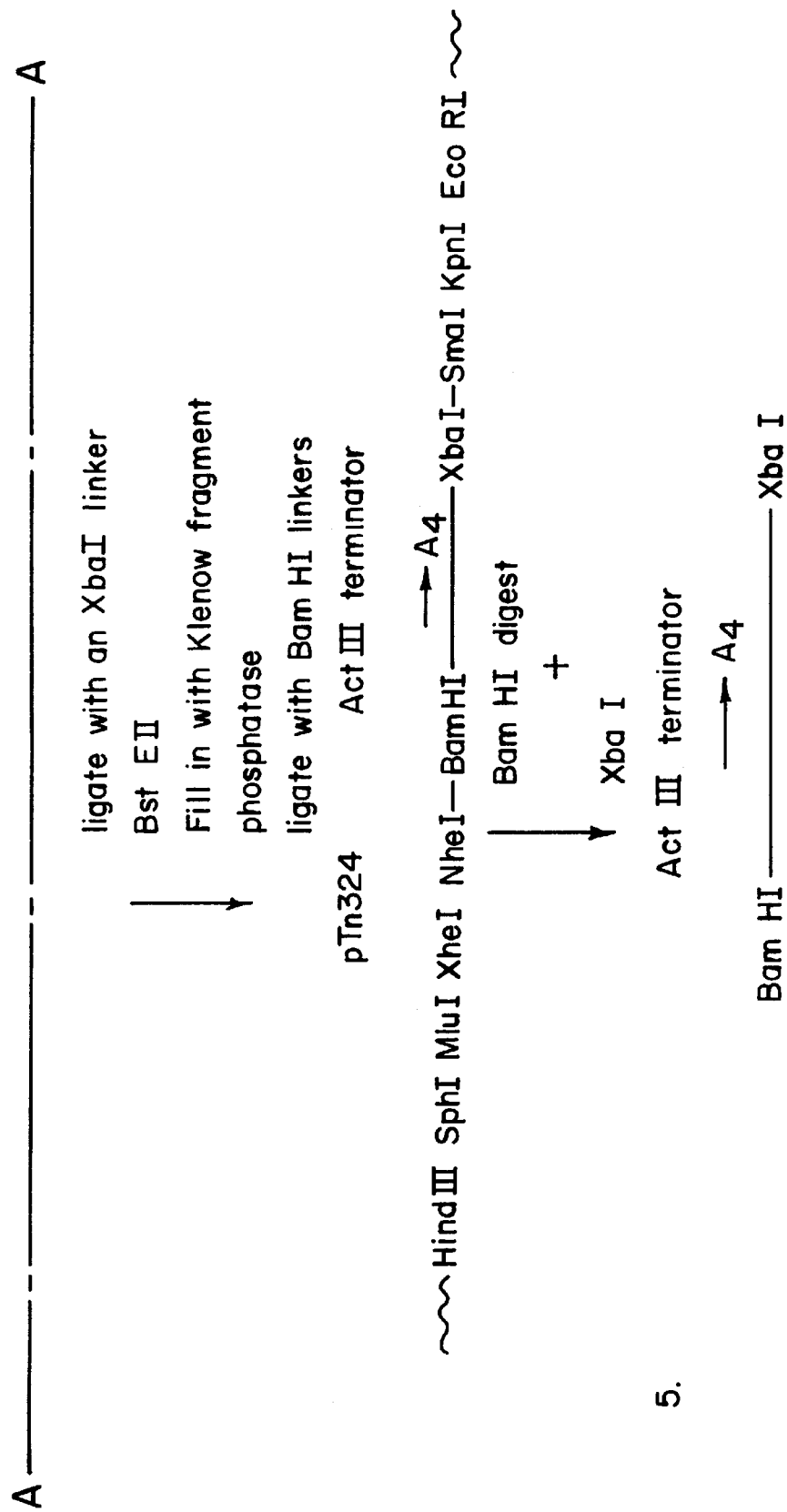

FIGS. 13A-13B are illustrations of the isolation of the transcription terminator for vector pLP21329.

Figure 14A:
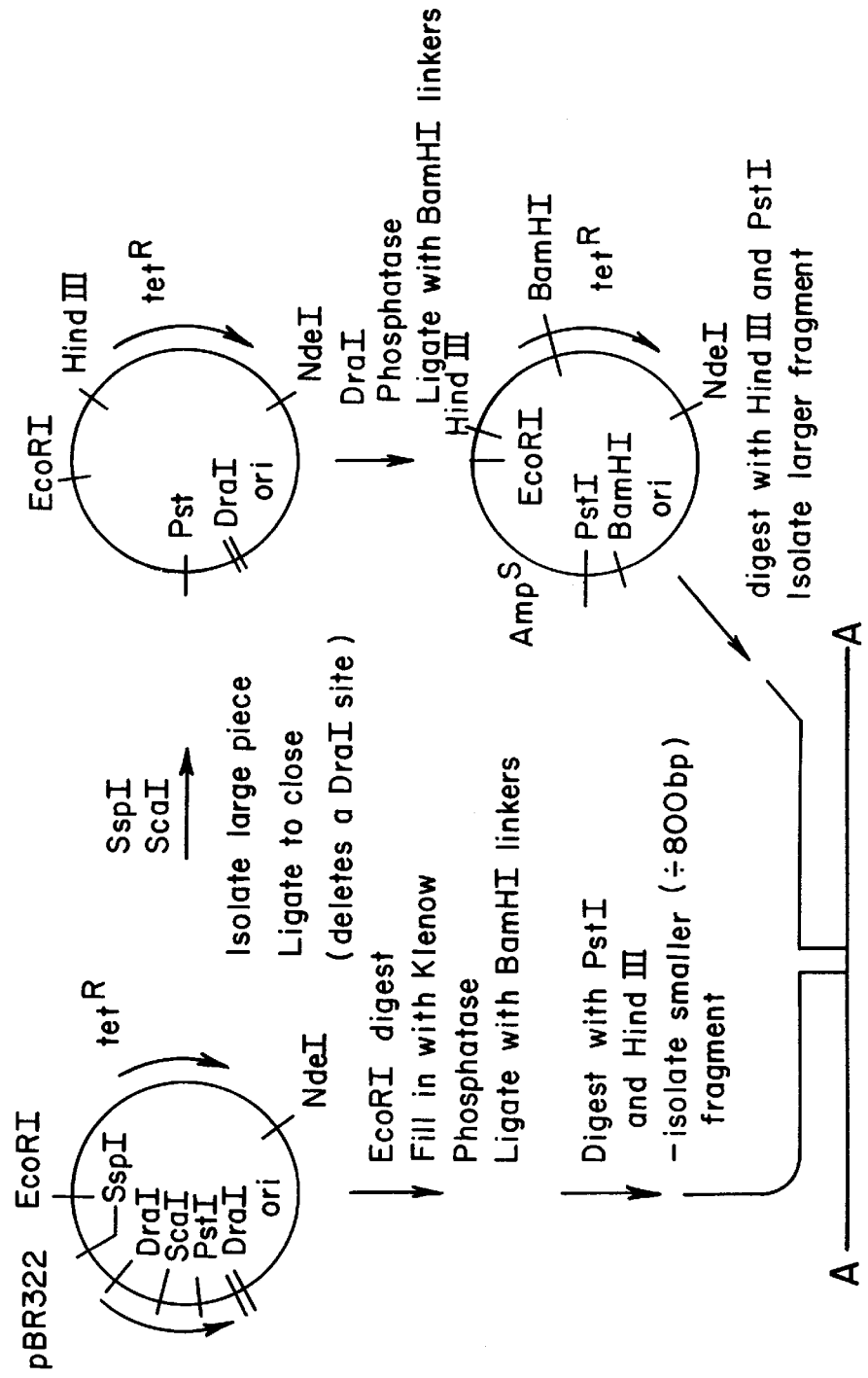

FIGS. 14A–14C are illustrations of the isolation of the *E. coli* origin of replication for vector pLP21329.

FIG. 15 is an illustration of the linking of the isolated promoter with the isolated terminator.

Figure 16:
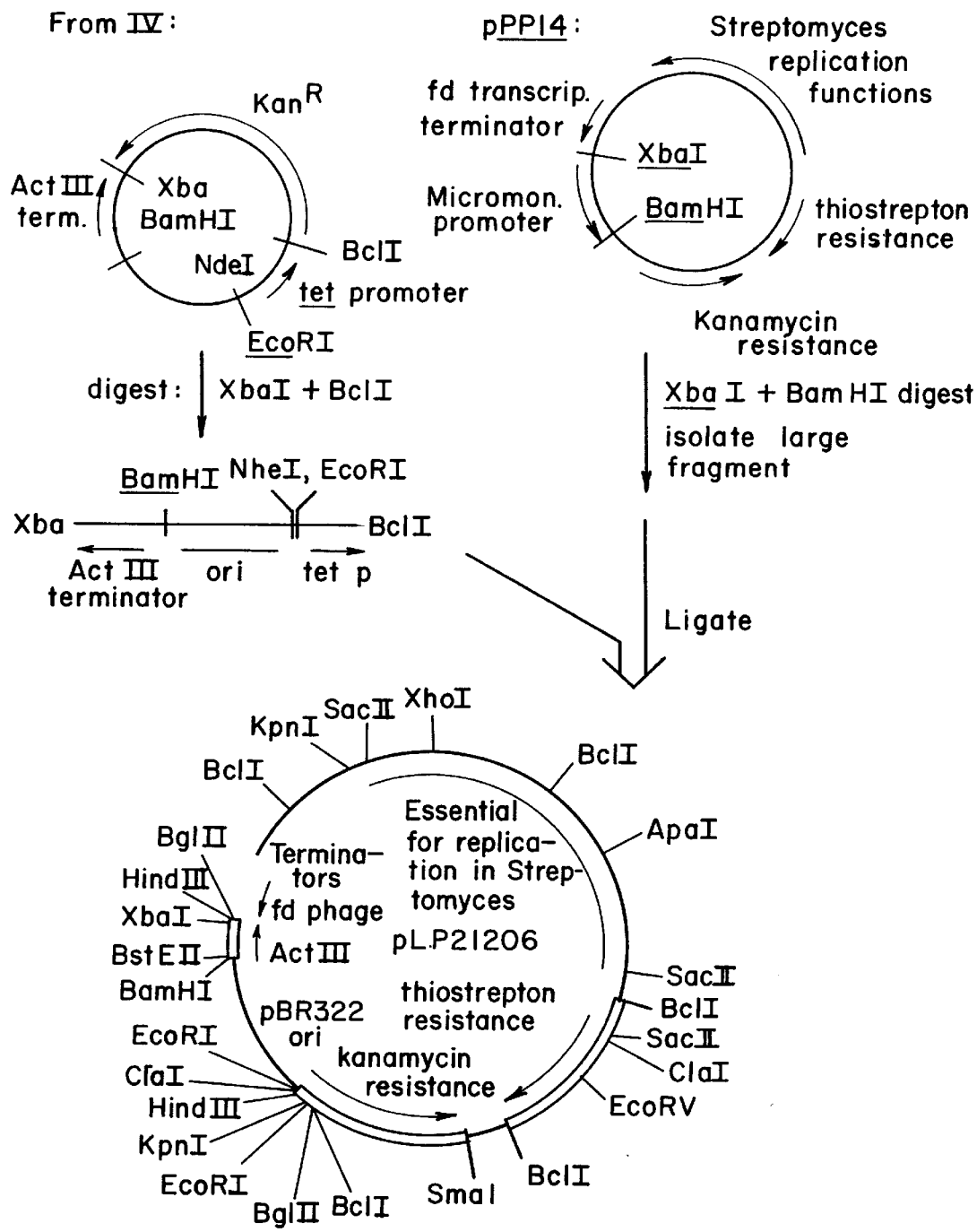

FIG. 16 is an illustration of the ligation of the fragment produced in FIG. 15 into pPP14.

Figure 17:
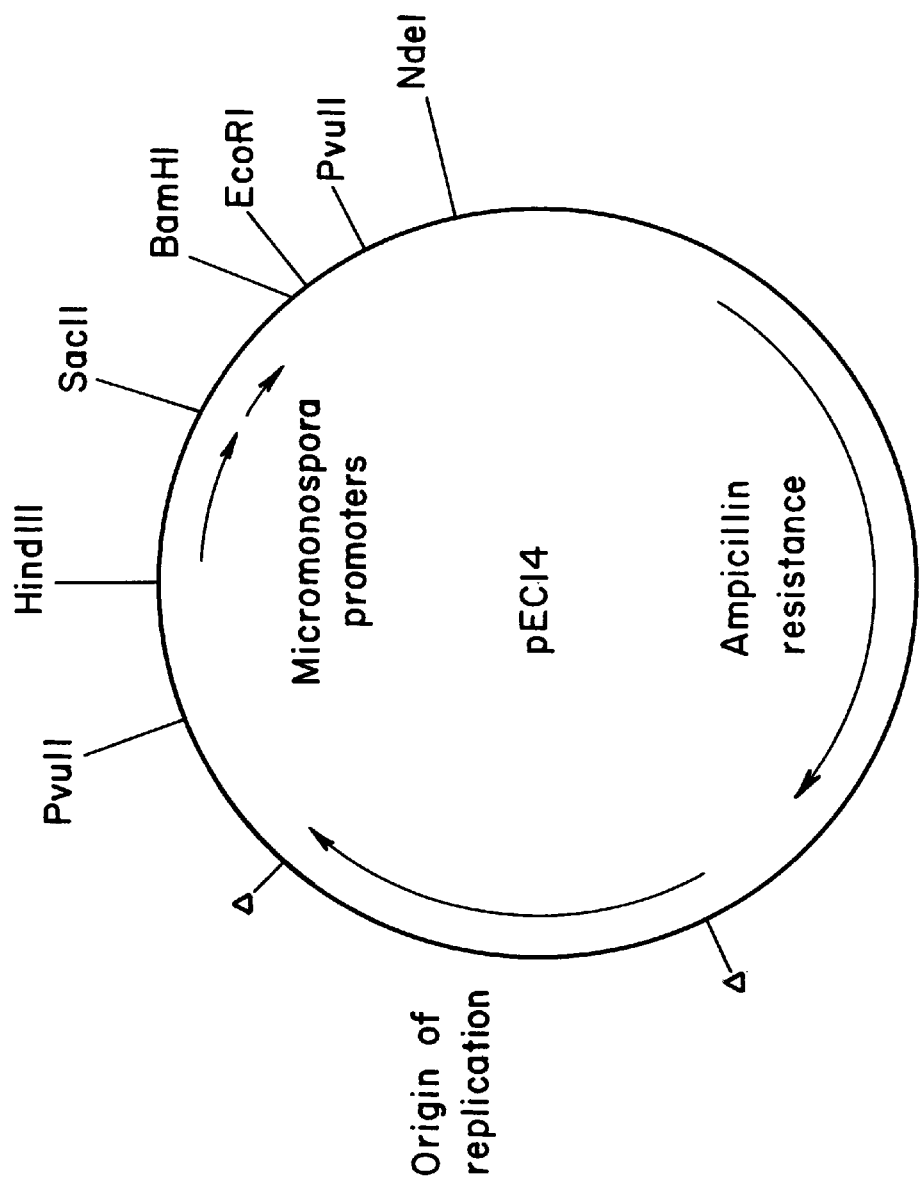

FIG. 17 is an illustration of the genetic map of pEC 14.

Figure 18A:
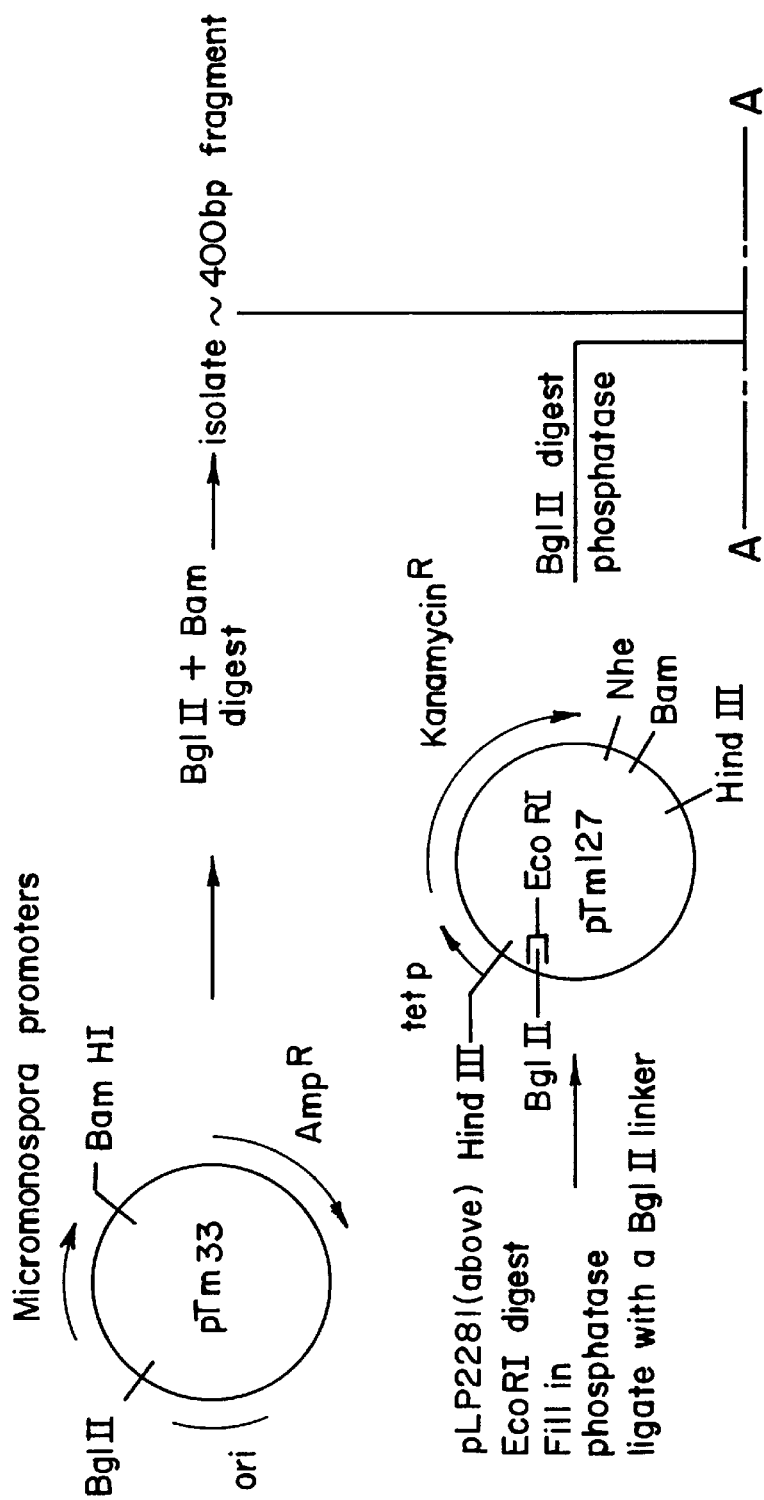
Figure 18B:
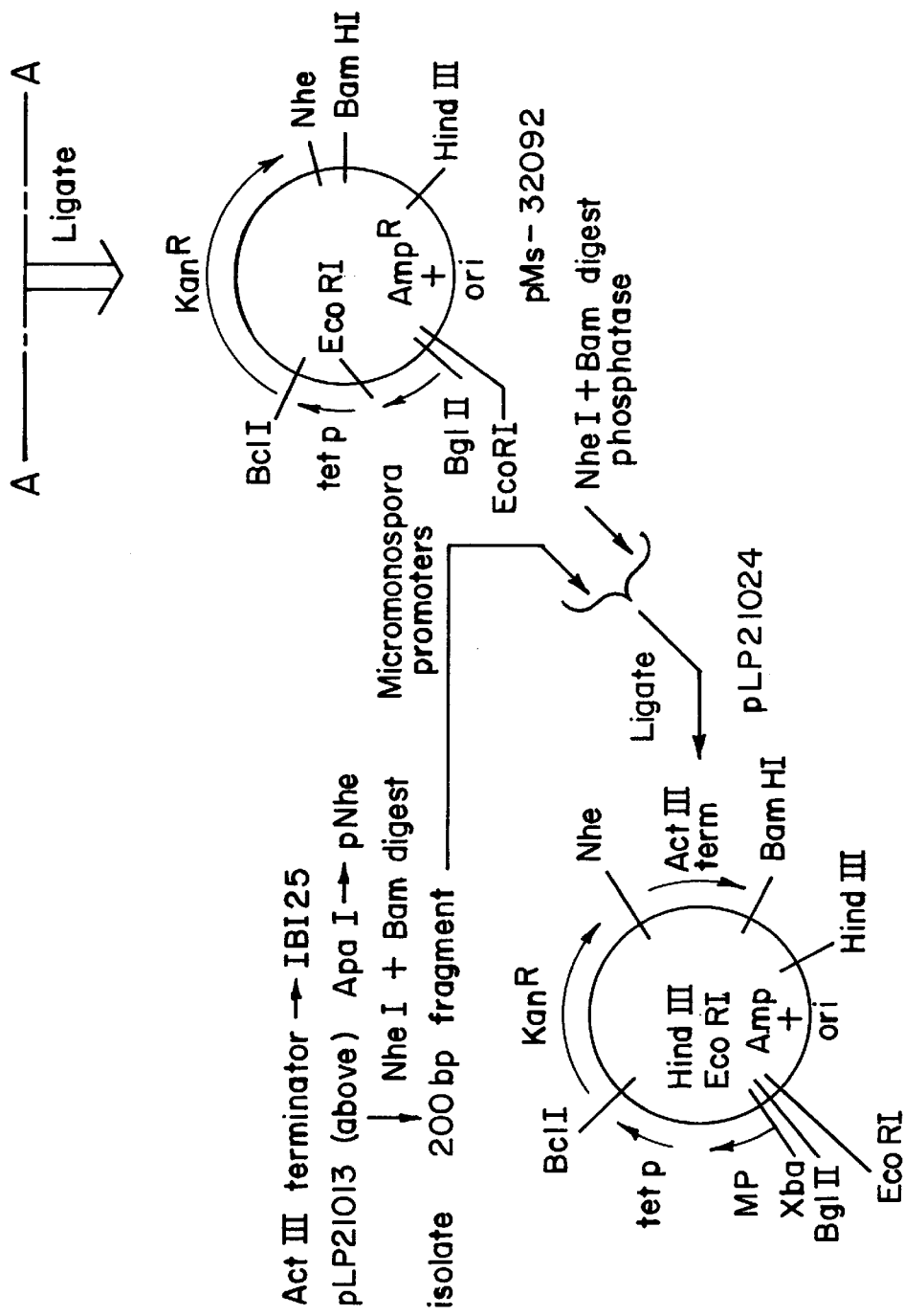

FIGS. 18A-18B are illustrations of the insertion of the kanamycin resistance gene to be functionally linked to both the *E. coli* promoter and the Micromonospora promoter.

Figure 19:
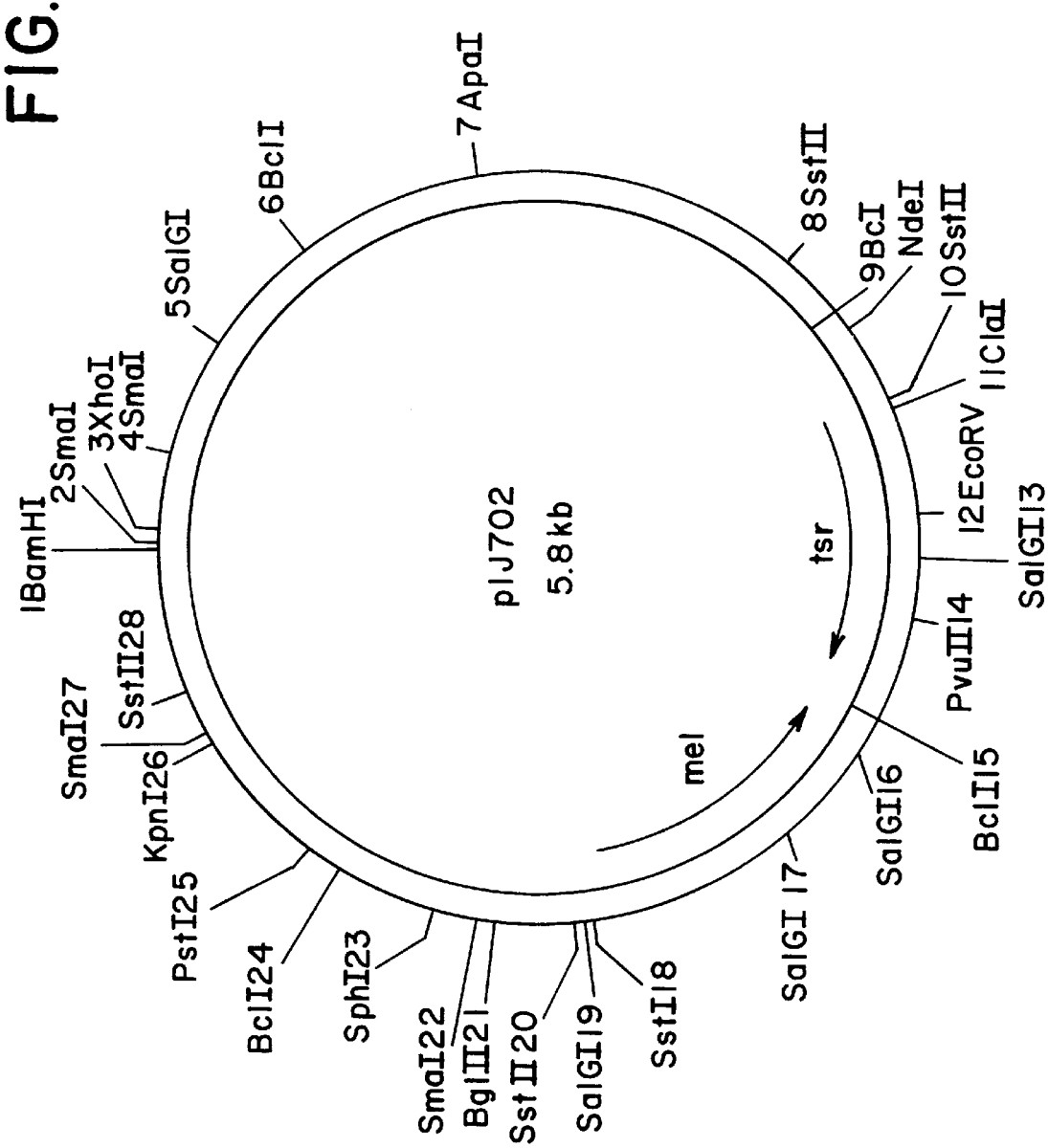

FIG. 19 is an illustration of the restriction map of plJ702.

Figure 20A:
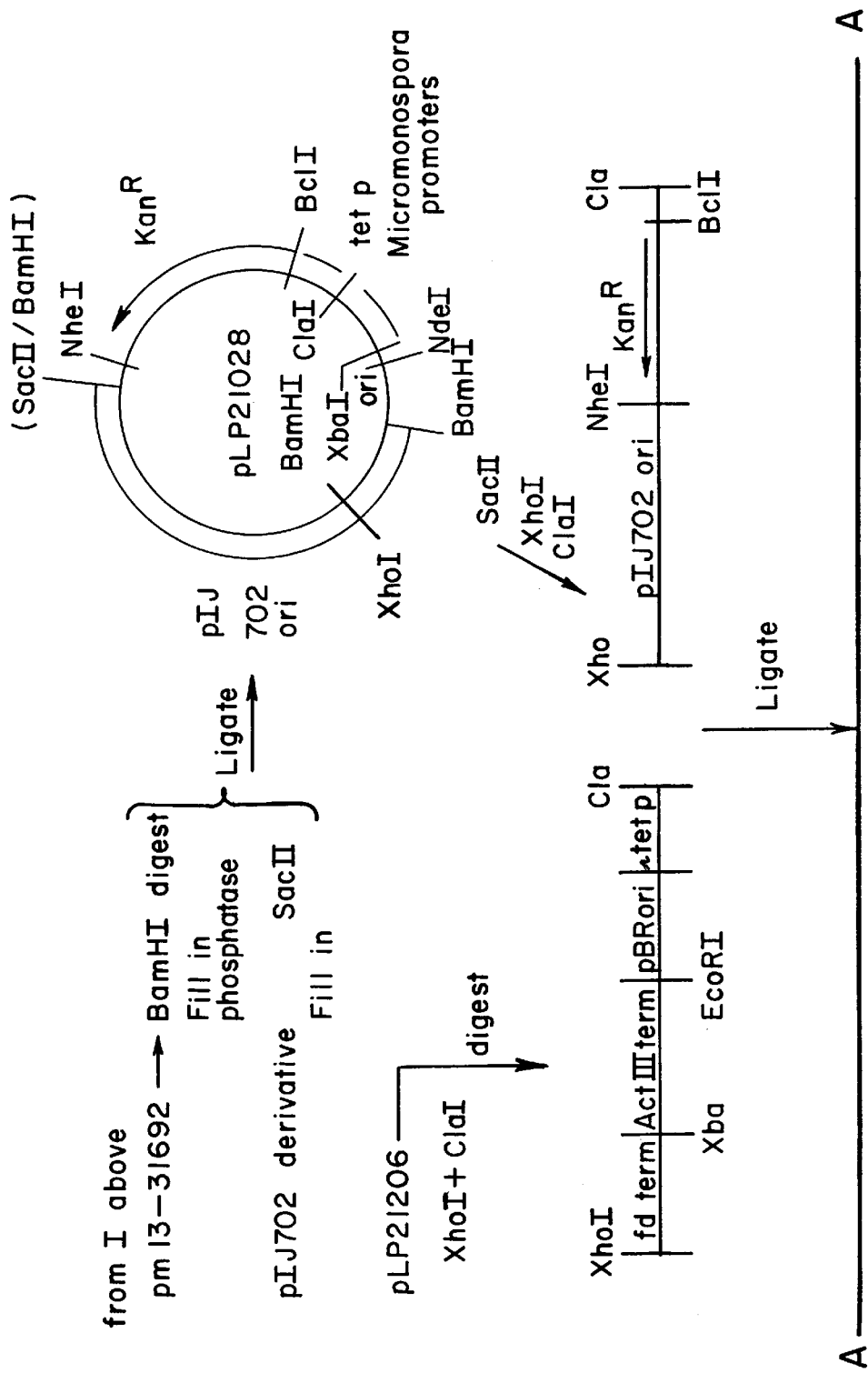
Figure 20B:
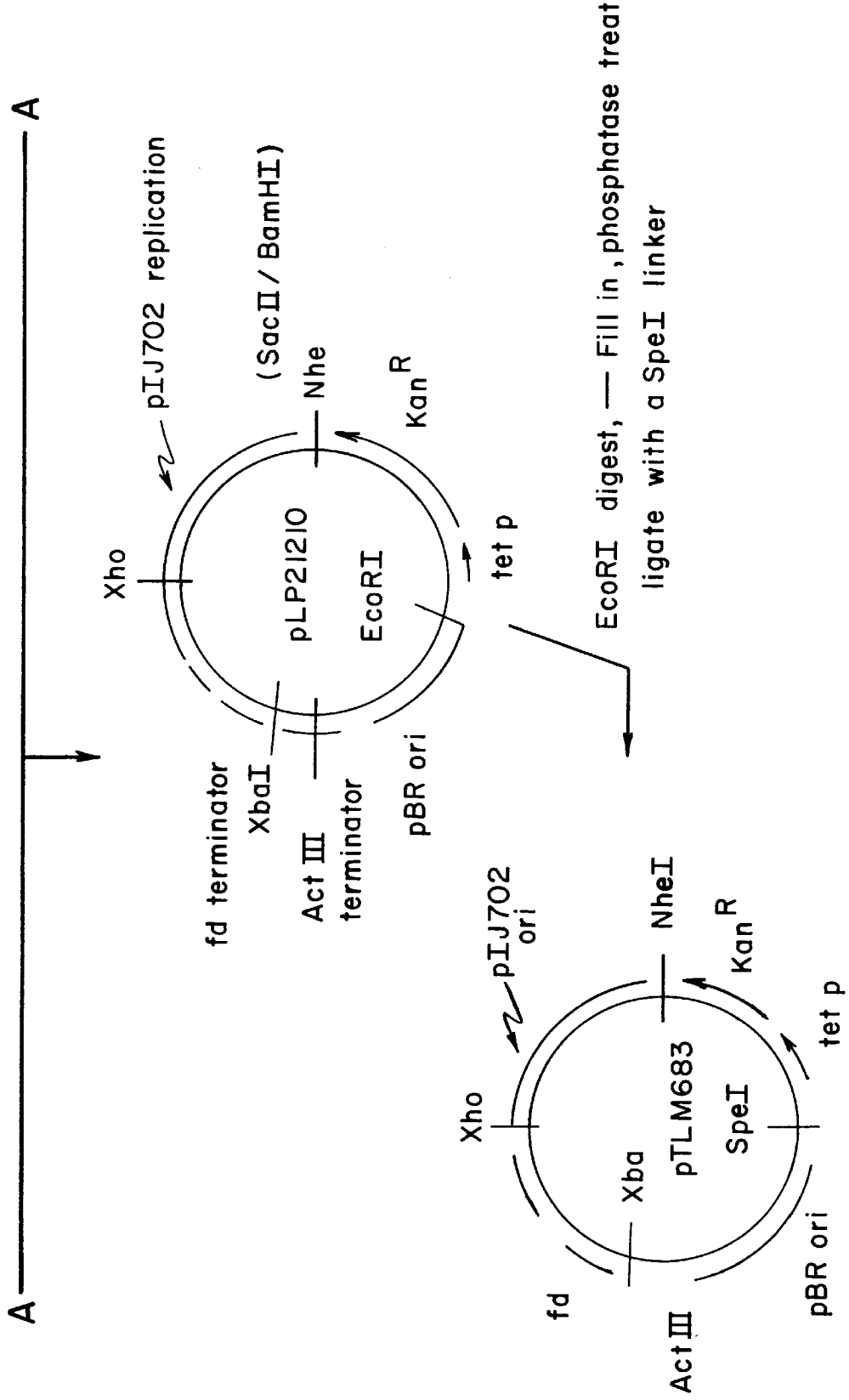

FIGS. 20A-20B are illustrations of the addition of the Streptomyces replication function to the vector under construction.

Figure 21:
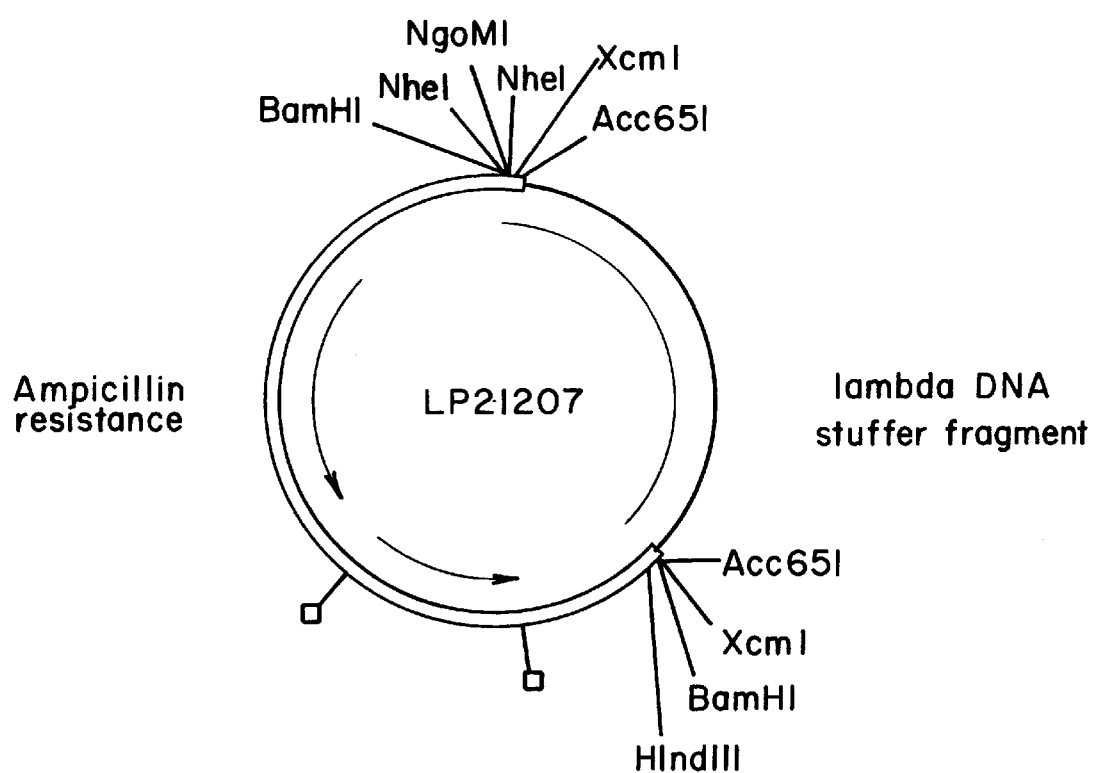

FIG. 21 is an illustration of the genetic map of pLP21207.

Figure 22:
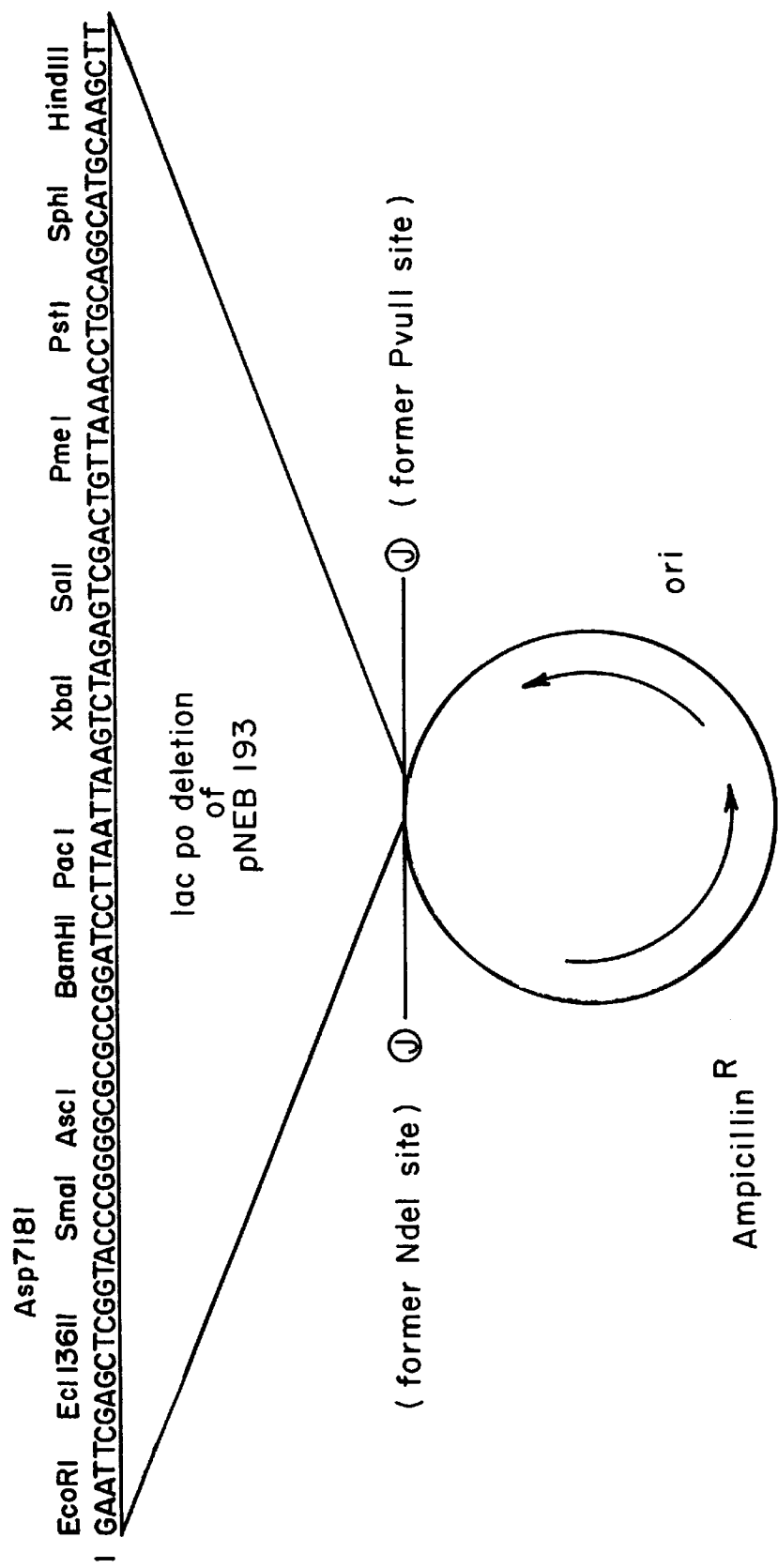
Figure 23:
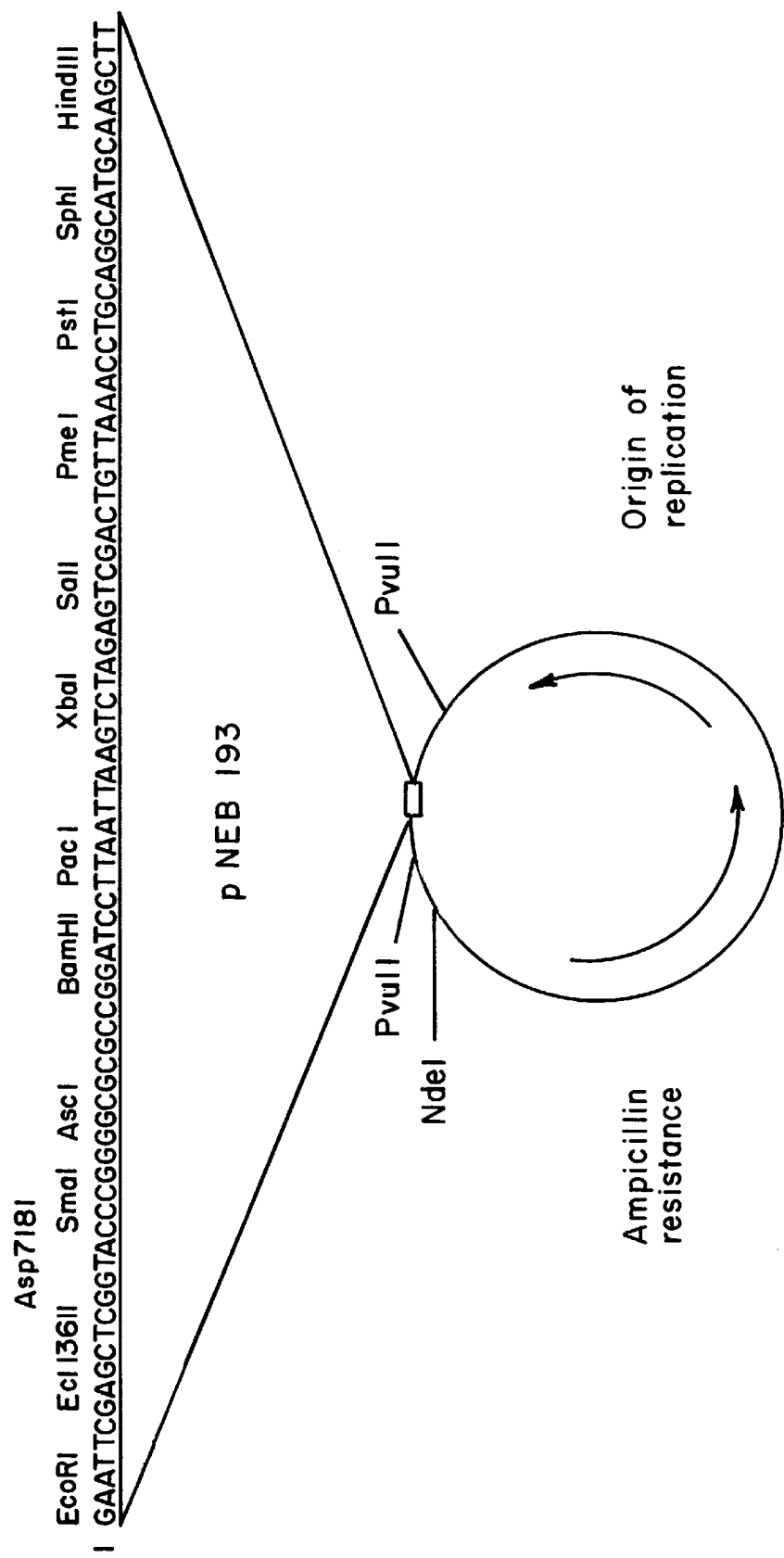

FIGS. 22 and 23 are illustrations of the genetic map of pNEB193.

Figure 24:
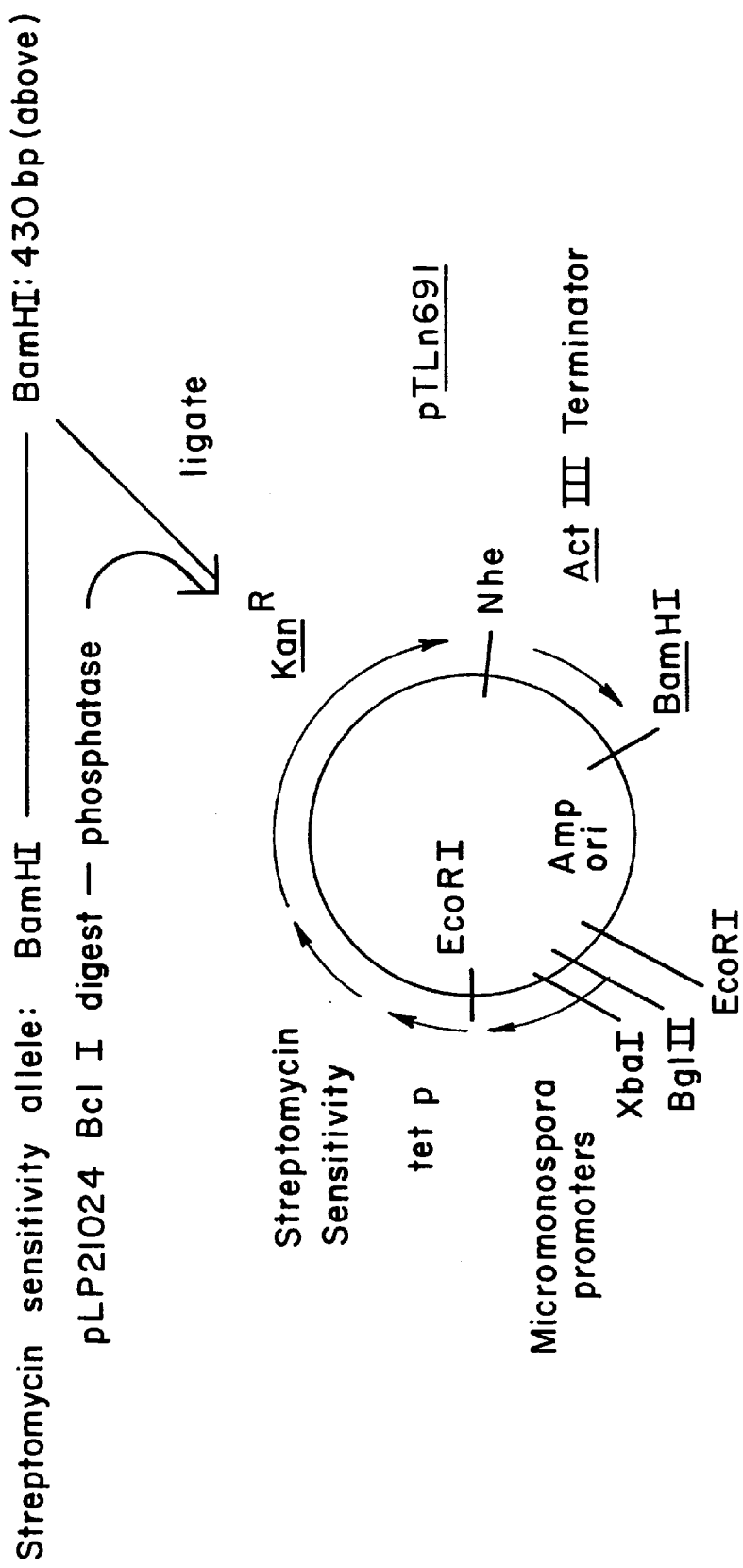

FIG. 24 is an illustration of the insertion of the streptomycin sensitivity gene into the vector under construction.

Figure 25:
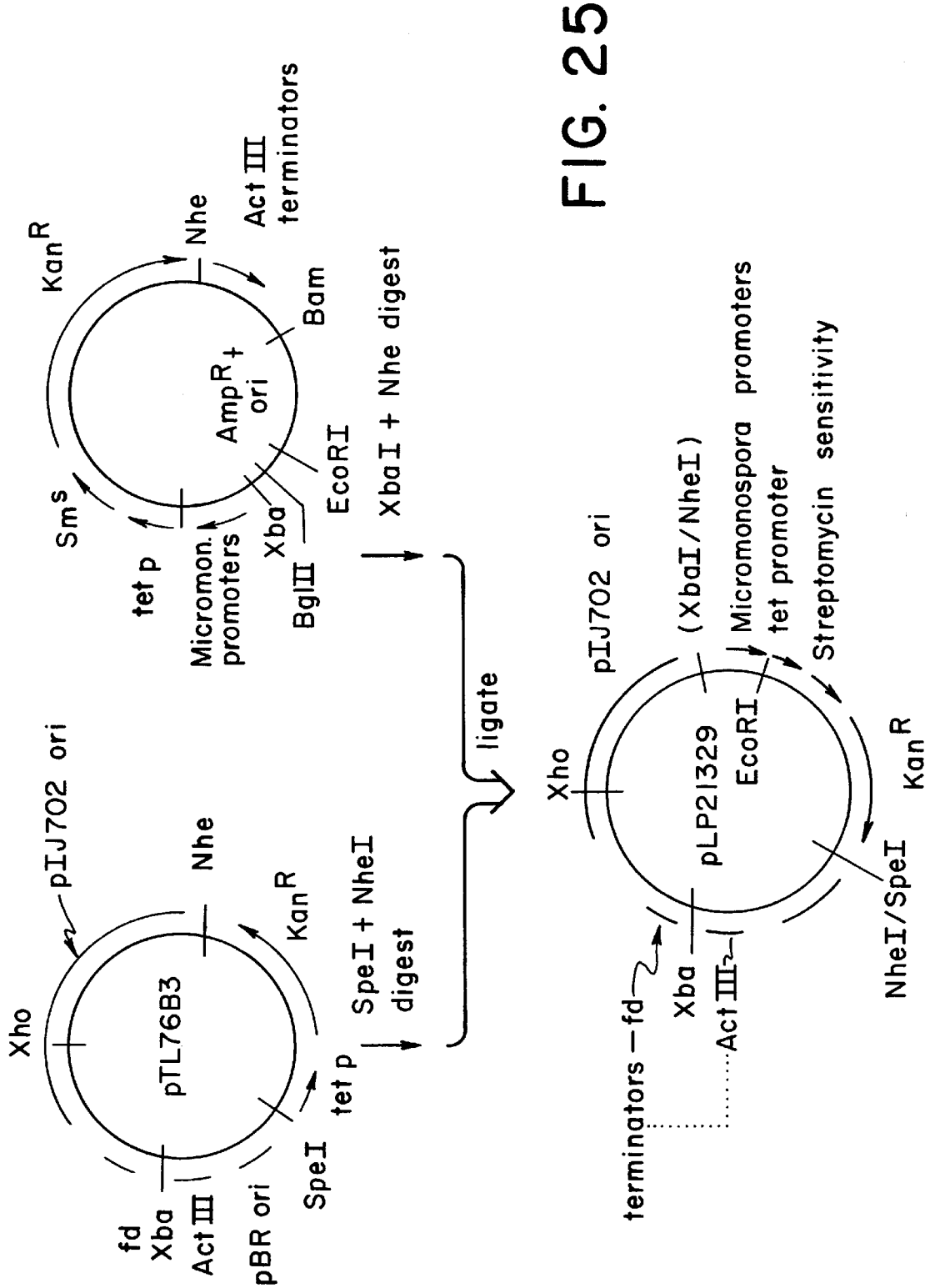

FIG. 25 is an illustration of the final assembly of pLP21329.

Figure 26:
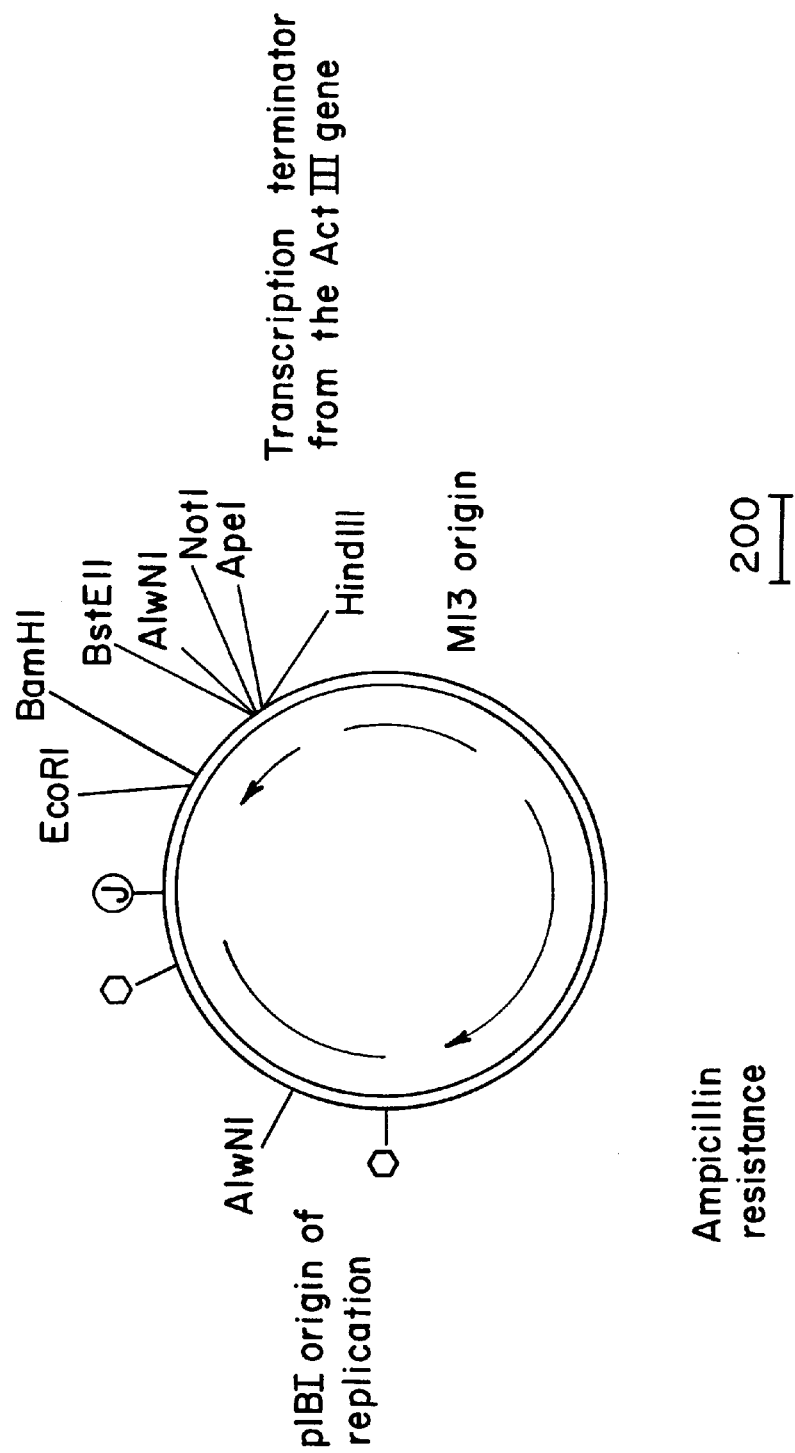

FIG. 26 is an illustration of the genetic map of plBI.

Figure 27:
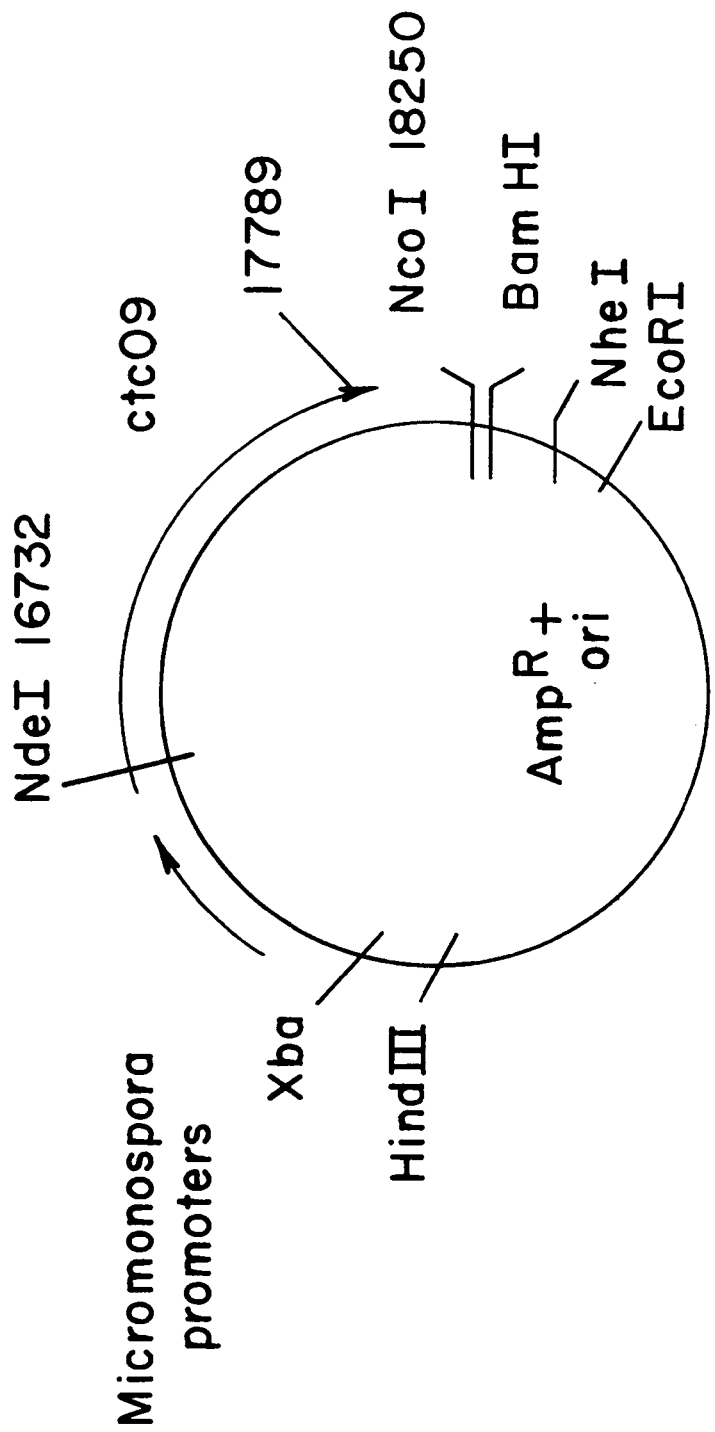

FIG. 27 is an illustration of a vector comprising CTC 09.

FIG. 28 is an illustration of a further subcloning of CTC 09.

Figure 29:
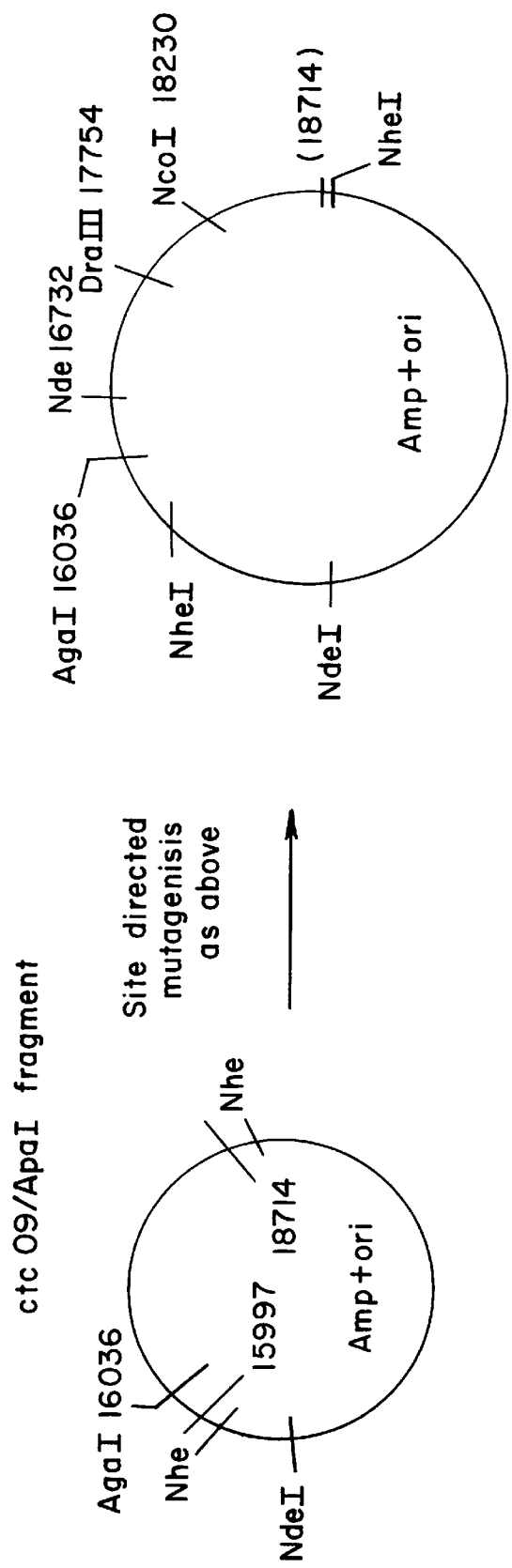

FIG. 29 is an illustration of the vectors which undergo site-directed mutagenesis for CTC 09.

Figure 30:
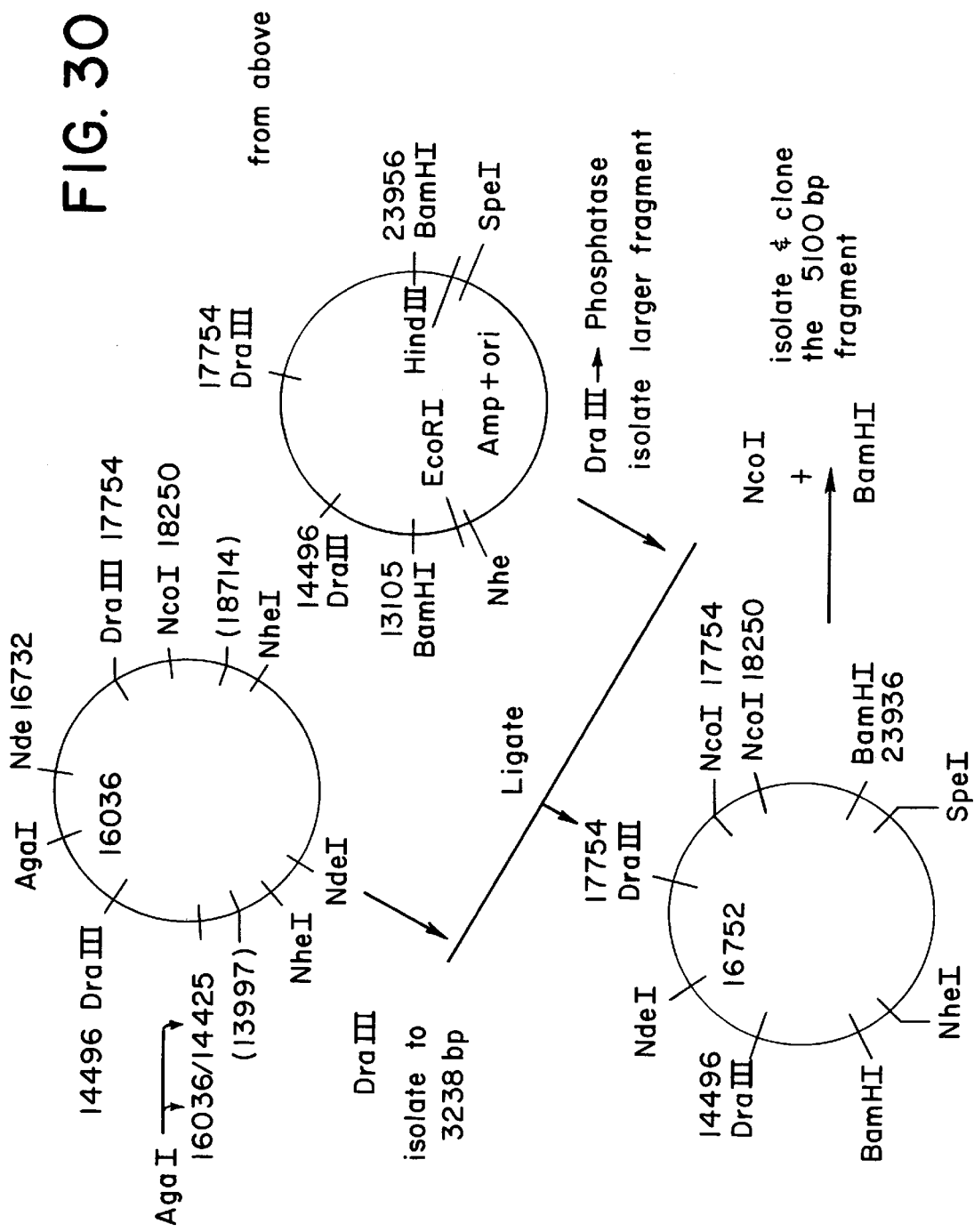

FIG. 30 is an illustration of the vectors used to clone a 5100 bp fragment of CTC 09.

Figure 31:
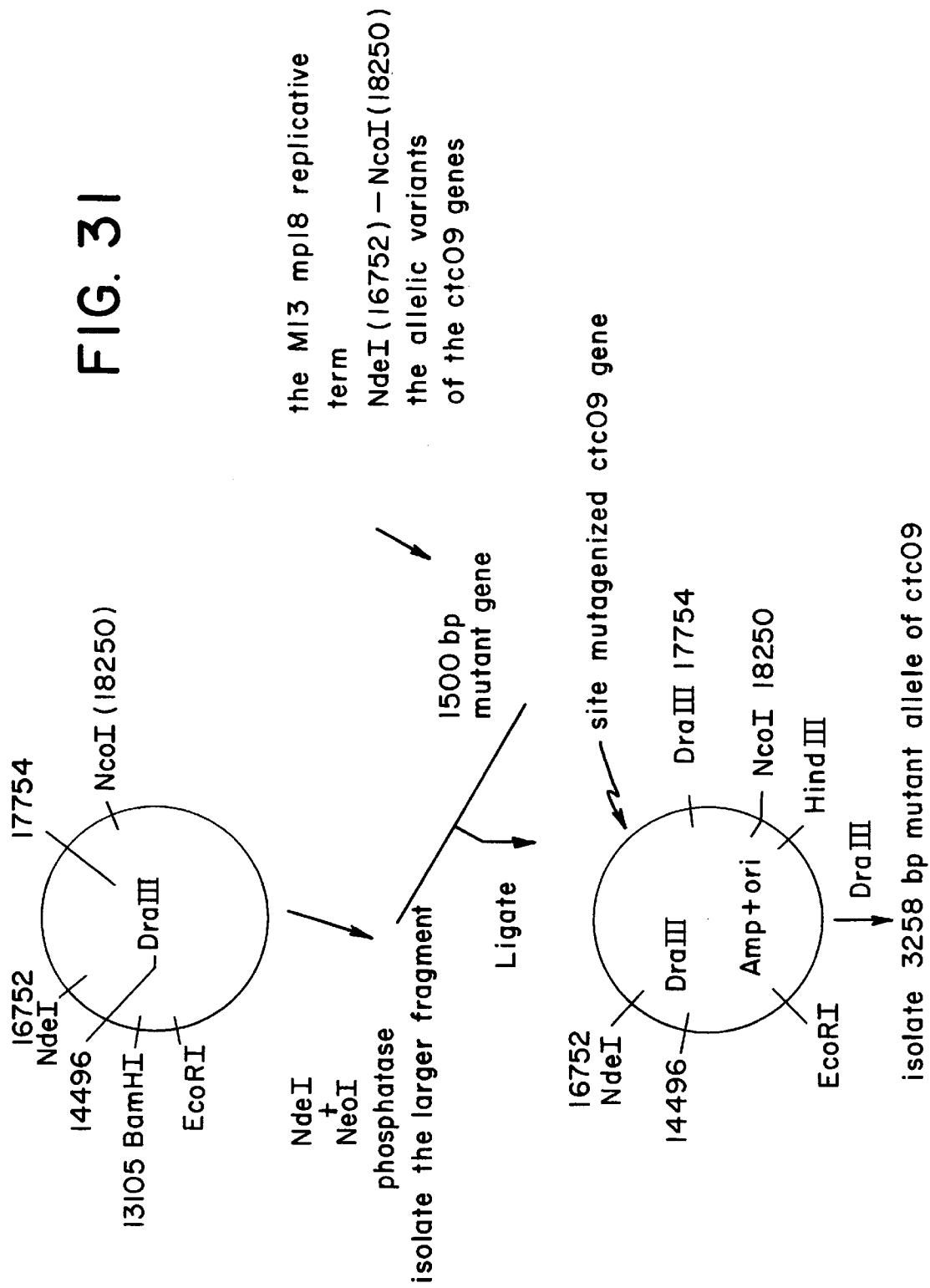

FIG. 31 is an illustration of the vectors used to construct a 3258 bp mutant allele of CTC 09.

Figure 32B:
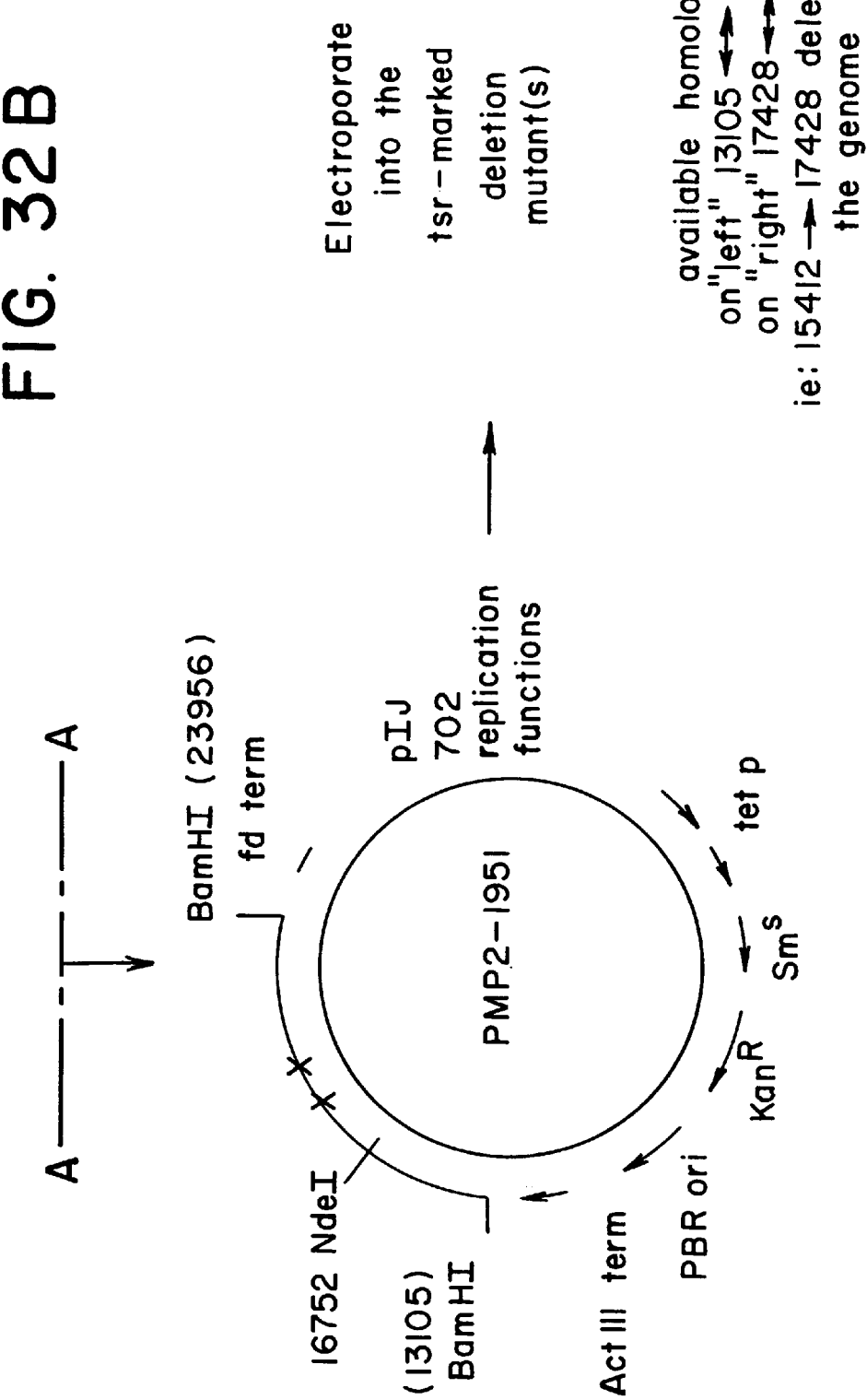

FIGS. 32A-32B are illustrations of the process for constructing the vector which is used to transform the recombinant alleles isolated after homologous recombination 1 (HR1) to perform homologous recombination (HR2).

SUMMARY OF THE INVENTION

Recombinant *S. aureofaciens* cells are provided. These cells comprise:
(a) at least one CTC 11 gene; and
(b) optionally
  (i) a CTC 09 gene;
  (ii) a CTC 03 gene; or
  (iii) a combination thereof;
  wherein:
  the CTC 11 gene is chromosomal, extra-chromosomal, or chromosomal and extra-chromosomal;
  the CTC 09 gene, CTC 03 gene, or a combination thereof is chromosomal, extra-chromosomal, or a combination thereof;
  expression of the CTC 11 gene is enhanced over that of a wild-type *S. aureofaciens* cell; and
  optionally, the CTC 09 gene, the CTC 03 gene, or both of the CTC 09 gene and the CTC 03 gene are inactivated.

Specific recombinant *S. aureofaciens* cells are also provided. These cells comprise (A)(a) at least one CTC 11 gene;
  wherein:
  the CTC 11 gene is chromosomal; and
  expression of the CTC 11 gene is enhanced over that of a wild-type *S. aureofaciens* cell;
(B)(a) at least one CTC 11 gene;
  wherein:
  the CTC 11 gene is extra-chromosomal; and
  expression of the CTC 11 gene is enhanced over that of a wild-type *S. aureofaciens* cell;
(C)(a) a CTC 03 gene;
  wherein:
  the CTC 03 gene is extra-chromosomal; and
  the CTC 03 gene is inactivated;
(D)(a) at least one CTC 11 gene; and
  (b) a CTC 09 gene;
  wherein:
  the CTC 11 gene is extra-chromosomal;
  the CTC 09 gene is chromosomal;
  expression of the CTC 11 gene is enhanced over that of a wild-type *S. aureofaciens* cell; and
  the CTC 09 gene is inactivated; or
(E)(a) at least two CTC 03 genes;
  wherein:
  one of the CTC 03 genes is chromosomal and one of the CTC 03 genes is extra-chromosomal; and
  the chromosomal CTC 03 gene and the extra-chromosomal CTC 03 gene are inactivated.

The present invention also contemplates vector pLP21329 and vectors for allelic replacement in a *S. aureofaciens* host cell. The vectors comprise:

(a) a functional *E. coli* origin of replication;
(b) a functional Streptomyces origin of replication;
(c) a functional gene that imparts a positively selectable phenotype on the host cell; and
(d) a ribosomal S12 gene which is expressed in Streptomyces such that it imparts sensitivity to streptomycin to the host cell.

In another embodiment, a method of mutating a target gene of a biosynthetic pathway of Streptornyces is disclosed. The method comprises (a) replacing the genomic copy of the target gene with a selectable marker gene through homologous recombination to form a first recombinant strain; and
(b) replacing the selectable marker gene in the first recombinant strain with an altered copy of the target gene through homologous recombination to form a second recombinant strain.

DETAILED DESCRIPTION OF THE INVENTION

Tetracycline and Tetracycline Derivatives

Tetracycline and certain derivatives can be represented by the following formulae.

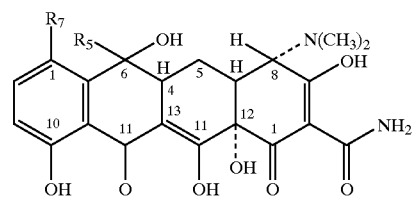

| | R6 | R7 |
|---|---|---|
| CHLORTETRACYCLINE | $CH_3$ | Cl |
| TETRACYCLINE | $CH_3$ | H |
| DEMETHYLCHLORTETRACYCLINE | H | Cl |
| DEMETHYTETRACYCLINE | H | H |

Any of these tetracycline compounds can be prepared, in increased yield, by the methods and strains of the present invention.

An additional tetracycline derivative, minocycline, has the formula

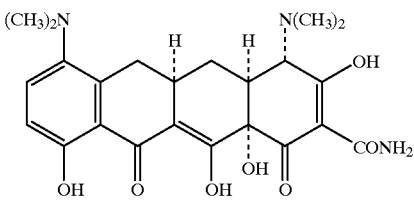

Minocycline is typically prepared synthetically from demethyltetracycline.

Biosynthetic Pathway of Tetracycline Compound Production

The biosynthetic pathway for the biosynthesis of chlortetracycline is illustrated in FIG. 1. This biosynthetic pathway can be adapted for use in the biosynthesis of other tetracycline compounds with appropriate methylation or chlorination included or omitted.

The isolation of genes for the biosynthetic pathway of chlortetracycline is described in U.S. patent application Ser. No. 08/125,468, filed Sep. 22, 1993, now U.S. Pat. No. 5,589,385. Briefly, a bifunctional cosmid vector system was used to create a representative S. aureofaciens DNA library. The library was transformed into a tetracycline sensitive host and transformants were screened for conversion to a tetracyline resistant phenotype. Organisms harboring the entire biosynthetic pathway for tetracycline are resistant to its effects, for the pathway includes genes encoding resistance to the produced antibiotic. Production of the tetracyclines from the plasmid Was confirmed for two positive transformants. Thus, the DNA contained in those vectors included all of the genes necessary for the production of tetracycline and its derivatives.

Figure 2:
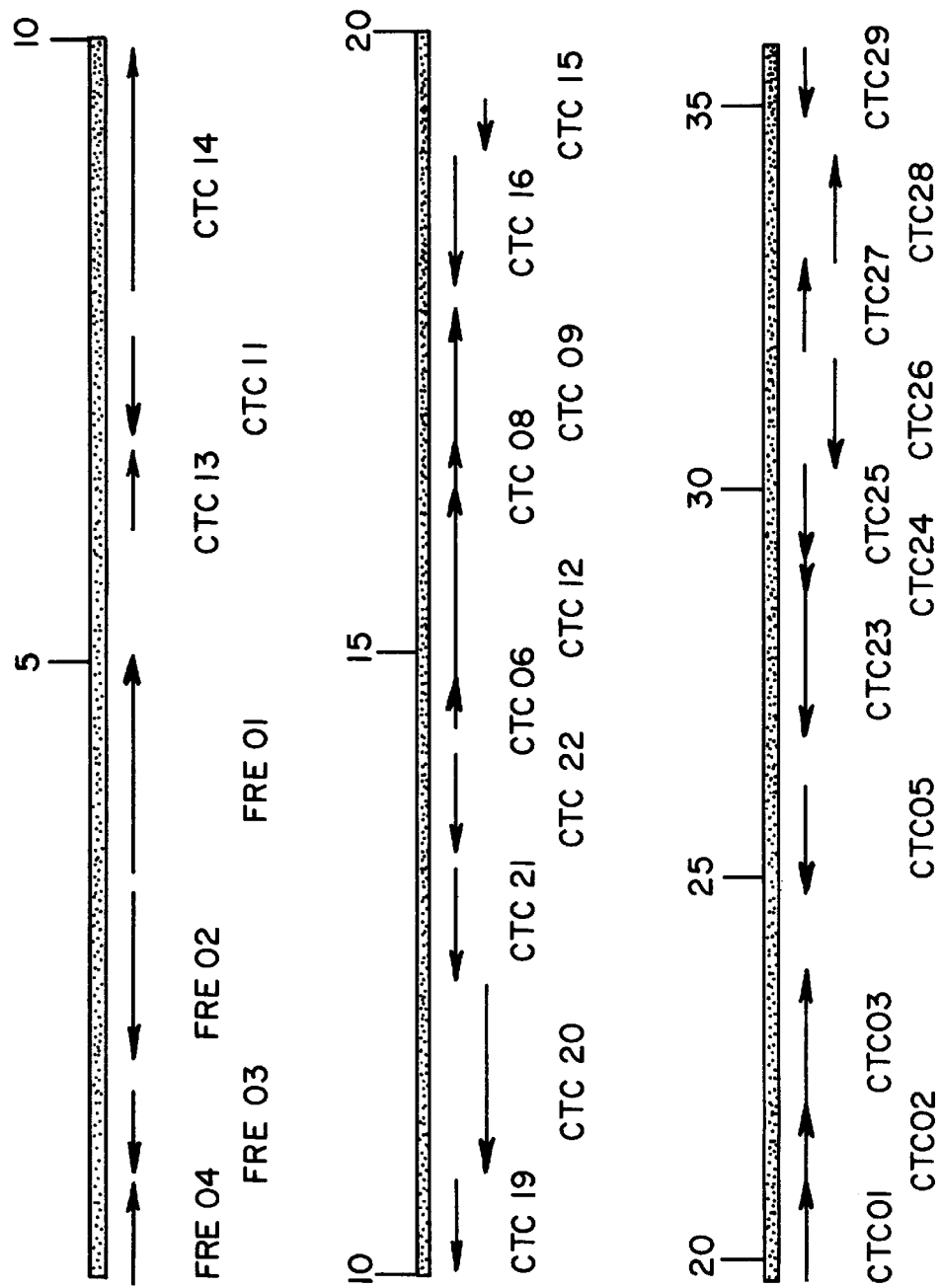
FIG. 2 is an illustration of a genetic map of the DNA fragment encoding the chlortetracycline biosynthetic pathway of *S. aureofaciens*. This map identifies the locations of the open reading frames, their genetic designations, and the direction of transcription.
Figure 3:
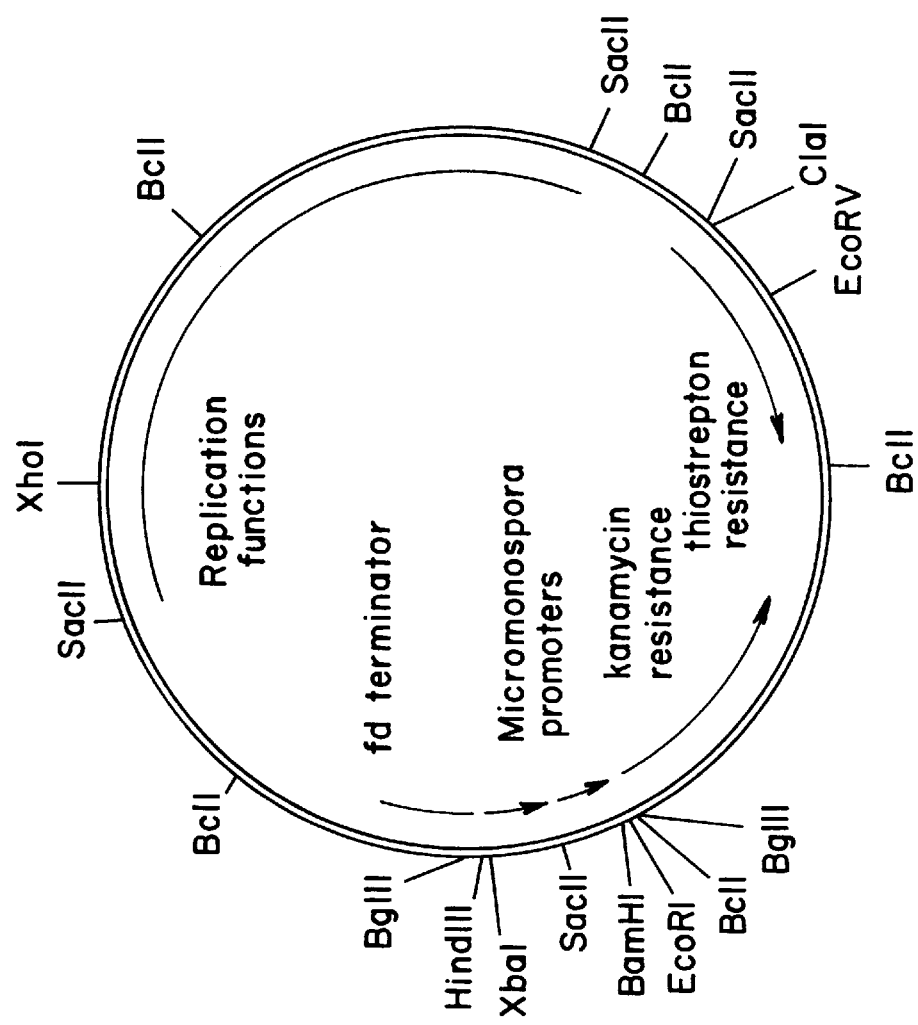
FIG. 3 is an illustration of a genetic map of pPP14 which was a source of the heterologous promoters derived from *Micromonopora echinospora* (MP).
Figure 4A:
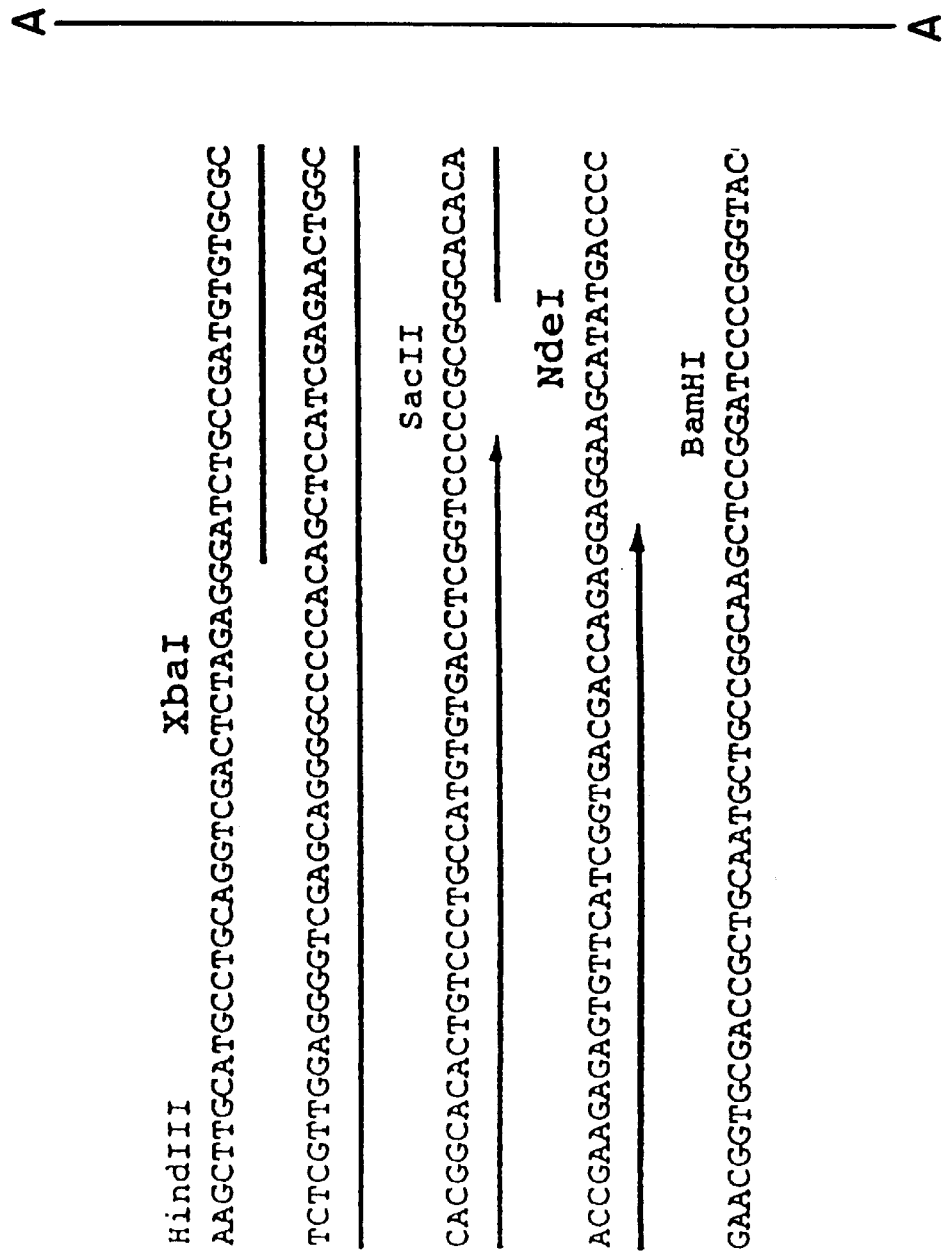
Figure 6:
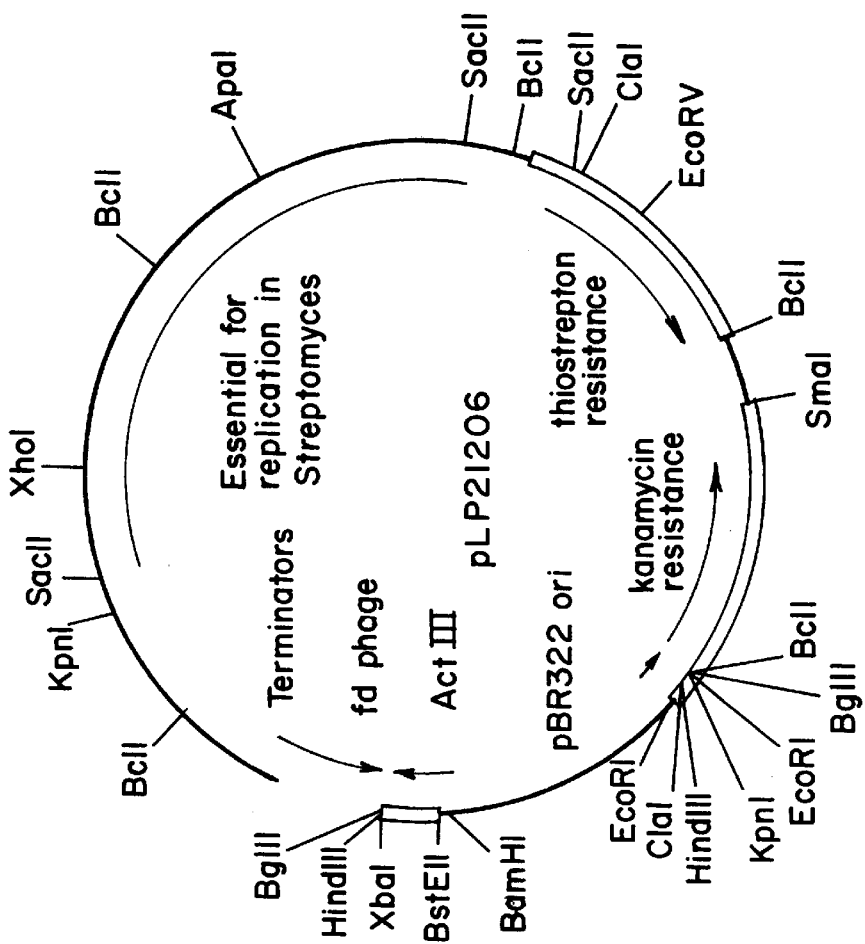
FIG. 6 is an illustration of a genetic map of pLP21206, an expression vector in which the fragments constructed in pLP21281 were inserted at the XbaI cloning site. The constucts were transformed into wild-type and mutant host cells to assay the effect of the translated protein on the cells.
Figure 5:
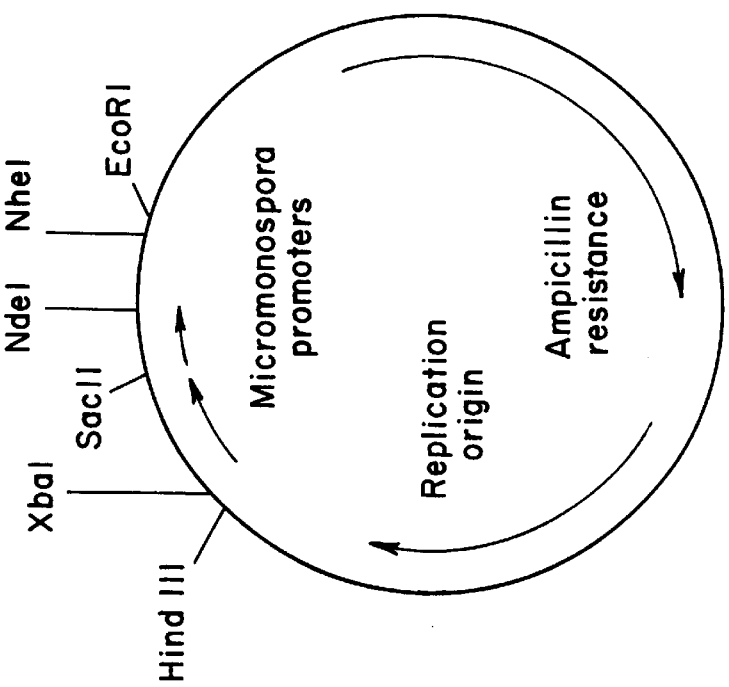
FIG. 5 is an illustration of a genetic map of pLP21281 in which constructs were made which functionally linked the MP with the putative genes of the chlortetracycline biosynthetic pathway.
Figure 7A:
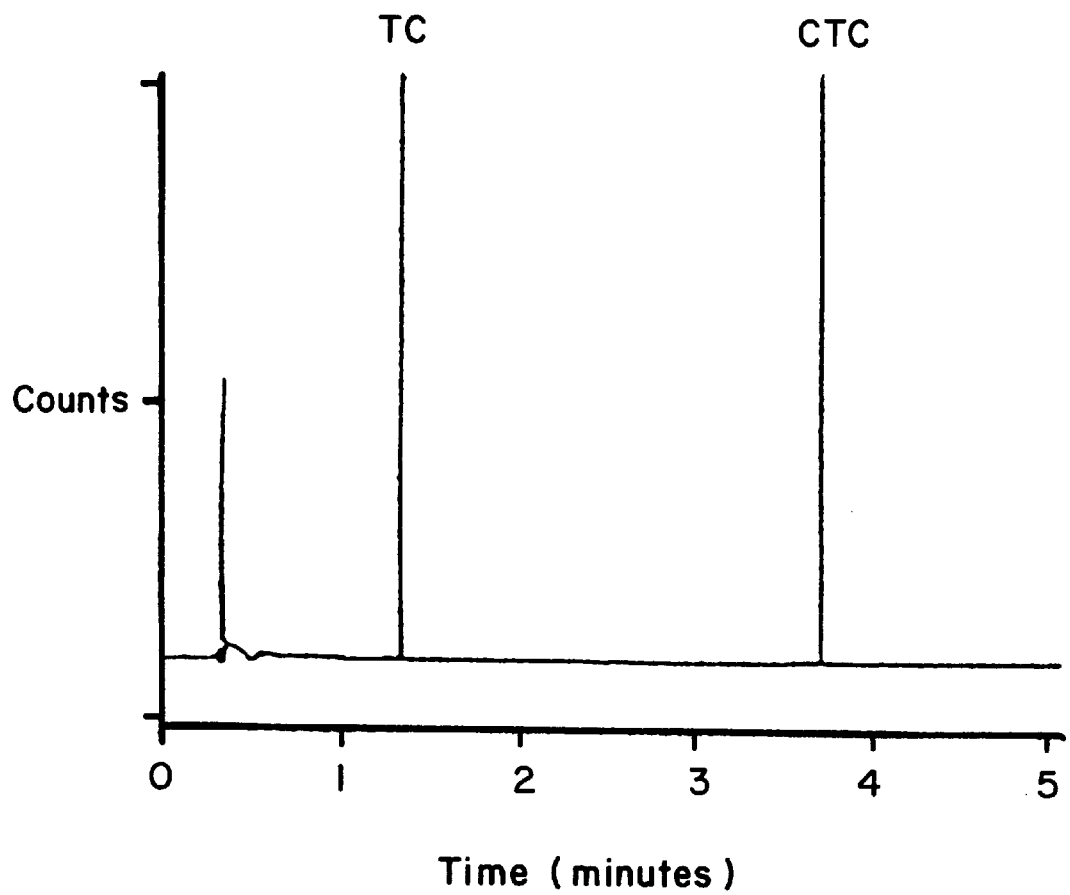
FIGS. 7A–7C are illustrations of an HPLC graph of the products of a control culture (left panel) and the products produced when CTC 11 is expressed from pLP21206 in a wildtype host (middle panel, one copy and right panel, two copies). Note that the effect seen is dose dependent as two copies increases chlortetracycline production approximately twice as much as does one copy.
Figure 7B:
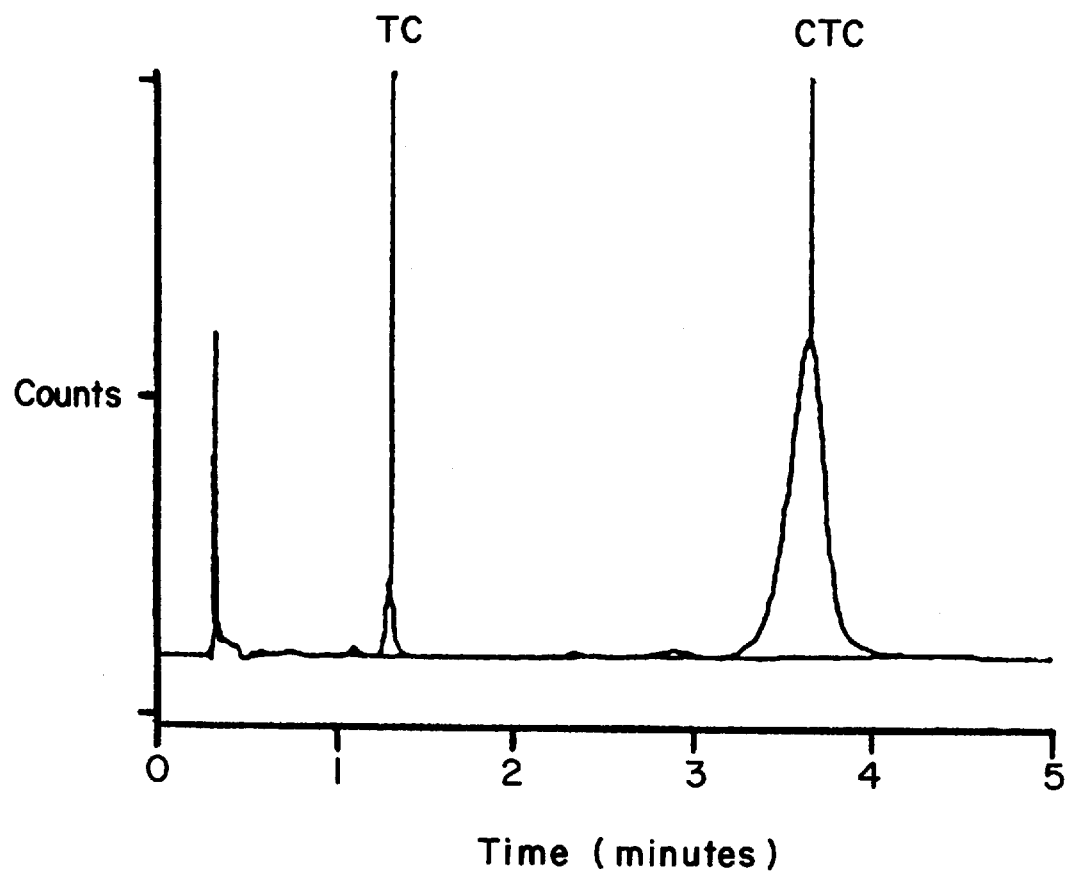
Figure 7C:
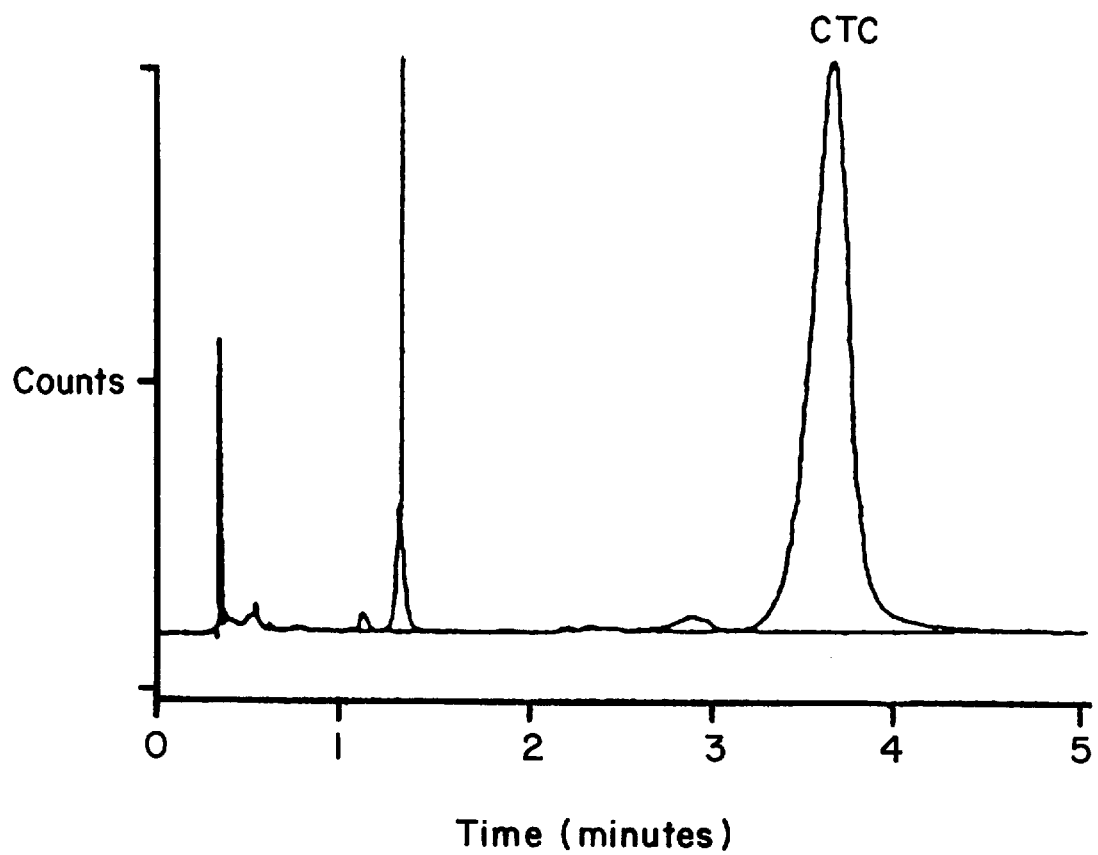

The DNA was isolated and sequenced, yielding 30,000 bp, and subsequent investigation has sequenced an additional 5,801 upstream bp. Open reading frames were identified. FIG. 2 is a diagram of a genetic map of the region setting out the tentative gene locations and directions of transcription for each gene. Using sequence homology, tentative functions of the open reading frames were identified. Open reading frames are identified in Table 2 below. Putative genes must be transcribed and translated at a level which is sufficient to assay the effect of the protein on the host. To achieve this, each open reading frame was expressed in wild-type cells under the control of heterologous promoters contained on a 400 bp fragment of *Micromonospora echinospora*. This fragment carries at least three promoters and is transcriptionally active in *Streptomyces lividans* during vegetative growth as well as during secondary metabolism (Baum et al. *J. Bact.* 170:71–77, 1988). This fragment was isolated from plasmid pPP14 (see FIG. 3 and FIG. 4) and was placed in vector pLP21281 (see FIG. 5). Fragments including CTC 09 and/or CTC 03 under the control of the heterologous promoters were cloned into the final expression vector, pLP21206 (FIG. 6), which was transformed into the host, chlortetracycline producing *S. aureofaciens* strain A377. For open reading frame CTC 11, a dose-specific increase in chlortetracycline titer was noted (see FIG. 7). This gene was tentatively assigned the function of transcriptional activators.

Further functional assignments were supported by complementation analysis using mutant strains which are blocked at particular steps in the biosynthetic pathway. Briefly, complementation analysis involves the expression of cloned pieces of DNA on extrachromosomal vectors transformed into the mutant hosts. If the expression of the cloned DNA results in "unblocking" the mutation, i.e., production of the biosynthetic product by the transformed mutant, the cloned DNA is said to "complement" the mutation present in the host. As the host mutations have been generally well-characterized and the biochemical function which is dysfunctional is often known, functions can be assigned to the genes encoded on the complementing DNA fragment. Complementation combined with sequence homology provides strong evidence for the function of the products of a particular genomic fragment.

Figure 8A:
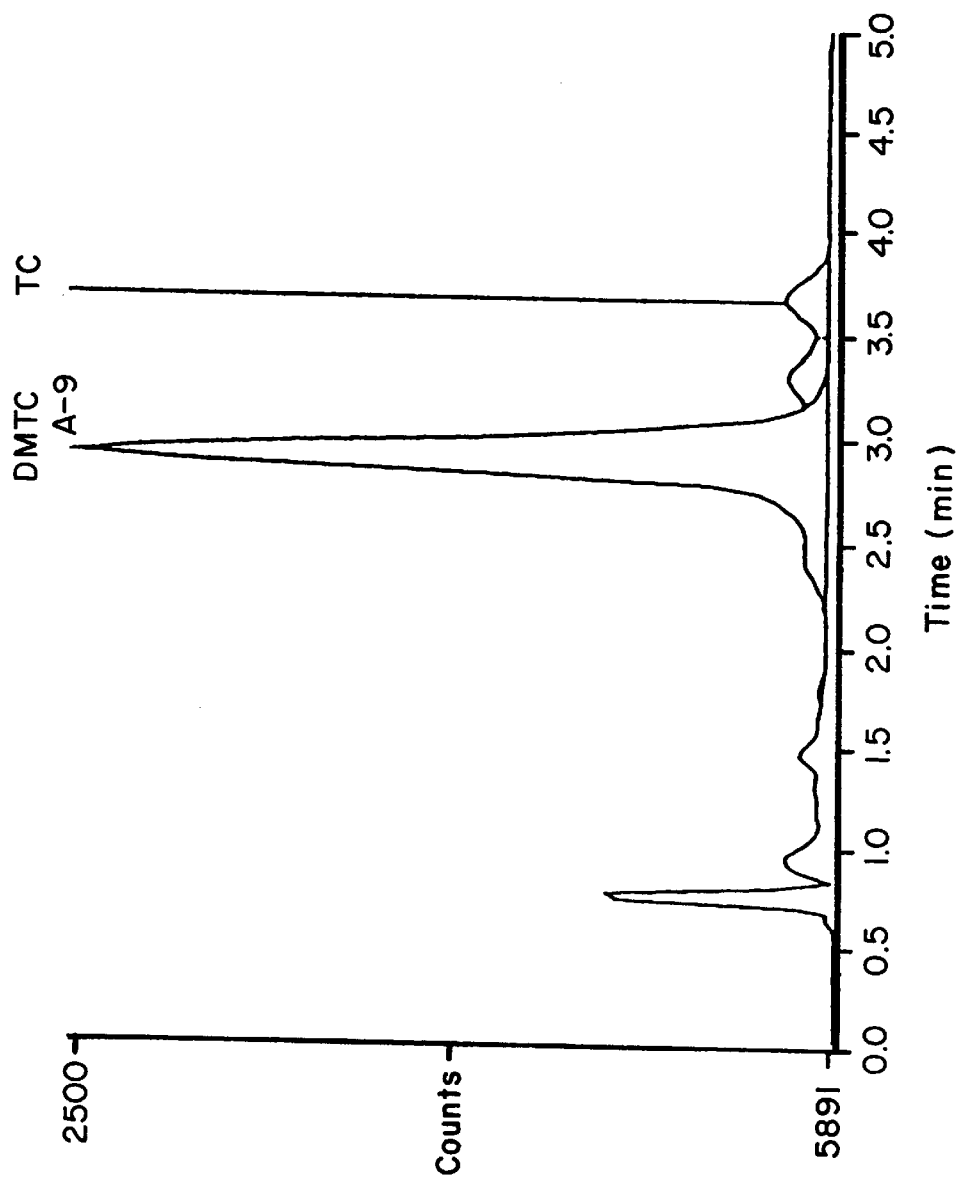
FIGS. 8A-8B are illustrations of HPLC graphs of the products of a control culture (left panel) and the products produced when CTC 09 is expressed from pLP21206 in a 6-demethyl tetracycline (DMTC) producing host (right panel).
Figure 8B:
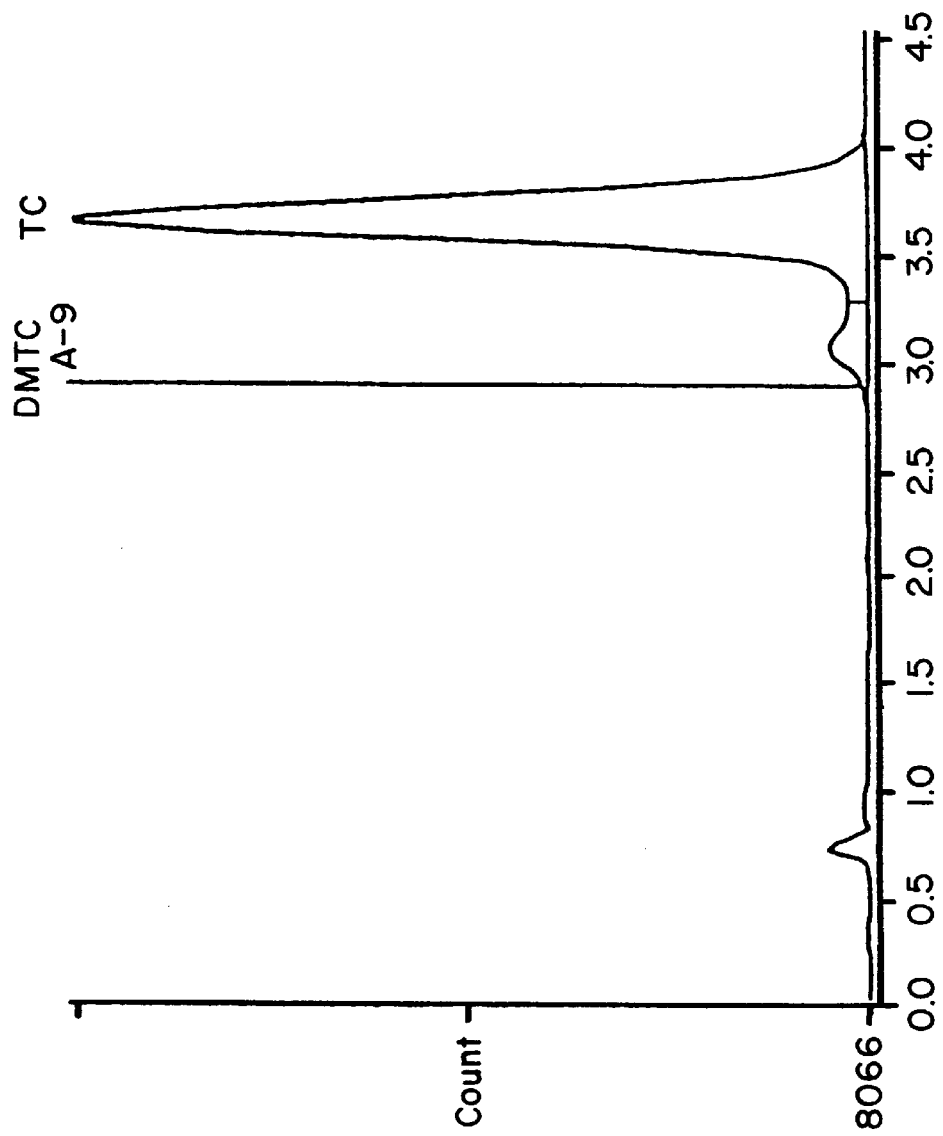

Specifically, CTC 09, was expressed from pLP21206 in a S. aureofaciens strain which produces 6-demethyl tetracycline (see FIG. 8). This expression unblocked the mutation and allowed the mutant strain to produce tetracycline (see FIG. 8). Thus, it was concluded that CTC 09 encodes the enzyme responsible for the methylation of C-6. CTC 03, was expressed from pLP21206 in S. aureofaciens strain T377 which produces tetracycline (see FIG. 9). The expression of this gene resulted in the ability of the mutant strain to produce chlortetracycline (see FIG. 9). Thus, it was concluded that CTC 03 encodes the enzyme responsible for chlorination at C-7.

TABLE 2

Open Reading Frames of the Chlortetracycline Biosynthetic Pathway in S. aureofaciens

| Open Reading Frames | Assigned Function in Biosynthetic Pathway | FIG. 1 step #s |
|---|---|---|
| FRE 02 | Glutamine synthetase | |
| FRE 01 | Homologue of the Rhodobacter adgA gene | |
| CTC 11 | Transcription activation | |
| CTC 14 | Ribosomal tetracycline resistance | |
| CTC 20 | C-12a-hydroxylation | step 3 |
| CTC 21 | Polyketide cyclase-dehydratase | |
| CTC 22 | Beta-keto reductase | |
| CTC 12 | Ring closure (?) | step 2 |
| CTC 08 | (?) | |
| CTC 09 | Methylation of the C-6 position | step 1 |
| CTC 01 | Hydroxylation of the C-6 position | step 7 |
| CTC 02 | Dimethylation of the C-4 amine | step 6 |
| CTC 03 | Chlorination of the C-7 position | step 4 |
| CTC 05 | Tetracycline resistance (export) | |
| CTC 23 | Homologous to asparagine synthetases - presumably involved in providing the malonamyl CoA starting unit | |
| CTC 24 | Acyl carrier protein | |
| CTC 25 | Polyketide condensing enzyme "ORF 2" | |
| CTC 26 | Polyketide condensing enzyme "ORF 1" | |

Genetically altered S. aureofaciens

The present inventors manipulated the genes involved in the biosynthetic pathway for the production of tetracycline compounds in order to construct genetically altered strains of S. aureofaciens which produce the desired tetracycline products, preferably in increased yields.

The genetically engineered microorganisms of the present invention produce tetracycline-based compounds. This can be accomplished by increasing the expression of one or more of the genes involved in the biosynthetic pathway for the production of the desired tetracycline compound and/or by suppressing or eliminating (inactivating) the expression of one or more of the genes involved in the biosynthetic pathway(s). The microorganisms can be altered at the chromosomal level by homologous recombination techniques, by transformation and growth with an autonomously replictating cytoplasmic plasmid, or by a combination thereof.

Target Genes

The genetically altered microorganisms of the present invention are prepared by methods that utilize homologous recombination to replace with an altered allele the genomic copy of any of three genes or any combination thereof involved in the biosynthetic pathway. Specific genes of interest are CTC 11 which regulates the amount of product produced, gene CTC 09 which results in methylation of the tetracycline compounds, and gene CTC 03 which results in chlorination of the tetracycline compound, or one or more desired mutant forms of any of these genes.

Transcription and Activator Gene CTC 11

CTC 11 is a putative transcription activator, and thus, its expression can be manipulated to increase the level of production of tetracycline compounds. Three methods of increasing expression were utilized for CTC 11.

Firstly, the CTC 11 gene was placed under the control of the promoter fragment from Micromonspora. Secondly, the orientation of the gene on the chromosome was changed, as the direction of transcription within the chromosome can alter RNA levels.

Finally, two rare codons were changed to those more commonly utilized by *S. aureofaciens*. The codon usage for Streptomyces is known and can be deduced from the sequence disclosed in U.S. patent application Ser. No. 08/125,468, and protein production can be increased by alteration of the third nucleotide of a rare codon to yield a more common codon for that amino acid.

The expression of CTC 11 is typically increased in the present invention by transforming a host cell with a plasmid that includes one or more copies of the gene. Transformation is performed by electroporation as described below in Example 3, and further, can be performed by methods well known in the art.

Enzymatic Activity Genes—CTC 09 (methylation) and CTC 03 (chlorination)

According to the present invention, *S. aureofaciens* may be manipulated to eliminate expression of the one or more genes which are not needed to produce a tetracycline product. For example, to produce a demethylated, non-chlorinated product such as 6-demethyl tetracycline, it is desirable to reduce or eliminate (i.e., inactivate) the enzymatic activity of the gene responsible for the methylation of the C-6 position (CTC 09) and the gene responsible for the chlorination of the C-7 position (CTC 03).

Homologous Recombination to Selectively Eliminate Gene Function

The process of producing the recombinant strains of the present invention occurs in two general stages. First, the genomic form of the gene or genes is replaced with a gene or genes which function as a selectable marker. Second, selectable marker is exchanged with an altered allele of the gene, whether it be a complete deletion or a copy which has been altered through site-directed mutagenesis.

Specifically, the genetically altered microorganisms of the present invention can be prepared by the following procedures.

(1) Construction of hybrid DNA fragment including selectable marker at target gene chromosomal location Once it is determined which gene or genes of the biosynthetic pathway are to be altered, a DNA fragment including the target gene plus flanking sequence is isolated. Preferably, the target gene should be flanked by over 2 kilobases of sequence on either side. The amount of flanking sequence is limited by the amount of total insert which can be carried by the vector to be used in the subsequent steps.

For example, in a preferred embodiment of the present invention, fragments including CTC 11, CTC 09, or CTC 03 and approximately 2 kb sequences flanking both upstream and downstream are isolated from the gene cluster encoding the chlortetracycline biosynthetic pathway.

The target gene is deleted and is replaced with a gene which imparts a selectable phenotype. This deletion should encompass not only sequences encoding the target gene but also sequences of the flanking genes in the biosynthetic cluster in order to allow for later selection. These additional deleted sequences should be of sufficient length that if the full deletion existed in a strain, it would be a "non-producer", i.e., not make an active product of the biosynthetic pathway. This extent of deletion is necessary for later selection steps; however, at least 2 kB should remain on either side of the target gene.

In the case of a preferred embodiment of the present invention, the target genes, either CTC 11, CTC 09, or CTC 03, are deleted along with additional sequence both upstream and downstream such that the flanking biosynthetic genes no longer encode functional proteins. The gene encoding thiostrepton resistance is inserted to mark the deletion.

The constructed fragment is placed into a vector. The vector preferably used in the present method includes the components listed in Table 3.

TABLE 3

Components of Vector

| Components (preferred embodiment) | Function |
|---|---|
| ori *E. coli* | vector replicates in *E. coli* |
| ori Streptomyces | vector replicates in Streptomyces |
| positive selectable marker (Kan$^R$) | Selection for presence of vector |
| negative selectable marker (Sm$^R$) | selection for absence of vector |
| *E. coli* promoter (Tet$_p$) | expression of selectable marker(s) in *E. coli* |
| Streptomyces or heterologous promoter (MP) | expression of selectable marker(s) in Streptomyces |
| Unique cloning site (XbaI) | insertion of constructed fragment |

The vector sequences allow replication in both Streptomyces and *Escherichia coli* to allow for use of the plasmid in either host. The vector can contain at least two genes which confer selectable phenotypes, linked to a promoter effective in Streptomyces and to a promoter effective in *E. coli*, to aid in genetic manipulations between the two organisms. Preferably, at least one gene is positively selectable (i.e., its presence confers an ability to grow under the imposed condition, such as, for example, kanamycin resistance) and at least one gene is negatively selectable (i.e., its absence confers an ability to grow under the imposed condition, such as, for example, streptomycin sensitivity). This combination of markers allows for effective selection schemes in later steps. Finally, the vector has a cloning site, preferably unique, where the constructed DNA fragment containing the deletion can be inserted. The placement of the deletion fragment into the vector is most effectively performed in *E. coli*, using techniques well known in the art.

The description of the vector above discloses the functions preferred for effective use in the methods of the present invention. The particular markers used are not essential, and any other vector carrying selectable markers or selection systems which serve the same function may be used.

For a preferred embodiment, the fragment of step two, including the thiostfepton resistance marker at the target gene locus (e.g., CTC 11, CTC 09, or CTC 03) and the corresponding flanking sequences, is inserted into the vector at the unique cloning site.

(2) Transformation and Selection for the vector in *S. aureofaciens* host

The constructed vector is introduced into a Streptomyces host, using well-known techniques such as, for example, electroporation. The appropriate host will harbor the corresponding opposite phenotypes for selection of the markers carried on the vector. Suitable hosts include, for example, any Streptomyces which has been shown to support replication of a plJ702-related plasmid.

The host used for the preferred embodiment was a kanamycin sensitive, streptomycin resistant isolate, and thiostrepton sensitive isolate (derived from *S. aufeofaciens* A377, ATCC 10762).

Putative transformants are cultured under conditions which select for a positive marker present on the vector. A preferred embodiment involved growth of the transformed cells in the presence of kanamycin, to select for the presence of the vector.

(3) First Homologous Recombination (HR1)

HR1 is illustrated in FIG. 10. The genomic copies of A, B, C (the target gene), D, and E (FIG. 10, step 1) undergo recombination with the copies of these genes present on the vector (A', B', D', and E') (FIG. 10, step 2). The sequences B' and D' differ from the genomic sequences B and D in that they have been partially deleted in the vector construct, as described above. The desired recombinants from this step are those colonies which have had a double cross-over event. Specifically, one cross-over has occurred in the sequence flanking either side of the selectable marker (see FIG. 10, step 2). This recombination event results in the placement of the selectable marker in the genome of the host at the locus of the target gene (see FIG. 10, step 3). Further, because of the deletions in the B' and D' flanking sequences, the ability of the host stain to produce the biosynthetic product is eliminated. Under ideal conditions approximately 1% of the culture population will undergo homologous recombination between the transformed vector and the genomic sequences.

The first homologous recombination event for the preferred embodiment of the present invention occurs when the a double cross-over occurs between the sequences flanking the target gene (i.e., CTC 11, CTC 09, or CTC 03) which are present on the vector, and the genomic copy of these flanking sequences. The desired recombinant is produced when one cross-over event occurs on either side of the target gene locus (now marked with the thiostrepton resistance gene). The resulting recombinant now carries the thiostrepton resistance gene in its genome, and is therefore phenotypically resistant. The recombinant also can no longer produce chlortetracycline because the genomic sequence of the flanking genes are replaced with the partially deleted (non-functional) flanking sequences of the construct.

(4) Loss of the Plasmid

Resistant colonies are then out-grown in non-selective conditions to allow for loss of the plasmid (see FIG. 10, step 4). As a second sub-step, growth conditions specific for the negatively selectable marker of the vector are utilized to ensure plasmid loss.

In the preferred embodiment of the present invention, the cells are grown without kanamycin to induce loss of the vector. The vector is rather unstable without selective pressure. However, as an safeguard, the transformed cells are grown in the presence of streptomycin such that any plasmid still present will be lost.

(5) Selection for Desired Recombinant

The desired recombination event would result in the selectable marker of the deletion being present in the genome at the locus formerly occupied by the target gene (see FIG. 10, step 4). Therefore, further selection can be performed at this stage using growth conditions selecting for the marker. If recombination has occurred as desired, the recombinant will also be a non-producer of the product of the biosynthetic pathway and this trait can be used to screen the colonies further.

The desired recombinant strain is kanamycin sensitive, thiostrepton resistant, streptomycin sensitive, and does not produce antibiotic. Thus, colonies are selected for thiostrepton resistance, and screened for inability to produce chlortetracycline.

(6) Site-directed Mutagenesis of Target Gene

The target gene is altered to increase or reduce its expression. For example, through site-directed mutagenesis using well-known techniques in the art [REFERENCE OR KIT W/SUPPLIER AND SUPPLIER'S LOCATION] or by complete deletion of its coding sequence (note such a construct would generally not delete flanking sequence, to allow for later selection). Alternatively, the gene can be placed next to a heterologous promoter, the direction of its transcription in relation to the chromosome can be switched, or rare codons can be altered to more common codons. Selection of the particular sequences to change is governed by the particular functions of the target gene. Detailed discussion of this step is made above in the "Target gene" section of the specification. As noted, the selection of the particular sequence to change is well within the purview of one of ordinary skill in the art.

The specific alterations made in the target genes of the preferred embodiment of the present invention are discussed above in the "Target gene" section of the specification. Briefly, the expression of CTC 11 or 13 can be increased by placing the gene under the control of a heterologous promoter, rare codons can be altered, and/or the direction of transcription in relation to the chromosome can be changed. The expression of CTC 09 or CTC 03 can be reduced either by complete deletion of the coding sequence, or by alteration of specific nucieotides, as discussed in detail in the Example 4.

(7) Exchange of the Wild-type and Mutated Allele (HR2)

A DNA fragment is constructed including this altered target gene where the altered gene is bracketed with sufficient sequence on either side to allow homologous recombination to occur. Note this bracketed sequence is the same as the genomic sequence, i.e., no additional sequence is eliminated. Again, approximately 2 kb on either side of the target gene is desired.

In a preferred embodiment of the present invention involved the construction a DNA fragment including the altered target gene (e.g. CTC 11 functionally linked to the MP promoter with rare codons eliminated and flipped in orientation, site mutagenized CTC 09, or deleted CTC 03) with non-deleted (functional) flanking genes.

The fragment carrying the mutated allele of the target gene is inserted into a vector. Generally, the vector used in HR1 or one having similar characteristics can be used.

A preferred embodiment of the present invention inserted the construct produced in step 10 into the vector used in HR1 at the XbaI unique cloning site.

The recombinants selected in the first stage are transformed with the vector carrying the construct described above. Transformation is performed as above of a kanamycin sensitive, thiostrepton resistant, streptomycin sensitive, and non-producer recombinant strain of step 5.

Selection for the plasmid is performed, followed by a period of outgrowth without selection, and selection against the vector, as described above. During the selection, homologous recombination 2 (HR2) occurs (see FIG. 11). Briefly, the genomic flanking sequences (B' and D') undergo homologous recombination with the copies present on the vector (B and D) (FIG. 11, step 2). The desired recombinants are those undergoing double cross-over events where a single event has occurred on either side of the target gene (FIG. 11, step 2). The desired recombinants will have the altered allele in the genomic locus of the target gene, replacing the selectable marker, and will have restored the sequences of the genes flanking the target gene (FIG. 11, step 3). Thus, the recombinants will be sensitive to the growth conditions of the selectable marker which had been carried by the host strain produced in the first stage. Further, the recombinant will produce the desired product of the biosynthesis pathway (e.g., will produce antibiotic), and this screen is used to isolate the desired recombinant. Of course, if the altered allele results in a change in the product produced (e.g., produces a demethyl product), that, and not the wild-type product, will be produced by the recombinant strain.

For the preferred embodiment of the present invention, the desired recombinant was streptomycin resistant, kanamycin sensitive, thiostrepton sensitive, and produced the desired product. Table 4 details the expected products for specific target gene alterations.

TABLE 4

Target Genes and Desired Products

| Target Gene(s) | Desired Product |
| --- | --- |
| CTC 11 only (added) | increased titer of chlortetracycline |
| CTC 09 only (altered) | 6-demethyl chlortetracycline |
| CTC 03 only (added) | increased titer of chlortetracycline |
| CTC 09 and CTC 03 (both altered) | 6-demethyl tetracycline |
| CTC 11 added with any alteration | increased titer of desired product |

As evident from the table above, multiple genes can be targeted and the process can be used to change alleles one at a time or multiple alleles during a single application of the method. For example, strains carrying a mutation in anyone or more of CTC 11, CTC 09, and CTC 03 are contemplated. Further, the produced strain can be further or solely altered by the addition of cytoplasmic expression of a gene, e.g., CTC 11, to increase expression of the desired product.

The process will now be discussed in the Examples for preparation of a S. aureofaciens strain which produces high levels of 6-demethyl tetracycline. However, as is well understood by one of ordinary skill in the art and is evident from the discussion above, this method is generally applicable to alteration of any known gene within the Streptomyces genome, and can be used to construct a strain specific for the production of any compound which can be produced through genetic manipulation of a known biosynthetic pathway.

DESCRIPTION OF THE PREFERRED EMBODIMENTS

The following examples illustrate the present invention without limitation.

EXAMPLE 1

Construction of Vector pLP21329 pLP21329 is the vector used in the present method of replacement/allele exchange. It was derived primarily for pLP21206 (FIG. 6), maintaining the unique XbaI cloning site. pLP21206, in turn was derived primarily from pPP14 (FIG. 3), and was constructed as follows.

A. Construction of pLP21206

The Micromonospora fragment pPP14 was deleted, and it was replaced with a piece of DNA carrying (in order) a transcription terminator element from the ActIII gene, a functional origin of replication derived from pBR322, and finally, an E. coli promoter (derived from that used to express the tetracycline resistance gene of pBR322) that is used to transcribe the kanamycin resistance marker in E. coli.

FIG. 12 depicts the isolation of the E. coli promoter fragment from pBR322, and fusion of this fragment to the kanamycin resistance gene derived from the transposon Tn5. Next, an approximately 200 bp fragment carrying a transcription terminator was isolated and restriction sites were manipulated in order to have correct orientation of the components of the vector to assure as little as possible transcription across the XbaI cloning site (see FIG. 13). The origin of replication pBR322 was isolated and inserted into the construction (FIG. 14). The isolated ori fragment was linked to the E. coli promoter, and then linked with the Act III terminator (FIG. 15). Finally, the entire constructed fragment was inserted into pPP14 to form pLP21206 (FIG. 16).

B. Construction of pLP21329 pLP21329 was constructed in a series of steps which involved the deletion of the thiostrepton and kanamycin markers and replacement with a fragment including the Micromonospora promoters fragment, the E. coli promoter from pBR322, a streptomycin sensitivity gene, and the Tn5 derived kanamycin resistance gene. The streptomycin sensitivity gene is located on a 430 bp fragment derived from Micrococcus luteus (ATCC 4698). The gene was selected because its published sequence indicated that the gene was high in GC content (about 72%), thus the chances of it being efficiently expressed in Streptomyces was increased.

a. Promoter-kanamycin construct

The first step involved the isolation of the Micromonospora promoters fragment from pPP14 (FIG. 3) and placing it in functional linkage with the E. coli promoter and the kanamycin resistance gene (see FIGS. 15 and 16) to form the promoter-kanamycin construct. Next, replication sequences for Streptomyces were isolated from plJ702 (FIG. 19) and linked to the promoter-kanamycin construct (FIG. 20).

b. Streptomycin sensitivity gene

The streptomycin sensitivity gene from M. luteus was isolated as follows. Genomic DNA was isolated using standard methods and reagents. The desired fragment was isolated by PCR using a Perkin-Elmer/Cetus (Norwalk, Conn.) Gene Amp® kit essentially under the conditions recommended.

The initial PCR amplification reaction used the following oligonucleotides as primers:

SO 50: 5'-CTTCGGCGCAAGACCCTTACGAGGC-3'
SO 52: 5'-TTGGCGTGCGGGGCCGGCTCGTCGA-3'

This reaction yielded a product of about 650 bp which was purified and used as a template in a second round of PCR amplification using the following oligonucleotides as primers:

SO 51: 5'-ACACAGGAAGACTGAAGAGTGCCTA-3'
SO 52: 5'-TTGGCGTGCGGGGCCGGCTCGTCGA-3'

In this case, as smaller PCR product was obtained as expected of about 430 bp. This was phosphorylated with $T_4$ polynucleotide kinase (New England Biolabs, Beverly, Mass.) using recommended conditions, after gel purification. This product, assumed to have protruding 3'-A residues was cloned in the XcmI digested and dephosphorylated pLP21207 (FIG. 21). This vector is a modified version of the "lac po" deletion of pNEB193 (FIGS. 22 and 23). In pLP21207, the normal Acc65I site in the polylinker was removed by insertion of two NheI linkers (creating a NgoMI site). Synthetic oligonucleotides SO42 and SO43:

SO 42: 5'-GATCCCATCACTCAGTTGGTAC-3'

SO 43: 5'-CAACTGACTGATGG-3' were ligated and then inserted into the BamHI site of pLP21207. Finally, a 1500 bp fragment of bacteriophage lambda was inserted into the now unique ACC65I site yielding the following:

```
BamHI         XcmI             XcmI          BamHI
GGATCCCATCAGTCAGTTGGTACC1500bpGGTACCAACTGACTGATGGGATCC

CCTAGGTAGTCAGTCAACCATGG1500bpCCATGGACTGACTGACTACCCTAGG
```

The cloned 430 bp fragment was then recovered as a BamHI fragment of about 450 bp and ligated into the BclI cut and dephosphorylated pLP21024 yielding pM71-4293 (see FIG. 24).

c. Assembly of pLP21329

As a final step the plasmids produced from steps a) and b) above are ligated together to form pLP21329 (see FIG. 25).

EXAMPLE 2
Construction of Deletion Fragment

As a representative example, the construction of the recombinant fragments necessary for the alteration of the CTC 09, methylation enzyme, are be given. Parallel techniques were used for the alteration of CTC 11 and CTC 03. Throughout this example whenever base pair numbering is given this numbering refers to the sequence FRE 04 (bp1) through CTC 29 (bp35,801) (see the numbering of U.S. application Ser. No. 08/125,468 filed Sep. 22, 1993 and add 5800 bp to account for additionally elucidated upstream sequence).

A. Construction of Plasmid with Fragment of Biosynthetic Pathway

A 12 kB fragment (bp 13105-23956) from the original cosmid clone were placed into the E. coli vector plBI24. Digestion of this subcloned fragment allowed isolation of two pieces after incuabtion witht the restriction enzymes AscI and BamHI. These two AscI and BamHI fragments bracket the region to be deleted—BanHI(13105)-AscI (15412) and AscI(19428)-BamHI(23,956). To serve as a specialized vecto for this construction, the plasmid pLP-1207 was digested with EcI36II, dephosphorylated, and then ligated with SpeI linkers yielding the following polylinker:

EcoRISpeINheINgoMINheISmaIAscIBamHIXcmI 1500 bp lambda seq. BamHIXbaISalIPmeIPstISphIHindIII Digestion of this DNA with AscI and BamHI followed by dephosphorylation allowed the cloning of the two fragments described above. The sequence between these two fragment were deleted.

B. Insertion of the Thiostrepton Resistence Marker

The gene was isolated as a 1 Kb BclI fragment from plJ101 (FIG. 26). The ends were filled in and the fagment was cloned into a filled in and phsphatased NgoHI site formed b the insertion of two NheI linkers (New England BioLab:GGCTAGCC) into the larger fragment obtained by digesting pNEB193 with PvuII. The net result is that the Tsr$^R$ gene is backeted by a NheI recognistion site, allowing the isolation of Tsr$^R$ as an NheI fragment.

This gene fragment was placed into the site deleted above and used to transform the S. aureofaciens host, as described below.

EXAMPLE 3
Transformation of Vector into S. aureofaciens and Plasmid Loss

A. Preparation of cells

DNA is introduced into S. aureofaciens by eletroporation. The cells are prepared by inoculating TSBG media (bacto tryptic-soy broth (Difco, Detroit, Mich.) supplemented with 2% glucose) with 0.2–0.3 ml of a frozen vegetative mycelia stock culture. These cultures are then grown generally in 10 ml media in a 25 mm×150 mm glass tube containing a glass rod (ends not fire-polished) about 5×45 mm. The tubes are held vertically in an appropriate rack and shaken at 200 rpm. The temperature used for incubation ranges from about 26° C. to about 30° C.

The cultures are incubated for 24–48 hours until thick growth is observed and then 0.2 to 0.3 ml are inoculated in to 10 ml of the same medium containing 1.5% glycine (about 1.2 to about 1.6 is the general functional range). The effective level of glycine is thought to be strain dependent, but such determination is well within one of ordinary skill. The amount to be added should be sufficient to enhance protoplast formation by the lysozyme digestion in the subsequent steps. These cells are incubated for about 40 hours (range of about 24-about 48 hours) until the growth is no longer made up of primarily of mycelial "pellets" or "flakes".

The glycine grown cultures are centrifuged (e.g. 8000 rpm, LS-14 rotor, Beckman Instruments, Palo Alto, Calif.) in a J2M1 centrifuge at 4° C. for about 10 minutes. The cell pellet is resuspended in ice-cold sterile deionized water (about one-half volume relative to the original culture) and centrifuged as above. The procedure is repeated at least twice more.

The cell pellet is then resuspended in ice-cold sterile 10% glycerol (V/V) in deionized water and centrifuged as above. The resulting cell pellet is finally resuspended in 10% glycerol and aliquots frozen at −80° C. and stored at that temperature until use.

B. Electrororation

About 15 μl of DNA (in, e.g. 0.01M Tris-HCL-0.001 M EDTA: pH 7.4), 150 μl 40% PEG 3350 (Sigma, St. Louis, Mo.) (freshly prepared and filter sterilized), and 150 μl of the above prepared cells. The mixture is vortexed and stored on ice (as are the electroporation cuvettes: 2 mm gap, BioRad, Richmond, Calif.). These components can be scaled up or down (proportionally) depending on the number of transformants needed.

The mixture is added to the cuvette and electroporated at 1800 V using a 25 μfarad capacitor setting and a valve of 600 ohms for the pulse controller of a BioRad GenePulser™ instrument. The cells are immediately added to 3 ml of TSGB medium in a 25×150 mm glass tube but without the glass rods mentioned above. The transformed cells are outgrown for at least two hours and then spread on trypticsoy agar plates supplemented with 2% glucose and the appropriate antibiotic, kanamycin is generally used at 50 μg/ml. Thiostrepton is added at a range of about 25 μg/ml–50 μg/ml. the plates are incubated at 26° C.–30° C., depending on the host strain and the DNA introduced. Transformants will be observed in as early as 3 days or as many as 10 days.

C. Selection

Transformants are picked from kanamycin plates and directly inoculated into 10 ml TSB+2% glucose medium in tubes with glass rods and grown to saturation (about 40–72 hours). The cultures can then be diluted and plated directed onto TSA (Tryptic-soy agar) plates with 100 μg streptomycin or preferably, about 0.2–0.3 ml can be inoculated into 10 ml of TSB+2% glucose and 100 μg/ml streptomycin and again grown to saturation (about 24 to 72 hours). The amount of time necessary depends on the number of cells which have lost the plasmid during the initial outgrowth. Again, the culture is diluted and plated on TSA plates with 100 μg/ml streptomycin. Individual colonies are replicapicked to 3 sets of plates (TSA with 20–50 μg thiostrepton, 50 ug kanamycin, and 100 ug/ml streptomycin) to identify apparent plasmid-free recombinants. Antibiotic production/non-production can be evaluated by flask fermentations or by using an overlay test. An over-lay test involves growing a colony (or, e.g. patch inoculated with 0.1 ml liquid culture) on CTC production Agar Ver. 1.1 (see Table 5) at 26° C. for 5–7 days and then the entire plate is overlaid with 4 ml of 20-10-5 soft agar (20 g tryptone, 10 g yeast extract, 5 g sodium chloride and 8 g/l Bacto-agar) containing 0.1 ml. of a *Bacillus subtilis* or *E. coli* indicator. The overlaid plate is incubated at 37° C. overnight and the presence/absence of a zone of inhibition around the *S. aureofaciens* colony/patch is a rapid test for production or non-production. Thus, in cases where the host *S. aureofaciens* carries a deletion that results in non-production, the desired recombinants (vector-free) should be detectable (after outgrowth in liquid media and streptomycin) by plating the culture on drug-free media (for example, CTC production agar) and after the colonies are gown, overlaying with the above-discussed indicators. Colonies surrounded by a zone of inhibition would be recovered by being picked to a streptomycin plate.

TABLE 5

Formulation of CTC Production Agar Ver. 1.1

| Ingredient | Manufacturer | G/L |
|---|---|---|
| NZ Amine | | 10 |
| Soluble Starch | Difco, Detroit, MI | 50 |
| Trace Elements | 500X stock | 2 ml |
| $(NH_4)_2SO_4$ | | 10 |
| $NH_4Cl$ | | 2.5 |
| $KH_2PO_4$ (2.5 g/l) | Stock solution | 2 ml |
| Yeast Extract | Difco, Detroit, MI | 1 |

Adjust pH to 7.0
$dH_2O$ to 1 liter

EXAMPLE 4

Construction of Site-directed Mutagenized Allele Fragment

Site specific mutagenesis experiments were carried out using oligonuclotides purchased from National Biosciences (Plymouth, Minn.) and a kit (Muta-Gene●M13 in vitro mutagenesis kit version 2) from BioRad (Richmond, Calif.). The procedure is based on the method of Kunkel, *Proc. Natl. Acad. Sci. USA* 82:488–492, 1985) and Kunkel et al. *Methods Enzymol.* 154: 367–382, 1987).

The construction resulting from the site-directed mutagenesis was placed within pLP-1281 to yield the plasmid illustrated in 27. The EcoRI and Hin dIII fragments containing the CTC09 gene was transferred to M13 mp18, single stranded DNA isolated and site-directed mutagenesis carried out as above using the following oligonucleotide:

S$^1$TG GTG GAC ATC GCC GGT GTC CAG GTG CAC GTG CTG ACC ACC$^{-3'}$ which change two glycine residues (aa 185 and 187) to valine residues which were believed to be part of an S-adenosyl-methionine binding site since a number of amino acids in this region are conserved in a number of methylases.

This construct was transfered (as waas all the other joint mutations in CTC09) allele to a vector that had sufficient DNA on either side for recombination to occur and to restore this gene to its normal regulatory environment (i.e., no Micromonospora promoters) within the *S. Aureotacins* genome.

Cloning a larger piece of DNA involved changing the Eco 109I site in pNEB193 to an NDEI sitan and the ATiIII to an SpeI site by digetsting with the appropriate enzyme, fill in, dephosphylate, and ligate to a linker. The previously cloned BamHI fragment (see FIG. 27) was moverd from plBI24 to this vector as an EcoRI-HindIII fragment yielding the plasmid illustrated in FIG. 28. Note, the CTC 09 gene encompasses sequence number 16752-17789.

Next step in the process involved creating a molecule with the NdeI site being introduced to CTC09 and a unique NCOI site to allow the mutagenized alleles to be moved in as NdeI-NcoI fragments. This is done in such a way that the next step was to transfer to the large BAMHI fragment as a DraIII piece in only possible orientation: because Dra III has an assymetric target site (DraIII=CAC NNN GTH).

Since this fragment is bounded by NheI and SpeI sites, the entire reconstructed molecule could be transferred directly to the unique XbaI site of pLP2-1329 (see FIG. 29). Clone the filled in ApaI fragment from the cosmid carrying the CTC pathway (15997-18714) between two Nhe I sites in the pNEB193 derivative mentioned above (see FIG. 29).

Next, dione the about 1600 AgeI fragment that lies "upstream" of the CTC09 gene (and includes the second DraIII site that needs to be brought in) and insert into the unique AgeI site in the above to yield the plasmid illustrated in FIG. 30.

Then, the lacpo deletion pNEB193 is used as the vector, where the insert is at the SphI site which has been changed to NcoI as above using an NcoI linker. Use this as the vector to clone the above BamHI(13105)-NcoI(18250) fragment (see FIG. 31).

Finally, as illustrated in FIG. 32, the final vector to electroporate into the cells is constructed.

Similar procedures using appropriate oligonucleotides were utlized to form the mutants of CTC 11 as described in Table 6. As seen Table 6, the rare codon ATT present at positions 5 and 15 were altered (see column 3). Orientation was changed relative to the chromosome (INV) or unchanged (wt). The "# leader" column refers to a cloning artifact which increases the introductory sequence by an additional amino acid in some constructs. The titer values reported should be were carried out as described in Example 6 and should be compared to a baseline of less than 100 mg/ml for an unaltered strain.

Further, mutations were made at the following amino acid positions of CTC 09. D 172 was changed to R, and D 172 was changed to V, however no effect on titer was seen. Singly G 184 was changed to V, singly G 187 was changed to V, in combination both D 181 was changed to V and G 185 was changed to V, and in combination both G 185 was changed to V and G 187 was changed to V. Finally, a frameshift was introduced at resdue 17293, approximately ⅓ of the way through the coding sequence. Each of these combinations resulted in inactivation of the CTC 09 gene product.

TABLE 6

Site directed Mutations For CTC 11
5 = met~
6 = met val~

| Clone # | "# leader" Amino Acids | ATT → ATC Changed? | Orientation | mg/ml CTC titer |
|---|---|---|---|---|
| 201 | 5 | #13 | wt | 929 |
| 208 | 5 | #13 | wt | 280 |
| 209 | 5 | #13 | wt | 1319 |
| 222 | 6 | #5 | INV | 394 |
| 231 | 5 | #5 & #15 | wt | 856 |
| 232 | 5 | #5 & #15 | wt | 462 |
| 233 | 5 | #5 & #15 | 25 | 1457 |
| 238 | 5 | #5 & #15 | INV | 5187 |
| 239 | 5 | #5 & #15 | INV | 4668 |
| 251* | 6 | #5 & #15 | INV | 1426 |
| 252* | 6 | #5 & #15 | INV | 745 |
| 253* | 6 | #5 & #15 | INV | 3565 |
| 254* | 6 | #5 & #15 | INV | 3620 |
| 257 | wt(5) | — | wt | 1564 |
| 259 | wt(5) | — | wt | 2208 |
| 265 | wt(5) | — | INV | 2378 |
| 266 | wt(5) | — | INV | 2666 |
| 270 | wt(5) | — | INV | 2710 |

*2 copies i.e., CTC11, CTC11, CTC14

The surviving plaque-forming phage obtained after this site-specific mutagenesis procedure were grown and the double stranded replicative form was isolated. The desired mutants with and extra NdeI site were digested with NdeI and XhoI releasing a 971 bp fragment.

EXAMPLE 5
Transformation of Recombinant Host and Plasmid Loss

EXAMPLE 6
Testing of the Produced Strain

The putative recombinant strains undergo a flask fermentation to produce media to be tested for desired compound. TSGB is used as the seed medium. Culture as described above, including the glass rod. 10 ml of TSGB is inoculated with about 0.2 ml of the colony to be tested. Incubate at 29° C.–30° C. for 48 hr at 200 rpm. Inoculate 25 ml of CTC medium in a 250 ml Erlenmeyer flask with 1 ml of the seed culture. Incubate at 26° C. for 7 days on a rotary shaker at 200 rpm.

Media for this process is made as follows: TSBG: 30 g/L Bacto Tryptic Soy Broth and 20 g/L glucose; CTC Fermentation Medium: 50 g/L Difco Bacto Starch, 5 g/L $(NH_4)_2SO_4$, 10 g/L $CaCO_3$, 2 g/L $NH_4Cl$, 5 g/L Difco Bacto Casein, 2 mL/L 500× tract elements, 2 g/L $MgCl_2$-6 $H_2O$, 140 mg/L $MnSO_4$, 5 mg/L $CoCl_2$-$6H_2O$, 10 g/L cornsteep liquor, 1.5 mL/flash Progresso pure olive oil. Mix ingredients, except olive oil in order listed in approximately 700 ml deionized water, qs to 1 L. Dispense 25 mL into 250 mL erlenmeyer flasks. Add 1.5 mL olive oil to each flask. 500× trace elements: 40 mg $ZnCl_2$, 10 mg $CuCl_2$, 10 mg $MnCl_2$-$4H_2O$, 10 $Na_2B_4O_7$-10 $H_2O$, 10 mg $(NH_4)_6Mo_7O_{24}$-$4H_2O$, 200 mg $FeCl_3$-$6H_2O$. Add reagent to deionized water and QS to 1 liter. AP6 agar: 0.25 g $MgSO_4$-$7H_2O$, 2 g $KH_2PO_4$, 2 g $(NH_4)_2HPO_4$, 10 g sucrose, 6 g corn steep liquor, 20 g Bacto Agar. Add ingredient to deionized water and QS to 1 liter. Autoclave for 20 min.

Media produced by the putative selected strains are tested for the production of the desired compound using high pressure liquid chromatography (HPLC). A 1:5 dilution of the fermentation mash in acid methanol (2.75 mL of concentrated $H_2SO_4$ in 1 L HPLC grade methanol). Vortex for 10 minutes, centifuge or allow solids to settle, and filter though 0.45 μsyringe filters (Gelman Acrosdisc] into HPLC vials. The HPLC is performed as follows. The mobile phase is made by preparing 1 liter 0.1M oxalic acid, where 780 ml is mixed with 220 ml of HLPC grade deoxymethyifluoride (DMF). The pH of this solution is brought to 2.9 using concentrated ammonium hydroxide, and it is filtered and degased before use.

The HPLC is run with a 1.5 mL/min flow rate, the temperature at 35° C., and a column of Hypersil ODS 4.6×100 mm with 5 μm packing. 10 μl of medium is tested and detection is set at UV 365 nm. The samples and standards are prepared in 0.1N $H_2SO_4$ in methanol (approximately 11 mL of $H_2SO_4$ in 4 L of methanol). The standard should be prepared approximately the same concentration level as anticipated in the diluted sample.

The vector for use with the present invention was deposited on _____ at the ATCC facility in Rockville, Md. It has accession number ATCC _____. The strains _____, _____, and _____ of the present invention were deposited on _____ at the ATCC facility in Rockville, Md. They have accession numbers ATCC _____, ATCC _____, and ATCC _____, respectively. The vector and strains are available to the public when legally applicable.

According to the present invention, 6-demthyl tetracycline or other chlortetracycline derivative can be produced by culturing the cells produced using the present method and isolating the compound from the culture.

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claims.

What is claimed:

1. A recombinant *S. aureofaciens* cell comprising a recombinant CTC 11 gene, wherein expression of the CTC 11 gene is enhanced relative to that of a wild-type CTC 11 gene in an *S. aureofaciens* cell.

2. The recombinant *S. aureofaciens* according to claim 1, wherein the CTC 11 gene expression is under control of a heterologous promoter.

3. The recombinant *S. aureofaciens* according to claim 2, wherein the heterologous promoter is contained on a 400 bp fragment of *Micromonospora echinospora*.

4. The recombinant *S. aureofaciens* according to claim 1, wherein the CTC 11 gene is chromosomal.

5. The recombinant *S. aureofaciens* according to claim 4, wherein the CTC 11 gene is in an inverse orientation relative to a wildtype CTC 11 gene.

6. The recombinant *S. aureofaciens* according to claim 1, wherein the CTC 11 gene is extra-chromosomal.

7. The recombinant *S. aureofaciens* according to claim 1, further comprising a CTC 09 gene, wherein the CTC 09 gene is inactivated.

8. The recombinant *S. aureofaciens* according to claim 7, further comprising a CTC 03 gene, wherein the CTC 03 gene is inactivated.

9. The recombinant *S. aureofaciens* according to claim 8, which produces demethyltetracycline.

10. A method for production of demethyltetracycline, which method comprises
   a) culturing the *S. aureofaciens* cell according to claim 9 under conditions in which a tetracycline compound is produced; and
   b) harvesting the demethyltetracycline from the culture.

11. The recombinant *S. aureofaciens* according to claim 7, which produces demethylchlorotetracycline.

12. The recombinant *S. aureofaciens* according to claim 1, further comprising a CTC 03 gene, wherein the CTC 03 gene is inactivated.

13. The recombinant *S. aureofaciens* according to claim 12, which produces tetracycline.

14. A method for production of tetracycline, which method comprises
   a) culturing the *S. aureofaciens* cell according to claim 13 under conditions in which a tetracycline compound is produced; and
   b) harvesting the tetracycline from the culture.

15. A method for production of demethylchlorotetracycline, which method comprises
   a) culturing the *S. aureofaciens* cell according to claim 12 under conditions in which a tetracycline compound is produced; and
   b) harvesting the demethylchlorotetacycline from the culture.

16. The recombinant *S. aureofaciens* according to claim 1, which produces chlorotetracycline.

17. A method for production of a tetracycline compound, which method comprises
   (a) culturing the *S. aureofaciens* cell according to claim 1 under conditions in which a tetracycline compound is produced; and
   b) harvesting the tetracycline compound from the culture.

18. The method according to claim 17, wherein the tetracycline compound is chlorotetracycline.

19. A recombinant *S. aureofaciens* cell comprising a CTC 03 gene, wherein the CTC 03 gene is inactivated.

20. The recombinant *S aureofaciens* according to claim 19, wherein the CTC 03 gene is inactivated by mutagenesis.

21. The recombinant *S. aureofaciens* according to claim 20, further comprising a CTC 09 gene, wherein the CTC 09 gene is inactivated.

22. The recombinant *S. aureofaciens* according to claim 21, further comprising a second CTC 03 gene, wherein one of the CTC 03 genes is chromosomal and the other is extra-chromosomal, and both CTC 03 genes are inactivated.

23. The recombinant *S. aureofaciens* according to claim 21, which produces demethylchlorotetracycline.

24. The recombinant *S. aureofaciens* according to claim 19, which produces tetracycline.

25. A recombinant *S. aureofaciens* cell comprising a CTC 09 gene, wherein the CTC 09 gene is inactivated.

26. The recombinant *S. aureofaciens* according to claim 25, wherein the CTC 09 gene is inactivated by mutagenesis.

27. The recombinant *S. aureofaciens* according to claim 25, which produces demethyltetracycline.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

CTTCGGCGCA AGACCCTTAC GAGGC                                              25

(2) INFORMATION FOR SEQ ID NO:2:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

TTGGCGTGCG GGGCCGGCTC GTCGA                                              25

(2) INFORMATION FOR SEQ ID NO:3:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

ACACAGGAAG ACTGAAGAGT GCCTA                                              25

(2) INFORMATION FOR SEQ ID NO:4:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

TTGGCGTGCG GGGCCGGCTC GTCGA                                              25

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

GATCCCATCA CTCAGTTGGT AC                                                 22

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

CAACTGACTG ATGG                                                          14

(2) INFORMATION FOR SEQ ID NO:7:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

GGATCCCATC AGTCAGTTGG TACCNGGTAC CAACTGACTG ATGGGATCC                    49

(2) INFORMATION FOR SEQ ID NO:8:

(i) SEQUENCE CHARACTERISTICS:
        (A) LENGTH: 41 base pairs
        (B) TYPE: nucleic acid
        (C) STRANDEDNESS: single
        (D) TOPOLOGY: linear

```
      (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

TGGTGGACAT CGCCGGTGTC CAGGTGCACG TGCTGACCAC C                           41
```